(12) United States Patent
Anderson et al.

(10) Patent No.: US 9,303,042 B2
(45) Date of Patent: Apr. 5, 2016

(54) TRIAZOLOTHIENOPYRIMIDINE COMPOUND INHIBITORS OF UREA TRANSPORTERS AND METHODS OF USING INHIBITORS

(71) Applicant: The Regents of the University of California, Oakland, CA (US)

(72) Inventors: Marc Anderson, San Francisco, CA (US); Alan S. Verkman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/388,645

(22) PCT Filed: Mar. 27, 2013

(86) PCT No.: PCT/US2013/034063
§ 371 (c)(1),
(2) Date: Sep. 26, 2014

(87) PCT Pub. No.: WO2013/148813
PCT Pub. Date: Oct. 3, 2013

(65) Prior Publication Data
US 2015/0057274 A1     Feb. 26, 2015

Related U.S. Application Data

(60) Provisional application No. 61/616,343, filed on Mar. 27, 2012, provisional application No. 61/798,150, filed on Mar. 15, 2013.

(51) Int. Cl.
| | | |
|---|---|---|
| *A61K 31/519* | (2006.01) | |
| *C07D 495/22* | (2006.01) | |
| *A61P 7/10* | (2006.01) | |
| *A61P 9/12* | (2006.01) | |
| *A61P 9/04* | (2006.01) | |
| *A61P 13/12* | (2006.01) | |
| *A61P 13/02* | (2006.01) | |

(52) U.S. Cl.
CPC .............. *C07D 495/22* (2013.01); *A61K 31/519* (2013.01)

(58) Field of Classification Search
CPC ............................ C07D 495/22; A61K 31/519
See application file for complete search history.

(56) References Cited

U.S. PATENT DOCUMENTS

| | | |
|---|---|---|
| 8,394,788 B2 | 3/2013 | Verkman et al. |
| 2009/0275586 A1 | 11/2009 | Govek et al. |
| 2010/0190796 A1 | 7/2010 | Verkman et al. |
| 2011/0053995 A1 | 3/2011 | Verkman et al. |

FOREIGN PATENT DOCUMENTS

| | | |
|---|---|---|
| WO | 02/100842 A1 | 12/2002 |
| WO | 2008/016248 A2 | 5/2008 |
| WO | 2008/061247 A2 | 5/2008 |
| WO | 2008/067196 A2 | 6/2008 |
| WO | 2009/093934 A2 | 7/2009 |

OTHER PUBLICATIONS

Anderson et al., "Nanomolar Potency and Metabolically Stable Inhibitors of Kidney Urea Transporter UT-B," *J. Med. Chem.* 55:5942-5950, 2012.

Bagnasco et al., "Cloning and characterization of the human urea transporter UT-A1 and mapping of the human S1c14a2 gene," *American Journal of Physiology & Renal Physiology*, 281:F400-F406, 2001.

Bagnasco, "Gene structure of urea transporters," *American Journal of Physiology & Renal Physiology*, 284:F3-F10, 2003.

Bagnasco, "Role and regulation of urea transporters," *Pflügers Archive: European Journal of Physiology*, 450(4):217-226, 2005.

Baldwin et al., "Characterization of the cytochrome P450 enzymes involved in the in vitro metabolism of rosiglitazone," *J Clin Pharmacol* 48:424-432, 1999.

Bankir et al., "Lack of UT-B in vasa recta and red blood cells prevents urea-induced improvement of urinary concentrating ability," *Am J Physiol Renal Physiol* 286:F144-F151, 2004.

Doran et al., "Tissue distribution of UT-A and UT-B mRNA and protein in rat," *Am J Physiol Regul Integr Comp Physiol* 290:R1446-R1459, 2006.

Esteva-Font et al., "A Small Molecule Screen Identifies Selective Inhibitors of Urea Transporter UT-A," *Chemistry & Biology* 20:1235-1244, Oct. 24, 2013.

Esteva-Font et al., "Diuresis and reduced urinary osmolality in rats produced by small-molecule UT-A-selective urea transport inhibitors," *The FASAB Journal* 28:3878-3890, Sep. 2014.

Esteva-Font et al., "Structure-activity analysis of thiourea analogs as inhibitors of UT-A and UT-B urea transporters," *Biochimica et Biophysica Acta* 1848:1075-1080, 2015.

Esteva-Font et al., "Urea transporter proteins as targets for small-molecule diuretics," *Nature Reviews Nephrology* 11:113-123, Feb. 2015.

Fenton et al., "Renal Phenotype of UT-A Urea Transporter Knockout Mice," *J. Am. Soc. Nephrol.* 16:1583-1592, 2005.

Fenton et al., "Urinary concentrating defect in mice with selective deletion of phloretin-sensitive urea transporters in the renal collecting duct," *Proc. Natl. Acad. Sci. USA* 101(19):7469-7474, 2004.

(Continued)

*Primary Examiner* — Susanna Moore
(74) *Attorney, Agent, or Firm* — Seed IP Law Group PLLC

(57) ABSTRACT

Provided herein are small molecule triazolothienopyrimidine compounds that inhibit urea transport activity of solute transporters, particularly the UT-B transporter. The compounds described herein are useful for increasing solute clearance in states of fluid overload and for treating refractory edema associated with cardiovascular, renal, and metabolic diseases, disorders, and conditions.

20 Claims, 11 Drawing Sheets

(56) References Cited

OTHER PUBLICATIONS

Fenton, "Essential role of vasopressin-regulated urea transport processes in the mammalian kidney," *Pflugers Arch—Eur J Physiol* 458:169-177, 2009.
Fenton, "Urea transporters and renal function: lessons from knockout mice," *Current Opinion in Nephrology and Hypertension* 17:513-518, 2008.
Fröhlich et al., "Regulation of UT-A1-mediated transepithelial urea flux in MDCK cells," *American Journal of Physiology & Cell Physiology*, 291:C600-C606, 2006.
Goldsmith, "Current Treatments and Novel Pharmacologic Treatments for Hyponatremia in Congestive Heart Failure," *The American Journal of Cardiology*, 95(9A):14B-23B, 2005.
Khojasteh-Bakht et al., "Identification of the human cytochrome P450s responsible for the in vitro metabolism of a leukotriene B4 receptor antagonist, CP-195,543," *Xenobiotica* 33(12):1201-1210, 2003.
Klein et al., "Upregulation of Urea Transporter UT-A2 and Water Channels AQP2 and AQP3 in Mice Lacking Urea Transporter UT-B," *Journal of the American Society of Nephrology*, 15:1161-1167, 2004.
Levin et al., "Crystal structure of a bacterial homologue of the kidney urea transporter," *Nature* 462:757-762, Dec. 10, 2009.
Levin et al., "Urearetics: a small molecule screen yields nanomolar potency inhibitors of urea transporter UT-B," *The FASEB Journal*, 21:551-563, 2007.
Liu et al., "1,1-Difluoroethyl-substituted triazolothienopyrimidines as inhibitors of a human urea transport protein (UT-B): New analogs and binding model," *Bioorg Med Chem Lett* 23(11):3338-3341, 2013.
Lucien et al., "Characterization of the Gene Encoding the Human Kidd Blood Group/Urea Transporter Protein," *The Journal of Biological Chemistry*, 273(21):12973-12980, 1998.
Ma et al., "Severely Impaired Urinary Concentrating Ability in Transgenic Mice Lacking Aquaporin-1 Water Channels," *The Journal of Biological Chemistry*, 273(8):4296-4299, 1998.
Macey et al., "Independence of Water and Solute Pathways in Human RBCs," *Journal of Membrane Biology*, 134(3):241-250, 1993.
Martial et al., "Urea derivatives as tools for studying the urea-facilitated transport system," *Pflügers Archive: European Journal of Physiology*, 423:51-58, 1993.
Meng et al., "Surface electrocardiogram and action potential in mice lacking urea transporter UT-B," *Science in China Series C: Life Sciences* 52(5):474-478, 2009.
Miller, "Hyponatremia and Arginine Vasopressin Dysregulation: Mechanisms, Clinical Consequences, and Management," *Journal of the American Geriatrics Society*, 54(2):345-353, 2006.
Sands, "Mammalian Urea Transporters," *Annual Review of Physiology*, 65:543-566, 2003.
Sands, "Renal urea transporters," *Current Opinion in Nephrology and Hypertension*, 13(5):525-532, 2004.
Sands et al., "The Physiology of Urinary Concentration: an Update," *Semin Nephrol* 29(3):178-195, 2009.
Sands et al., "Urea transporters in kidney and erythrocytes," *The American Journal of Physiology*, 273:F321-F339, 1997.
Sands et al., "Urinary Concentrating Ability in Patients with Jk(a-b-) Blood Type Who Lack Carrier-Mediated Urea Transport," *Journal of the American Society of Nephrology* 2:1689-1696, 1992.
Shayakul et al., "The SLC14 gene family of urea transporters," *Pflügers Archive: European Journal of Physiology*, 447:603-609, 2004.
Sidoux-Walter et al., "At Physiological Expression Levels the Kidd Blood Group/Urea Transporter Protein Is Not a Water Channel," *The Journal of Biological Chemistry*, 274(42):30228-30235, 1999.
Smith, "Mammalian urea transporters," *Exp Physiol* 94(2):180-185, 2009.
Stewart et al., "Acute regulation of mUT-A3 urea transporter expressed in a MDCK cell line," *Am J Physiol Renal Physiol* 292:F1157-F1163, 2007.
Stewart, "The emerging physiological roles of the SLC14A family of urea transporters," *British Journal of Pharmacology* 164:1780-1792, 2011.
Tickle et al., "Novel bUT-B2 urea transporter isoform is constitutively activated," *Am J Physiol Regul Integr Comp Physiol* 297:R323-R329, 2009.
Tsukaguchi et al., "Cloning and Characterization of the Urea Transporter UT3," *The Journal of Clinical Investigation*, 99(7):1506-1515, 1997.
"urea transporter-B1 [*Homo sapiens*]," GenBank Accession No. CAB60834.1, retrieved from http://www.ncbi.nlm.nih.gov/protein/CAB60834, on Mar. 31, 2015, 1 page.
Verkman et al., "Small-Molecule Inhibitors of Urea Transporters," *Subcell Biochem* 73:165-177, 2014.
Yang et al., "Urea-selective Concentrating Defect in Transgenic Mice Lacking Urea Transporter UT-B," *The Journal of Biological Chemistry*, 277(12):10633-10637, 2002.
Yao et al., "Triazolothienopyrimidine Inhibitors of Urea Transporter UT-B Reduce Urine Concentration," *J Am Soc Nephrol* 23:1210-1220, 2012.
Zhang et al., "Theoretical effects of UTB urea transporters in the renal medullary microcirculation," *Am J Physiol Renal Physiol* 285:F731-F747, 2003.

TRIAZOLOTHIENOPYRIMIDINE COMPOUND INHIBITORS OF UREA TRANSPORTERS AND METHODS OF USING INHIBITORS

CROSS-REFERENCE TO RELATED APPLICATION

This application claims the benefit under 35 U.S.C. §119(e) to U.S. Provisional Application No. 61/616,343 filed Mar. 27, 2012, and U.S. Provisional Application No. 61/798,150 filed Mar. 15, 2013 which applications are incorporated by reference herein in their entirety.

STATEMENT OF GOVERNMENT INTEREST

This invention was made with government support under Grant Nos. DK35124, DK72517, DK86125, EB00415, HL73856 and EY13574 awarded by the National Institutes of Health. The government has certain rights in this invention.

BACKGROUND

1. Technical Field

Agents that inhibit urea transport activity are needed as therapeutic agents for increasing solute clearance in states of fluid overload and for treating diseases and conditions such as hypertension. Agents that inhibit urea transporters and methods for using these agents are described herein.

2. Description of the Related Art

Urea is generated by the liver as the major end product of nitrogen metabolism, released into the blood, and excreted by the kidneys. The processing of urea by the kidney is complex, involving countercurrent multiplication and exchange mechanisms that greatly increase urea concentration in the renal medulla compared to serum. In the maximally concentrating (antidiuretic) kidney, urea concentration in the urine can reach >1000 mM in mammals (see, e.g., Bankir et al., "Urea and the kidney" In: *The Kidney*. 6th ed., edited by Brenner B M, Philadelphia, (WB Saunders, 2000), 637-679; Sands et al., *Semin Nephrol* 29:178-95, 2009) much greater than the serum urea concentration of 4-10 mM. The renal countercurrent mechanisms involve intrarenal urea recycling facilitated by urea transporters (UTs) expressed in renal tubule epithelial cells (UT-A, encoded by the SLc14A2 gene) and renal vasa recta microvessels (UT-B, encoded by the SLc14A1 gene) (see, e.g., Bagnasco, *Am J Physiol Renal Physiol* 284: F3-F10, 2003; Sands, *Curr Opin Nephrol Hypertens* 13:525-32, 2004; Shayakul et al., *Pflugers Arch* 447: 603-609, 2004; Stewart, *Br J Pharmacol* 2011 Mar. 30, doi:10.1111/j.1476-5381.2011.01377.x Epub ahead of print; Tsukaguchi et al., *J Clin Invest* 99:1506-15, 1997. Phenotype analysis of knockout mice lacking UT-B (see, e.g., Bankir et al., *Am J Physiol Renal Physiol* 286:F144-F151, 2004; Yang et al., *J Biol Chem* 277:10633-37, 2002) or various UT-A isoforms (see, e.g., Fenton et al., *Proc Natl Acad Sci U.S.A.* 101:7469-74, 2004; Fenton et al., *J Am Soc Nephrol* 16:1583-92, 2005; Uchida et al., *Mol Cell Biol* 25: 7357-63, 2005) has provided evidence for the involvement of UTs in the urinary concentrating mechanism, subject to the caveat that gene knockout may produce off-target effects such as compensatory changes in the expression of non-UT transport proteins (see, e.g., Fenton, *Curr Opin Nephrol Hypertens* 17:513-18, 2008; Klein et al., *J Am Soc Nephrol* 15:1161-67, 2004). Though UT function has been studied mainly in kidney, UTs are also expressed in erythrocytes, testis, brain, heart and urinary bladder (see, e.g., Doran et al., *Am J Physiol Regul Integr Comp Physiol* 290:R1446-R1459, 2006) where their physiological functions are not clear.

Phenotype analysis of mice separately lacking vasa recta UT-B or inner medullary collecting duct UT-A1/3 implicated UT involvement in the formation of concentrated urine and in renal urea clearance (see, e.g., Yang et al., *J. Biol. Chem.* 277:10633-37 (2002); Fenton et al., *Proc. Natl. Acad. Sci. USA* 101:7469-74 (2004); Fenton et al., *J. Am. Soc. Nephrol.* 16, 1583-92 (2005)). The UT-B knock-out mice that were generated manifested a urea-selective urinary concentrating defect associated with urinary hypoosmolality and increased renal urea clearance (Yang et al., supra). UT-B is also expressed outside of the kidney, most notably and in highest abundance in red blood cell (RBC) membranes. Loss-of-function human UT-B mutations result in greatly reduced urea permeability in RBC and a mild urinary concentrating defect (Sands et al., *J. Am. Soc. Nephrol.* 2:1689-96 (1992); Lucien et al., *J. Biol. Chem.* 273:12973-80 (1998)).

Diuretics are administered widely in humans to increase renal salt and water clearance in a variety of conditions that are associated with total body fluid overload, such as congestive heart failure and cirrhosis, as well in normovolemic states such as hypertension and syndrome of inappropriate secretion of antidiuretic hormone (SIADH). Most diuretics are inhibitors of salt absorption by kidney tubules, such as a furosemide block of $Na^+/K^+/2Cl^-$ co-transport in the thick ascending limb of Henle and a thiazide block of $Na^+/Cl^-$ co-transport in the distal tubule. Recently, a new type of diuretic, called an "aquaretic," has been developed to increase renal water clearance in hyponatremia associated with fluid overload or SIADH (see, e.g., Goldsmith, *Am. J. Cardiol.* 95:14B-23B (2005); Miller, *J. Am. Geriatr. Soc.* 54:345-53 (2006)). Vasopressin-2 receptor (V2R) antagonist aquaretics have been approved for clinical use in some countries, though not yet in the United States, and aquaporin inhibitor aquaretics are under development.

Functional studies in knock-out mice indicate a critical role for urea transporters (UTs) in the urinary concentrating mechanism and in renal urea clearance. However, potent and specific urea transport blockers have not been available. Accordingly, a third type of diuretic is needed: one that targets renal urea clearance mechanisms. Because urea is of at least equal importance to NaCl in the renal countercurrent mechanism for urinary concentration (see, e.g., Bankir et al., supra; Masilamani et al., In *The Kidney* (6th Edition), Brenner, ed. Philadelphia, Pa.; WB Saunders Company; pages 595-35; (2000)), such diuretics are needed for increasing solute clearance in states of fluid overload, hypertension, and may also be useful in prolonging dialysis-free survival in chronic renal insufficiency.

Urea transporter inhibitors identified to date have included non-selective membrane intercalating agents, urea analogs with insufficient potency, and specific urea transporter inhibitors with lower than desired potency. A need exists in the medical art for compounds that inhibit urea transporter and that exhibit nanomolar potency for increasing solute clearance and free water excretion in states of fluid overload, hypertension, and chronic renal insufficiency.

BRIEF SUMMARY

Provided herein are triazolothienopyrimidine compounds that inhibit the urea transport activity of urea transporters, such as urea transporter-B (UT-B), and thereby reduce urine concentration in a host receiving the compound. Compositions comprising these compounds and methods and uses for these compounds are also provided. Provided herein are the following embodiments.

Embodiment 1

A method for treating a disease or disorder treatable by inhibiting transport of urea in a subject, said method comprising administering to the subject a pharmaceutical composition comprising a pharmaceutically acceptable excipient and a compound of structure (I):

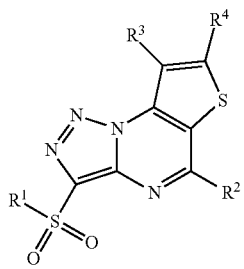

(I)

or a single stereoisomer, a mixture of stereoisomers, tautomer or pharmaceutically acceptable salt thereof, wherein,
$R^1$ is optionally substituted aryl or optionally substituted heteroaryl;
$R^2$ is $-N(R^5)(R^6)$;
$R^3$ and $R^4$ are each independently hydrogen, alkyl, halo or haloalkyl;
$R^5$ is hydrogen or alkyl; and
$R^6$ is optionally substituted alkyl, optionally substituted cycloalkyl, optionally substituted heterocyclylalkyl, optionally substituted aralkyl, or optionally substituted heteroarylalkyl; or
$R^5$ and $R^6$, together with the nitrogen atom to which they are attached, form an optionally substituted N-heterocycle, or optionally substituted N-heteroaryl.

Embodiment 2

The method of Embodiment 1 wherein $R^1$ is optionally substituted phenyl and the compound has a structure of structure (II):

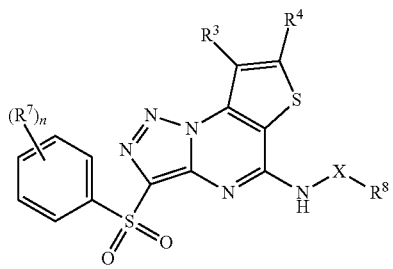

(II)

wherein,
n is 0, 1, 2 or 3;
X is an alkylene chain;
$R^3$ and $R^4$ are each independently hydrogen, alkyl, halo or haloalkyl;
$R^7$ is alkyl, halo, haloalkyl, or $-OR^9$;

$R^8$ is optionally substituted aryl, optionally substituted heteroaryl or optionally substituted heterocyclyl, or $-OR^9$; and
$R^9$ is hydrogen, alkyl or haloalkyl.

Embodiment 3

The method of Embodiment 2 wherein, n is 1 or 2; X is a $C_{1-5}$ alkylene chain; each $R^3$ and $R^4$ are independently hydrogen, alkyl, halo or haloalkyl; $R^7$ is alkyl, halo, haloalkyl, or $-OR^9$; $R^8$ is optionally substituted heteroaryl; and $R^9$ is hydrogen, alkyl or haloalkyl.

Embodiment 4

The method of Embodiment 3 wherein, n is 1 or 2; X is a $C_{1-3}$ alkylene chain; $R^3$ and $R^4$ are each hydrogen; $R^7$ is alkyl, halo, haloalkyl, or $-OR^9$; $R^8$ is optionally substituted thiophenyl; and $R^9$ is hydrogen, alkyl or haloalkyl.

Embodiment 5

The method of Embodiment 4 wherein, n is 1 or 2; X is $-(CH_2)-$; $R^3$ and $R^4$ are each hydrogen; $R^7$ is alkyl, halo, haloalkyl, or $-OR^9$; $R^8$ is optionally substituted thiophenyl; and $R^9$ is hydrogen, alkyl or haloalkyl.

Embodiment 6

The method of Embodiment 5 wherein, n is 1 or 2; X is $-(CH_2)-$; $R^3$ and $R^4$ are each hydrogen; $R^7$ is $-C(R^{10})(R^{11})-R^{12}$, $-OR^9$ or halo; $R^8$ is optionally substituted thiophenyl; $R^9$ is alkyl or haloalkyl; $R^{10}$ and $R^{11}$ are each independently halo or alkyl; and $R^{12}$ is alkyl, halo or haloalkyl.

Embodiment 7

The method of Embodiment 6 wherein the compound is
{3-[4-(1,1-difluoro-ethyl)-benzenesulfonyl]-thieno[2,3-e][1,2,3]triazolo[1,5-a]pyrimidin-5-yl}-thiophen-2-ylmethyl-amine;
thiophen-2-ylmethyl-[3-(4-trifluoromethyl-benzenesulfonyl)-thieno[2,3-e][1,2,3]triazolo[1,5-a]pyrimidin-5-yl]-amine;
thiophen-2-ylmethyl-[3-(4-trifluoromethoxy-benzenesulfonyl)-thieno[2,3-e][1,2,3]triazolo[1,5-a]pyrimidin-5-yl]-amine;
{3-[4-methoxy-benzenesulfonyl]-thieno[2,3-e][1,2,3]triazolo[1,5-a]pyrimidin-5-yl}-thiophen-2-ylmethyl-amine;
{3-[4-fluoro-benzenesulfonyl]-thieno[2,3-e][1,2,3]triazolo[1,5-a]pyrimidin-5-yl}-thiophen-2-ylmethyl-amine;
{3-[4-bromo-benzenesulfonyl]-thieno[2,3-e][1,2,3]triazolo[1,5-a]pyrimidin-5-yl}-thiophen-2-ylmethyl-amine;
{3-[4-chloro-benzenesulfonyl]-thieno[2,3-e][1,2,3]triazolo[1,5-a]pyrimidin-5-yl}-thiophen-2-ylmethyl-amine; or
{3-[3-chloro-benzenesulfonyl]-thieno[2,3-e][1,2,3]triazolo[1,5-a]pyrimidin-5-yl}-thiophen-2-ylmethyl-amine.

Embodiment 8

The method of Embodiment 5, wherein $R^7$ is alkyl.

Embodiment 9

The method of Embodiment 8, wherein the compound is
{3-[4-ethyl-benzenesulfonyl]-thieno[2,3-e][1,2,3]triazolo[1,5-a]pyrimidin-5-yl}-thiophen-2-ylmethyl-amine;
{3-[4-isopropyl-benzenesulfonyl]-thieno[2,3-e][1,2,3]triazolo[1,5-a]pyrimidin-5-yl}-thiophen-2-ylmethyl-amine; or
{3-[3,4-dimethyl-benzenesulfonyl]-thieno[2,3-e][1,2,3]triazolo[1,5-a]pyrimidin-5-yl}-thiophen-2-ylmethyl-amine.

Embodiment 10

The method of Embodiment 3 wherein, n is 1 or 2; X is a $C_{1-3}$ alkylene chain; $R^3$ and $R^4$ are each hydrogen; $R^7$ is alkyl, halo, haloalkyl, or —$OR^9$; $R^8$ is optionally substituted furanyl; and $R^9$ is hydrogen, alkyl or haloalkyl.

Embodiment 11

The method of Embodiment 10 wherein, n is 1 or 2; X is —($CH_2$)—; $R^3$ and $R^4$ are each hydrogen; $R^7$ is alkyl, halo, haloalkyl, or —$OR^9$; $R^8$ is optionally substituted furanyl; and $R^9$ is hydrogen, alkyl or haloalkyl.

Embodiment 12

The method of Embodiment 11, wherein the compound is
furan-2-ylmethyl-[3-(4-isopropyl-benzenesulfonyl)-thieno[2,3-e][1,2,3]triazolo[1,5-a]pyrimidin-5-yl]-amine;
furan-2-ylmethyl-[3-(4-methyl-benzenesulfonyl)-thieno[2,3-e][1,2,3]triazolo[1,5-a]pyrimidin-5-yl]-amine;
furan-2-ylmethyl-[3-(3,4-dimethyl-benzenesulfonyl)-thieno[2,3-e][1,2,3]triazolo[1,5-a]pyrimidin-5-yl]-amine;
furan-2-ylmethyl-[3-(4-chloro-benzenesulfonyl)-thieno[2,3-e][1,2,3]triazolo[1,5-a]pyrimidin-5-yl]-amine;
furan-2-ylmethyl-[3-(4-ethyl-benzenesulfonyl)-thieno[2,3-e][1,2,3]triazolo[1,5-a]pyrimidin-5-yl]-amine; or
furan-2-ylmethyl-[3-(2,5-dimethyl-benzenesulfonyl)-thieno[2,3-e][1,2,3]triazolo[1,5-a]pyrimidin-5-yl]-amine.

Embodiment 13

The method of Embodiment 2 wherein, n is 1 or 2; X is a $C_{1-3}$ alkylene chain; each $R^3$ and $R^4$ are independently hydrogen, alkyl, halo or haloalkyl; $R^7$ is alkyl, halo, haloalkyl, or —$OR^9$; $R^8$ is —$OR^9$; and $R^9$ is hydrogen, alkyl or haloalkyl.

Embodiment 14

The method of Embodiment 13 wherein the compound is
{3-benzenesulfonyl-thieno[2,3-e][1,2,3]triazolo[1,5-a]pyrimidin-5-yl}-3-methoxypropyl-amine;
{3-[4-methyl-benzenesulfonyl]-thieno[2,3-e][1,2,3]triazolo[1,5-a]pyrimidin-5-yl}-3-(1-methylethoxyl)propyl-amine;
{3-[4-methyl-benzenesulfonyl]-thieno[2,3-e][1,2,3]triazolo[1,5-a]pyrimidin-5-yl}-2-methoxyethyl-amine;
{3-[3,4-dimethyl-benzenesulfonyl]-thieno[2,3-e][1,2,3]triazolo[1,5-a]pyrimidin-5-yl}-3-ethoxylpropyl-amine;
{3-[3,4-dimethyl-benzenesulfonyl]-thieno[2,3-e][1,2,3]triazolo[1,5-a]pyrimidin-5-yl}-3-(1-methylethoxyl)propyl-amine;
{3-[3,4-dimethyl-benzenesulfonyl]-thieno[2,3-e][1,2,3]triazolo[1,5-a]pyrimidin-5-yl}-2-methoxyethyl-amine;
{3-[4-chloro-benzenesulfonyl]-thieno[2,3-e][1,2,3]triazolo[1,5-a]pyrimidin-5-yl}-2-methoxyethyl-amine;
{3-[4-chloro-benzenesulfonyl]-thieno[2,3-e][1,2,3]triazolo[1,5-a]pyrimidin-5-yl}-3-methoxypropyl-amine;
{3-[4-isopropyl-benzenesulfonyl]-thieno[2,3-e][1,2,3]triazolo[1,5-a]pyrimidin-5-yl}-3-ethoxylpropyl-amine;
{3-[4-isopropyl-benzenesulfonyl]-thieno[2,3-e][1,2,3]triazolo[1,5-a]pyrimidin-5-yl}-2-methoxyethyl-amine;
{3-[4-ethyl-benzenesulfonyl]-thieno[2,3-e][1,2,3]triazolo[1,5-a]pyrimidin-5-yl}-2-methoxyethyl-amine;
{3-[4-ethyl-benzenesulfonyl]-thieno[2,3-e][1,2,3]triazolo[1,5-a]pyrimidin-5-yl}-3-methoxypropyl-amine;
{3-[4-ethyl-benzenesulfonyl]-thieno[2,3-e][1,2,3]triazolo[1,5-a]pyrimidin-5-yl}-3-(1-methylethoxyl)propyl-amine;
{3-[2,5-dimethyl-benzenesulfonyl]-thieno[2,3-e][1,2,3]triazolo[1,5-a]pyrimidin-5-yl}-3-ethoxypropyl-amine;
{3-[2,5-dimethyl-benzenesulfonyl]-thieno[2,3-e][1,2,3]triazolo[1,5-a]pyrimidin-5-yl}-3-(1-methylethoxyl)propyl-amine;
{3-[2,5-dimethyl-benzenesulfonyl]-thieno[2,3-e][1,2,3]triazolo[1,5-a]pyrimidin-5-yl}-2-methoxyethyl-amine; or
{3-[2,5-dimethyl-benzenesulfonyl]-thieno[2,3-e][1,2,3]triazolo[1,5-a]pyrimidin-5-yl}-3-methoxypropyl-amine.

Embodiment 15

The method of Embodiment 2 wherein, n is 1 or 2; X is a $C_{1-2}$ alkylene chain; each $R^3$ and $R^4$ is independently hydrogen, alkyl, halo or haloalkyl; $R^7$ is alkyl, halo, haloalkyl, or —$OR^9$; $R^8$ is optionally substituted aryl; and $R^9$ is hydrogen, alkyl or haloalkyl.

Embodiment 16

The method of Embodiment 15 wherein the compound is
[3-(4-isopropyl-benzenesulfonyl)-thieno[2,3-e][1,2,3]triazolo[1,5-a]pyrimidin-5-yl]-(4-methoxy-benzyl)-amine;
[3-(4-isopropyl-benzenesulfonyl)-thieno[2,3-e][1,2,3]triazolo[1,5-a]pyrimidin-5-yl]-naphthalen-1-ylmethyl-amine;
[3-(4-methyl-benzenesulfonyl)-thieno[2,3-e][1,2,3]triazolo[1,5-a]pyrimidin-5-yl]-(4-methoxy-benzyl)-amine;
[3-(4-methyl-benzenesulfonyl)-thieno[2,3-e][1,2,3]triazolo[1,5-a]pyrimidin-5-yl]-(1-phenyl-1-methyl)methyl-amine;
[3-(4-methyl-benzenesulfonyl)-thieno[2,3-e][1,2,3]triazolo[1,5-a]pyrimidin-5-yl]-(3-methoxy-benzyl)-amine;
[3-(4-methyl-benzenesulfonyl)-thieno[2,3-e][1,2,3]triazolo[1,5-a]pyrimidin-5-yl]-(4-fluoro-benzyl)-amine;
[3-(3,4-dimethyl-benzenesulfonyl)-thieno[2,3-e][1,2,3]triazolo[1,5-a]pyrimidin-5-yl]-benzyl-amine;
[3-(3,4-dimethyl-benzenesulfonyl)-thieno[2,3-e][1,2,3]triazolo[1,5-a]pyrimidin-5-yl]-(2-chloro-benzyl)-amine;
[3-(3,4-dimethyl-benzenesulfonyl)-thieno[2,3-e][1,2,3]triazolo[1,5-a]pyrimidin-5-yl]-(2-methoxy-benzyl)-amine;
[3-(3,4-dimethyl-benzenesulfonyl)-thieno[2,3-e][1,2,3]triazolo[1,5-a]pyrimidin-5-yl]-(4-methoxy-benzyl)-amine;
[3-(3,4-dimethyl-benzenesulfonyl)-thieno[2,3-e][1,2,3]triazolo[1,5-a]pyrimidin-5-yl]-(3-methoxy-benzyl)-amine;
[3-(3,4-dimethyl-benzenesulfonyl)-thieno[2,3-e][1,2,3]triazolo[1,5-a]pyrimidin-5-yl]-(4-chloro-benzyl)-amine;
[3-(3,4-dimethyl-benzenesulfonyl)-thieno[2,3-e][1,2,3]triazolo[1,5-a]pyrimidin-5-yl]-(4-fluoro-benzyl)-amine;
[3-(4-ethyl-benzenesulfonyl)-thieno[2,3-e][1,2,3]triazolo[1,5-a]pyrimidin-5-yl]-benzyl-amine;
[3-(4-ethyl-benzenesulfonyl)-thieno[2,3-e][1,2,3]triazolo[1,5-a]pyrimidin-5-yl]-(4-chloro-benzyl)-amine;
[3-(4-ethyl-benzenesulfonyl)-thieno[2,3-e][1,2,3]triazolo[1,5-a]pyrimidin-5-yl]-(1-phenyl-1-methyl)methyl-amine;
[3-(4-ethyl-benzenesulfonyl)-thieno[2,3-e][1,2,3]triazolo[1,5-a]pyrimidin-5-yl]-(3-methoxy-benzyl)-amine;
[3-(4-ethyl-benzenesulfonyl)-thieno[2,3-e][1,2,3]triazolo[1,5-a]pyrimidin-5-yl]-(4-fluoro-benzyl)-amine;
[3-(2,5-dimethyl-benzenesulfonyl)-thieno[2,3-e][1,2,3]triazolo[1,5-a]pyrimidin-5-yl]-(1-phenyl-1-methyl)methyl-amine;
[3-(2,5-dimethyl-benzenesulfonyl)-thieno[2,3-e][1,2,3]triazolo[1,5-a]pyrimidin-5-yl]-(4-fluoro-benzyl)-amine; or

[3-(2,5-dimethyl-benzenesulfonyl)-thieno[2,3-e][1,2,3]tria-zolo[1,5-a]pyrimidin-5-yl]-benzyl-amine.

Embodiment 17

The method of Embodiment 2 wherein, n is 1 or 2; X is a $C_{1-2}$ alkylene chain; each $R^3$ and $R^4$ is independently hydrogen, alkyl, halo or haloalkyl; $R^7$ is alkyl, halo, haloalkyl, or —$OR^9$; $R^8$ is optionally substituted heterocyclyl; and $R^9$ is hydrogen, alkyl or haloalkyl.

Embodiment 18

The method of Embodiment 17 wherein $R^8$ is tetrahydrofuranyl.

Embodiment 19

The method of Embodiment 18 wherein the compound is
tetrahydrofuran-2-ylmethyl-[3-(4-methyl-benzenesulfonyl)-thieno[2,3-e][1,2,3]triazolo[1,5-a]pyrimidin-5-yl]-amine;
tetrahydrofuran-2-ylmethyl-[3-(4-isopropyl-benzenesulfonyl)-thieno[2,3-e][1,2,3]triazolo[1,5-a]pyrimidin-5-yl]-amine; or
tetrahydrofuran-2-ylmethyl-[3-(4-ethyl-benzenesulfonyl)-thieno[2,3-e][1,2,3]triazolo[1,5-a]pyrimidin-5-yl]-amine.

Embodiment 20

The method of Embodiment 1 wherein $R^1$ is optionally substituted heteroaryl; $R^2$ is —$N(R^5)(R^6)$; each $R^3$ and $R^4$ is independently hydrogen, alkyl, halo or haloalkyl; $R^5$ is hydrogen or alkyl; and $R^6$ is optionally substituted alkyl, optionally substituted cycloalkyl, optionally substituted heterocyclylalkyl, optionally substituted aralkyl, or optionally substituted heteroarylalkyl.

Embodiment 21

The method of Embodiment 20 wherein $R^1$ is optionally substituted heteroaryl; $R^2$ is —$N(R^5)(R^6)$; each $R^3$ and $R^4$ is independently hydrogen, alkyl, halo or haloalkyl; $R^5$ is hydrogen or alkyl; and $R^6$ is optionally substituted heteroarylalkyl.

Embodiment 22

The method of Embodiment 21 wherein $R^1$ is optionally substituted thiophenyl; $R^2$ is —$N(R^5)(R^6)$; each $R^3$ and $R^4$ are independently hydrogen, alkyl, halo or haloalkyl; $R^5$ is hydrogen or alkyl; and $R^6$ is optionally substituted thiophenyl.

Embodiment 23

The method of Embodiment 22 wherein the compound is [3-(thiophene-2-sulfonyl)-thieno[2,3-e][1,2,3]triazolo[1,5-a]pyrimidin-5-yl]-thiophen-2-ylmethyl-amine.

Embodiment 24

The method of any one of Embodiments 1-23, wherein the disease or disorder treatable by inhibiting transport of urea is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

Embodiment 25

The method of Embodiment 24, wherein transport of urea by the UT-B transporter is inhibited.

Embodiment 26

A compound of structure (III):

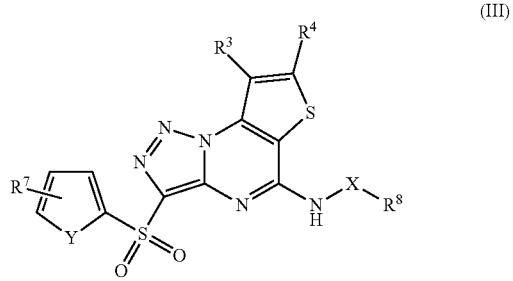

or a single stereoisomer, a mixture of stereoisomers, tautomer or pharmaceutically acceptable salt thereof, wherein,
X is an alkylene chain;
Y is —CH=$CH_2$—, —CH=N—, S, or O;
each $R^3$ and $R^4$ is independently hydrogen, alkyl, halo or haloalkyl;
$R^7$ is —$C(R^{10})(R^{11})$—$R^{12}$, —$OR^9$ or halo;
$R^8$ is optionally substituted aryl, optionally substituted heteroaryl or optionally substituted heterocyclyl, or —$OR^9$;
$R^9$ is alkyl or haloalkyl;
$R^{10}$ and $R^{11}$ are each independently halo or alkyl; and
$R^{12}$ is alkyl, halo or haloalkyl,
wherein when Y is —CH=$CH_2$— and $R^7$ is isopropyl at the position para to the linking carbon, $R^8$ is not furanyl or thiophenyl, and when Y is —CH=$CH_2$— and $R^7$ is Br at the position para to the linking carbon, $R^8$ is not thiophenyl.

Embodiment 27

The compound of Embodiment 26 wherein, Y is —CH=$CH_2$—; and $R^8$ is optionally substituted heteroaryl.

Embodiment 28

The compound of Embodiment 27 wherein $R^8$ is optionally substituted thiophenyl.

Embodiment 29

The compound of Embodiment 28, wherein the compound is 3-[4-(1,1-difluoro-ethyl)-benzenesulfonyl]-thieno[2,3-e][1,2,3]triazolo[1,5-a]pyrimidin-5-yl}-thiophen-2-ylmethyl-amine;
thiophen-2-ylmethyl-[3-(4-trifluoromethyl-benzenesulfonyl)-thieno[2,3-e][1,2,3]triazolo[1,5-a]pyrimidin-5-yl]-amine;
thiophen-2-ylmethyl-[3-(4-trifluoromethoxy-benzenesulfonyl)-thieno[2,3-e][1,2,3]triazolo[1,5-a]pyrimidin-5-yl]-amine;
3-[4-methoxy-benzenesulfonyl]-thieno[2,3-e][1,2,3]triazolo[1,5-a]pyrimidin-5-yl}-thiophen-2-ylmethyl-amine; or 3-[4-fluoro-benzenesulfonyl]-thieno[2,3-e][1,2,3]triazolo[1,5-a]pyrimidin-5-yl}-thiophen-2-ylmethyl-amine.

Embodiment 30

The compound of Embodiment 26 wherein, Y is S; and $R^8$ is optionally substituted heteroaryl.

Embodiment 31

The compound of Embodiment 30 wherein $R^8$ is optionally substituted thiophenyl.

Embodiment 32

The compound of Embodiment 31, wherein the compound is [3-(thiophene-2-sulfonyl)-thieno[2,3-e][1,2,3]triazolo[1,5-a]pyrimidin-5-yl]-thiophen-2-ylmethyl-amine.

Embodiment 33

A pharmaceutical composition comprising the compound of any one of Embodiments 26-32 and a pharmaceutically acceptable excipient.

Embodiment 34

A method for treating a disease or disorder treatable by inhibiting transport of urea in a subject, the method comprising administering to the subject the pharmaceutical composition of Embodiment 33.

Embodiment 35

The method of Embodiment 34, wherein the disease or disorder is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

In other embodiments, provided herein is a use of a compound of any one of structures (I), (II), and (III) as described above and herein for the manufacture of a medicament for treating a disease or disorder treatable by inhibiting transport of urea, wherein the disease or disorder is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

In still another embodiment, provided herein is a compound of any one of structures (I), (II), and (III) as described above and herein for use in treating a disease or disorder treatable by inhibiting transport of urea, wherein the disease or disorder is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

In still another embodiment, use of a compound of any one of structures (I), (II), and (III) as described above and herein is provided herein for treating a disease or disorder treatable by inhibiting transport of urea, wherein the disease or disorder is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

Also provided herein in another embodiment, is a method for inhibiting transport of urea across a cell membrane comprising contacting a cell comprising a urea transporter and a compound having any one of structures (I), (II), and (III) as described above and herein.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims that follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise.

When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise.

BRIEF DESCRIPTION OF THE DRAWINGS

FIG. 1A provides a schematic of the screening assay (left) and shows rapid dilution of acetamide-loaded mouse erythrocytes in acetamide-free phosphate-buffer saline (PBS), resulting in osmotic cell swelling following UT-B-facilitated acetamide efflux and consequent cell shrinking (right). UT-B inhibition allows unopposed cell swelling and causes erythrocyte lysis. FIG. 1B illustrates structures of UT-B inhibitors. The compound $UTB_{inh}$-14 is also referred to herein as compound 1 (see, e.g., FIG. 8D). FIG. 1C describes $UTB_{inh}$-14 synthesis. Reagents and conditions: (a) $NaN_3$ (3 eq), DMSO, 85° C., 10 h; (b) $NaClO_2$ (2.1 eq), sulfamic acid (1.5 eq); (c) 1-bromo-2-methylpropane (1.2 eq), $Cs_2CO_3$ (0.7 eq), DMF; (d) NaOEt, EtOH, 30 min, rt; (e) thiophene-2-methylamine, PyBOP, DMF, 30 min, MW, 85° C.

FIG. 2A illustrates results from stopped-flow light scattering assay of UT-B urea transport. Erythrocytes suspended in PBS were mixed rapidly with a urea-containing solution to give a 100 mM inwardly directly urea gradient. The kinetics of light scattering are shown, with urea influx responsible for the phase of decreasing scattering light intensity. Indicated concentrations of $UTB_{inh}$-14 were present in both erythrocyte- and urea-containing solutions. Bottom two curves show urea transport in erythrocytes from UT-B knockout mice. FIG. 2B illustrates concentration-inhibition data showing percentage inhibition (S.E., n=3-5) with fitted $IC_{50}$ (single-site binding model) of 25.1 and 10.3 for mouse and human UT-B, respectively.

FIG. 3A: Reversibility. Mouse erythrocytes were incubated with 100 nM $UTB_{inh}$-14 for 10 min, followed by washout. Urea influx assayed as in FIG. 2A in untreated erythrocytes, and before vs. after $UTB_{inh}$-14 washout as indicated (S.E., n=3, P<0.01). FIG. 3B: $UTB_{inh}$-14 sidedness (site-of-action). $UTB_{inh}$-14 (100 nM) was present in erythrocyte-containing or urea-containing solutions, or both, and urea transport assayed as in A (S.E., n=3, P<0.01). FIG. 3C: Urea competition. Urea influx measured as a function of urea gradient, in the absence and presence of 50 nM $UTB_{inh}$-14 in the erythrocyte- and urea-containing solutions (S.E., n=3-5). Inset shows computed percentage inhibition. FIG. 3D: Transport symmetry. Urea efflux measured in erythrocytes pre-loaded with urea (100 mM) for 30 min, and mixed in the stopped-flow apparatus with (urea-free) PBS. $UTB_{inh}$-14 was present in both solutions. Concentration-inhibition data (S.E., n=3-5) gave $IC_{50}$ of 26.7 nM.

FIG. 4A presents the computed site of $UTB_{inh}$-14 binding at the cytoplasmic surface of the UT-B protein. $UTB_{inh}$-14 is shown in stick format. For reference, the computed site of methylurea (a urea analog) is shown, based on modeling done for a bacterial urea transporter (Levin et al., Nature 462:757-61, 2009). FIG. 4B presents a zoomed-in view of $UTB_{inh}$-14 bound in a groove at the UT-B channel region. FIG. 4C indicates the interactions of $UTB_{inh}$-14 (see compound structure in FIG. 1B) with specific amino acid residues at the tentative UT-B binding site.

FIG. 5A: Transepithelial urea transport was measured in MDCK cells stably expressing UT-A1, UT-A3, and UT-B. Kinetics of transepithelial urea transport across monolayers of UT-A1-, UT-A3, and UT-B expressing MDCK cells (S.E., n=4). Where indicated, forskolin (10 μM), $UTB_{inh}$-14 (10 μM) or phloretin (100 μM) were present. FIG. 5B: AQP1 water transport. Osmotic water permeability measured in wildtype (left) and AQP1-null erythrocytes (right) in response to a 100-mM inwardly directed gradient sucrose gradient at 10° C. FIG. 5C: CFTR and calcium-activated chloride channels. Short circuit current was measured in T84 cells. (left) CFTR was activated by 10 μM forskolin, with 1 and 10 μM $UTB_{inh}$-14 added as indicated (solid curve; dashed curve, no inhibitor added). CFTR chloride current was blocked by 20 μM $CFTR_{inh}$-172. CFTR was inhibited by pretreatment with 20 μM $CFTR_{inh}$-172. (right) TMEM16A chloride current was activated by 100 μM ATP. $UTB_{inh}$-14 was added as indicated. ATP-induced current was blocked by 100 μM tannic acid. FIG. 5D: MTT cytotoxicity assay. MDCK cells were incubated with indicated concentrations of $UTB_{inh}$-14 for 24 h (S.E., n=4). DMSO and phenol toxicity controls shown.

FIG. 6A: Kidney. (left) LC/MS assay of $UTB_{inh}$-14 in kidney homogenate. Known amounts of $UTB_{inh}$-14 were added to kidney homogenate prior to assay, which included steps of organic extraction, concentration, and LC/MS assay. $UTB_{inh}$-14 ion chromatograms ([M+H]$^+$, m/z=456) are shown. Inset shows linear assay response (integrated ion current vs. [$UTB_{inh}$-14], S.E., n=3). (right) $UTB_{inh}$-14 in mouse kidney following a single intraperitoneal dose of 300 μg $UTB_{inh}$-14, showing ion chromatograms at indicated times after $UTB_{inh}$-14 administration. The time course of kidney-associated $UTB_{inh}$-14 (μg/g wet kidney) is shown (S.E., 3 mice). FIG. 6B and FIG. 6C present similar analyses in blood and urine. $UTB_{inh}$-14 extracted from blood and urine and analyzed by LC/MS (see description of FIG. 6A). Ion chromatograms and assay responses at the left for known amounts of $UTB_{inh}$-14 added to blood or urine. Ion chromatograms and time courses at the right for indicated times after $UTB_{inh}$-14 administration.

FIG. 7A. Urine osmolality in wild type mice (mean±S.E., 6 mice per group, *P<0.01). Mice received dDAVP (1 μg/kg, intraperitoneal) where indicated. FIG. 7B. Urine osmolality and urea concentration in wild type mice following dDAVP (1 μg/kg) and $UTB_{inh}$-14 (300 μg) (or vehicle) (mean±S.E., 6 mice per group, *P<0.01). The inset shows urine volume in 4 h urine collections without or with $UTB_{inh}$-14 (mean±S.E., 5 mice per group). FIG. 7C. Same protocol as in B, but in UT-B knockout mice (mean±S.E., 5 mice per group). FIG. 7D. Urine collected from mice given free access to food and water (no dDAVP) without or after administration of $UTB_{inh}$-14 (300 μg) (mean±S.E., 5 mice per group, *P<0.05). FIG. 7E. Mice were placed on indicated low, normal or high-protein diets for 1 wk prior to 4 h urine collections without or after administration of $UTB_{inh}$-14 (300 μg) (mean±S.E., 5 mice per group, *P<0.05).

FIG. 8A. Concentration-inhibition data from erythrocyte lysis assay for indicated compounds (S.E., n=3). FIG. 8B. In vitro metabolic stability data shown as kinetics of disappearance of indicated parent compounds following incubation with hepatic microsomes and NADPH. FIG. 8C. LC/MS traces showing disappearance of 1 and appearance of metabolites at m/z=472 and 488. FIG. 8D. Structure of 1 showing putative sites causing poor metabolic stability. Compound 1 is also referred to herein as $UTB_{inh}$-14 (see, e.g., FIG. 1B).

FIG. 10A. Stopped-flow light scattering measurement of urea permeability in mouse erythrocytes. Erythrocyte suspensions were mixed with an equal volume of urea-containing solution to give a 100-mM inwardly directly urea gradient. Inward urea flux is seen as decreasing scattered light intensity. Erythrocytes were incubated with indicated concentrations of 3k for 10 min prior to measurements. FIG. 10B. Concentration-inhibition data for mouse (top) and human (bottom) erythrocytes (S.E., n=3). Fitted $IC_{50}$ were 23 nM (mouse) and 15 nM (human). FIG. 10C. In vitro metabolic stability in hepatic microsomes. (left) LC/MS showing kinetics of disappearance of 3k. (right) Kinetics of 3k disappearance, with data for 1 shown for comparison (S.E., n=3).

FIG. 11A. LC/MS analysis of 3k concentration in blood. Standards shown at the left and inset. Original LC/MS traces and deduced 3k concentrations in blood, following intraperitoneal bolus administration of 400 μg 3k (S.E., 3 mice per group). FIG. 11B. Concentrations of 3k in kidney and urine for mice studied in A. FIG. 11C. Concentrations of 3k and 1 in blood at 6 h after intraperitoneal administration of 200 μg 3k and 200 μg 1 (S.E., 3 mice). FIG. 11D. Urine osmolality in mice after intraperitoneal administration of 400 μg 3k or formulation alone followed 1 h later by dDAVP (S.E., 4 mice, *P<0.01).

DETAILED DESCRIPTION

Figure 1:
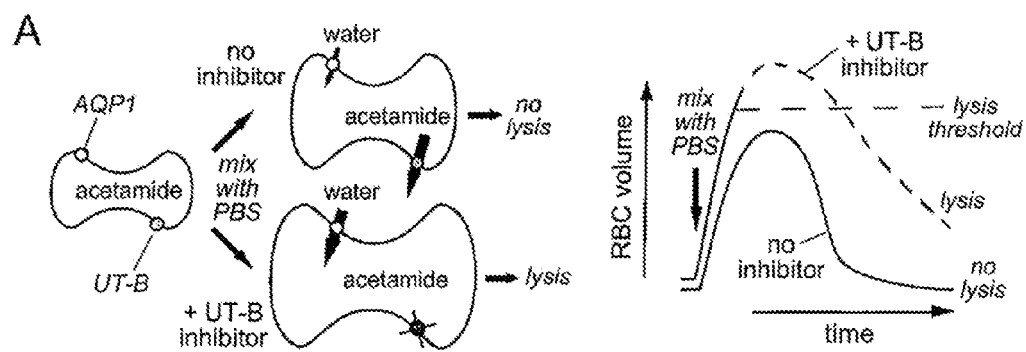
FIGS. 1A-1C describe identification and synthesis of triazlothienopyrimidine UT-B inhibitors.
Figure 1:
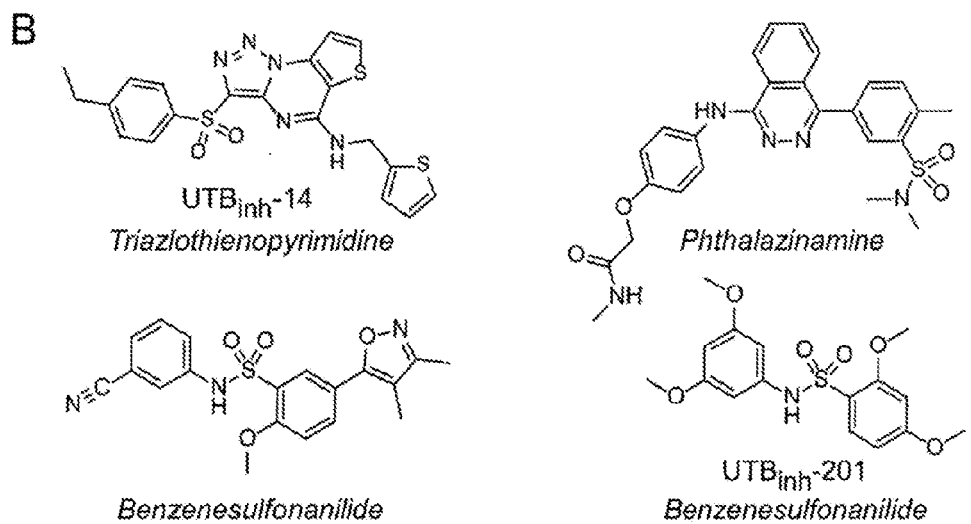
Figure 1:
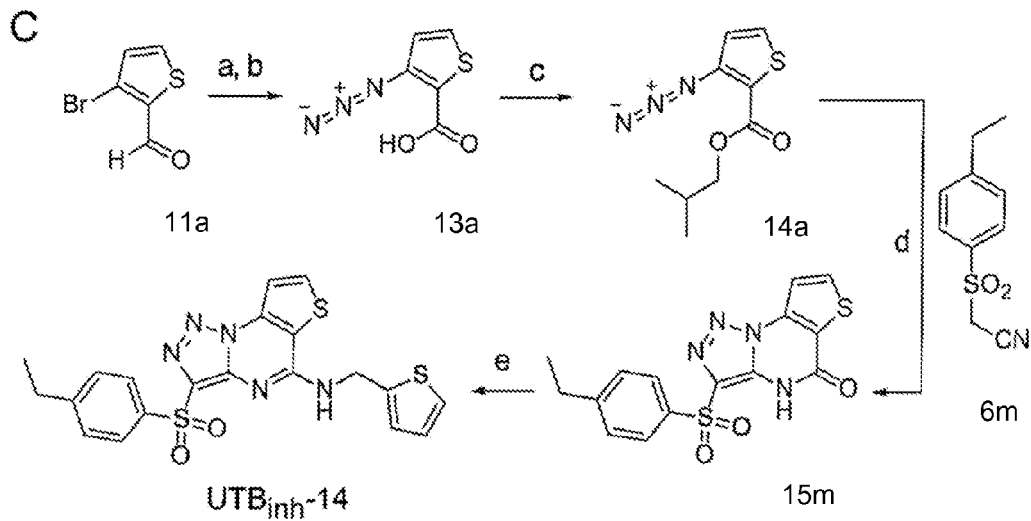

As stated above, provided herein are compounds, compositions, and methods for treatment of one or more diseases or disorders treatable by inhibiting transport of a neutrally charged solute, such as urea, across a cell membrane by a urea transporter (UT). The triazolothienopyrimidine compounds described herein are more potent UT inhibitors than compounds previously described and also exhibit improved metabolic stability.

Diseases, disorders, or conditions that may be treated according to the methods described herein may be associated with a fluid retention imbalance, such as urea clearance insufficiency. Potent, specific, small molecule inhibitors of urea transporters (UTs) are described herein that may be used to treat diseases, disorders, or conditions including but not limited to a refractory edema associated with or caused by a cardiovascular, renal, or metabolic disease, disorder, or condition, such as cirrhosis, nephritic syndrome, acute renal failure, chronic renal insufficiency, hypertension, and congestive heart failure. In certain other embodiments, the disease, disorder, or condition to be treated is syndrome of inappropriate antidiuretic hormone secretion (SIADH), azotemia, fluid retention, and abnormal uresis. In other certain embodiments, at least one of the triazolothienopyrimidines compounds described herein may also be used in combination with a loop diuretic.

Defective urinary concentrating function in UT knockout mice suggests the potential utility of UT inhibitors as 'ureareatics' that would impair urinary concentrating function by a mechanism different from that of salt-transport blocking diuretics such as furosemide, or aquaretics such as $V_2$-receptor antagonists. As found in mice, humans lacking UT-B manifest a modest urinary concentrating defect (see, e.g., Lucien et al., *J. Biol. Chem.* 273:12973-80 (1998); Sands et al., *J. Am. Soc. Nephrol.* 2:1689-96 (1992)), supporting the potential ureareatic efficacy of UT-B inhibitors. Previously available UT inhibitors included compounds that are nonspecific and exhibit moderate or low activity such as the nonspecific membrane intercalating agent phloretin (exhibiting activity at >0.5 mM); urea analogs such as thiourea, methylurea, and dimethylurea (exhibiting activity at 50-100 mM); (see, e.g., Mayrand et al., supra), and chemically modified urea analogs (exhibiting irreversible activity at 30-100 μM) (Martial et al., *Pflügers Arch.* 423:51-58 (1993)). By high-throughput screening of 50,000 compounds, phenylsulfoxyoxozole inhibitors of human UT-B were identified that exhibited $IC_{50}$ of less than 100 nM (see, e.g., International Patent Application Publication No. WO 08/061248; U.S. Patent Application Publication No. US-2010-0305105; Levin et al., *FASEB J* 21:551-63, 2007). The triazolothienopyrimidine compounds described herein are more potent UT inhibitors than the phenylsulfoxyoxozole inhibitors, and the triazolothienopyrimidine compounds also exhibit improved metabolic stability.

The following triazolothienopyrimidine compounds and pharmaceutical compositions comprising these compounds that are urea transporter inhibitors may be useful for treating diseases, disorders, and conditions treatable by inhibiting UT (e.g., UT-B) transport of urea.

In one embodiment, provided herein is a compound of structure (I):

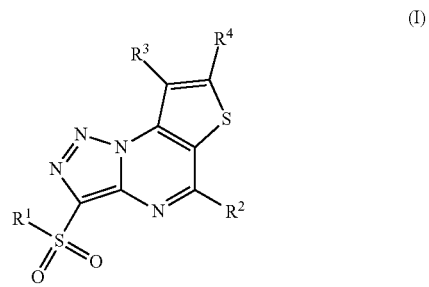

or a single stereoisomer, a mixture of stereoisomers, tautomer or pharmaceutically acceptable salt thereof, wherein, $R^1$ is optionally substituted aryl or optionally substituted heteroaryl;

$R^2$ is $-N(R^5)(R^6)$;

$R^3$ and $R^4$ are each independently hydrogen, alkyl, halo or haloalkyl;

$R^5$ is hydrogen or alkyl; and $R^6$ is optionally substituted alkyl, optionally substituted cycloalkyl, optionally substituted heterocyclylalkyl, optionally substituted aralkyl, or optionally substituted heteroarylalkyl; or $R^5$ and $R^6$, together with the nitrogen atom to which they are attached, form an optionally substituted N-heterocycle, or optionally substituted N-heteroaryl.

In certain embodiments, with respect to compounds of structure (I), $R^1$ is optionally substituted aryl, for example, optionally substituted phenyl. In certain specific embodiments, phenyl is unsubstituted. In other certain embodiments, phenyl is substituted with one or more of alkyl (e.g., $C_1$-$C_3$ alkyl or $C_1$-$C_6$ alkyl), halo, haloalkyl, or —$OR^9$ wherein $R^9$ is hydrogen, alkyl (e.g., $C_1$-$C_6$ alkyl) or haloalkyl (e.g., $C_1$-$C_6$ haloalkyl). In certain embodiments, $R^9$ is $C_1$-$C_3$ alkyl or $C_1$-$C_3$ haloalkyl. In particular embodiments, haloalkyl (e.g., $C_1$-$C_3$ haloalkyl) is a fluoroalkyl. In another embodiment, $R^1$ is a optionally substituted heteroaryl, which in certain specific embodiments may be a 5- or 6-membered heteroaryl that comprises at least one heteroatom wherein the heteroatom is S. In a specific embodiment, $R^1$ is an optionally substituted thiophenyl. In particular embodiments, when aryl or heteroaryl is substituted with at least one alkyl, alkyl is $C_1$-$C_3$ alkyl (e.g., —$CH_3$, —$CH_2CH_3$, —$CH_2(CH_3)_2$). In certain embodiments, when aryl or heteroaryl is substituted with at least one halo, halo is Cl, Br, or F. In other certain embodiments, when aryl or heteroaryl is substituted with one or more haloalkyl, haloalkyl is $C_1$-$C_3$ haloalkyl.

In certain embodiments with respect to compounds of structure (I), at least one of $R^3$ and $R^4$ is hydrogen (H). In particular embodiments, $R^3$ and $R^4$ are each hydrogen. In other particular embodiments, $R^3$ and $R^4$ are each independently hydrogen, $C_1$-$C_3$ alkyl, halo, or $C_1$-$C_3$ haloalkyl.

In other particular embodiments of compounds of structure (I), $R^5$ is hydrogen. In yet other particular embodiments, $R^5$ is alkyl, for example, methyl or ethyl.

In certain embodiments of compounds of structure (I), $R^6$ is optionally substituted alkyl (e.g., $C_1$-$C_6$ alkyl). In particular embodiments, $R^6$ is optionally substituted $C_1$-$C_3$ alkyl. In other certain embodiments, $R^6$ is optionally substituted cycloalkyl. In other embodiments, $R^6$ is optionally substituted heterocyclylalkyl, wherein the hetero atom is O, N, or S. In particular embodiments, $R^6$ is optionally substituted aralkyl, for example, optionally substituted phenylalkyl or naphthylalkyl. In still other embodiments, $R^6$ is optionally substituted heteroarylalkyl, wherein the heteroatom is S, O, or N. In a more particular embodiment, $R^6$ is optionally substituted 5- or 6-membered heteroarylalkyl, wherein the heteroatom is S or O.

In certain embodiments, $R^1$ is optionally substituted phenyl and the compound has a structure of structure (II):

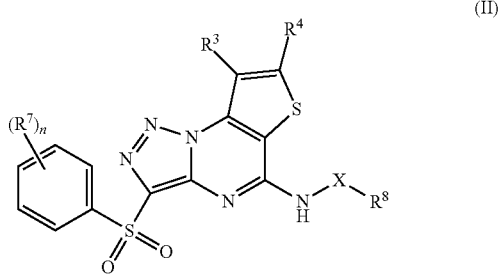

(II)

wherein,
n is 0, 1, 2 or 3; X is an alkylene chain; $R^3$ and $R^4$ are each independently hydrogen, alkyl, halo or haloalkyl; $R^7$ is alkyl, halo, haloalkyl, or —$OR^9$; $R^8$ is optionally substituted aryl, optionally substituted heteroaryl or optionally substituted heterocyclyl, or —$OR^9$; and $R^9$ is hydrogen, alkyl or haloalkyl.

In certain embodiments, X is a $C_{1-5}$ alkylene chain or a $C_{1-3}$ alkylene chain.

In certain embodiments, at least one of $R^3$ and $R^4$ is hydrogen (H). In particular embodiments, $R^3$ and $R^4$ are each hydrogen. In other particular embodiments, $R^3$ and $R^4$ are each independently hydrogen, $C_1$-$C_3$ alkyl, halo or $C_1$-$C_3$ halo alkyl.

In yet other specific embodiments with respect to compounds of structure (II), n is 1 or 2 and each $R^7$ is independently alkyl, halo, haloalkyl, or —$OR^9$. In particular embodiments, when at least one $R^7$ is alkyl, alkyl may be $C_1$-$C_6$ alkyl or $C_1$-$C_3$ alkyl (e.g., —$CH_3$, —$CH_2CH_3$, —$CH_2(CH_3)_2$). In other particular embodiments, when at least one $R^7$ is haloalkyl, haloalkyl may be $C_1$-$C_3$ haloalkyl and halo is F, Cl, or Br (e.g., fluoroalkyl, chloroalkyl, or bromoalkyl). In particular embodiments, when at least one $R^7$ is haloalkyl, haloalkyl is fluoroalkyl. In other particular embodiments, when at least one $R^7$ is halo, halo is F, Cl, or Br. In other certain embodiments, $R^9$ is H, or $C_1$-$C_3$ alkyl (e.g., —$CH_3$, —$CH_2CH_3$, —$CH_2(CH_3)_2$) or $C_1$-$C_3$ haloalkyl, which in particular embodiments, is a fluoroalkyl. In other particular embodiments, $R^7$ is —$C(R^{10})(R^{11})$—$R^{12}$, —$OR^9$ or halo, wherein $R^9$ is alkyl or haloalkyl; wherein $R^{10}$ and $R^{11}$ are each halo or alkyl (i.e., $R^{10}$ and $R^{11}$ are each independently halo or alkyl); and wherein $R^{12}$ is alkyl, halo or haloalkyl.

In particular embodiments, $R^8$ is optionally substituted aryl, for example, optionally substituted phenyl or optionally substituted naphthyl. In particular embodiments, naphthyl is unsubstituted. In certain particular embodiments, phenyl is unsubstituted. In other particular embodiments, phenyl may be substituted with $C_1$-$C_3$ alkyl (e.g., —$CH_3$, —$CH_2CH_3$, —$CH_2(CH_3)_2$); alkoxy (e.g., methoxy); or halo (e.g., F, Br, or Cl). In other particular embodiments, $R^8$ is optionally substituted heteroaryl and the heteroatom is S or O. In certain particular embodiments, $R^8$ is heteroaryl such as optionally substituted thiophenyl or optionally substituted furanyl. In other certain particular embodiments, $R^8$ is heteroaryl, for example, unsubstituted thiophenyl or unsubstituted furanyl. In other particular embodiments, $R^8$ is optionally substituted heterocyclyl wherein the heteroatom is O (e.g., tetrahydrofuranyl) or S. In still other embodiments, $R^8$ is —$OR^9$, and $R^9$ is hydrogen, alkyl (e.g., $C_1$-$C_3$ alkyl (for example, —$CH_3$, —$CH_2CH_3$, —$CH_2(CH_3)_2$)); or haloalkyl (e.g., $C_1$-$C_3$ haloalkyl) and halo is F, Br, or Cl (e.g., fluroalkyl, chloroalkyl, or bromoalkyl).

In certain embodiments of structure (II), n is 1 or 2; X is a $C_{1-5}$ alkylene chain; each $R^3$ and $R^4$ is independently hydrogen, alkyl, halo or haloalkyl; $R^7$ is alkyl, halo, haloalkyl, or —$OR^9$; $R^8$ is optionally substituted heteroaryl; and $R^9$ is hydrogen, alkyl or haloalkyl.

In another embodiment of structure (II), n is 1 or 2; X is a $C_{1-3}$ alkylene chain; $R^3$ and $R^4$ are each hydrogen; $R^7$ is alkyl, halo, haloalkyl, or —$OR^9$; $R^8$ is optionally substituted thiophenyl; and $R^9$ is hydrogen, alkyl or haloalkyl.

In yet another embodiment of structure (II), n is 1 or 2; X is —$(CH_2)$—; $R^3$ and $R^4$ are each hydrogen; $R^7$ is alkyl, halo, haloalkyl, or —$OR^9$; $R^8$ is optionally substituted thiophenyl; and $R^9$ is hydrogen, alkyl or haloalkyl.

In still another embodiment of structure (II), n is 1 or 2; X is —$(CH_2)$—; $R^3$ and $R^4$ are each hydrogen; $R^7$ is —$C(R^{10})(R^{11})$—$R^{12}$, —$OR^9$ or halo; $R^8$ is optionally substituted thiophenyl; $R^9$ is alkyl or haloalkyl; $R^{10}$ and $R^{11}$ are each halo or alkyl (i.e., $R^{10}$ and $R^{11}$ are each independently halo or alkyl); and $R^{12}$ is alkyl, halo or haloalkyl.

In more specific embodiments of the compounds of structure II, the compounds is any one of the following: {3-[4-(1,1-difluoro-ethyl)-benzenesulfonyl]-thieno[2,3-e][1,2,3]triazolo[1,5-a]pyrimidin-5-yl}-thiophen-2-ylmethyl-amine; [see Table 2, compound 3k];

thiophen-2-ylmethyl-[3-(4-trifluoromethyl-benzenesulfonyl)-thieno[2,3-e][1,2,3]triazolo[1,5-a]pyrimidin-5-yl]-amine; [see Table 2, compound 3c];

thiophen-2-ylmethyl-[3-(4-trifluoromethoxy-benzenesulfonyl)-thieno[2,3-e][1,2,3]triazolo[1,5-a]pyrimidin-5-yl]-amine; [see Table 2, compound 3d];

{3-[4-methoxy-benzenesulfonyl]-thieno[2,3-e][1,2,3]triazolo[1,5-a]pyrimidin-5-yl}-thiophen-2-ylmethyl-amine; [see Table 2, compound 3f];

{3-[4-fluoro-benzenesulfonyl]-thieno[2,3-e][1,2,3]triazolo[1,5-a]pyrimidin-5-yl}-thiophen-2-ylmethyl-amine; [see Table 2, compound 3h];

{3-[4-bromo-benzenesulfonyl]-thieno[2,3-e][1,2,3]triazolo[1,5-a]pyrimidin-5-yl}-thiophen-2-ylmethyl-amine; [see Table 2, compound 3i];

{3-[4-chloro-benzenesulfonyl]-thieno[2,3-e][1,2,3]triazolo[1,5-a]pyrimidin-5-yl}-thiophen-2-ylmethyl-amine; and [see Table 1, compound 2bi];

{3-[3-chloro-benzenesulfonyl]-thieno[2,3-e][1,2,3]triazolo[1,5-a]pyrimidin-5-yl}-thiophen-2-ylmethyl-amine; [see Table 1, compound 2cw].

In still other embodiments of structure (II), $R^7$ is alkyl. In specific embodiments, the compound is any one of the following compounds: {3-[4-ethyl-benzenesulfonyl]-thieno[2,3-e][1,2,3]triazolo[1,5-a]pyrimidin-5-yl}-thiophen-2-ylmethyl-amine; [see Table 2, compound 1];

{3-[4-isopropyl-benzenesulfonyl]-thieno[2,3-e][1,2,3]triazolo[1,5-a]pyrimidin-5-yl}-thiophen-2-ylmethyl-amine; or [see Table 2, compound 3a and Table 1, compound 2bn];

{3-[3,4-dimethyl-benzenesulfonyl]-thieno[2,3-e][1,2,3]triazolo[1,5-a]pyrimidin-5-yl}-thiophen-2-ylmethyl-amine, [see Table 1, compound 2bd].

In another embodiment of structure (II), n is 1 or 2; X is a $C_{1-3}$alkylene chain; $R^3$ and $R^4$ are each hydrogen; $R^7$ is alkyl, halo, haloalkyl, or —$OR^9$; $R^8$ is optionally substituted furanyl; and $R^9$ is hydrogen, alkyl or haloalkyl.

In still another embodiment of structure (II), n is 1 or 2; X is —$(CH_2)$—; $R^3$ and $R^4$ are each hydrogen; $R^7$ is alkyl, halo, haloalkyl, or —$OR^9$; $R^8$ is optionally substituted furanyl; and $R^9$ is hydrogen, alkyl or haloalkyl.

In more specific embodiments of structure (II), the compound is any one of the following: furan-2-ylmethyl-[3-(4-isopropyl-benzenesulfonyl)-thieno[2,3-e][1,2,3]triazolo[1,5-a]pyrimidin-5-yl]-amine; [see Table 2, compound 3b];

furan-2-ylmethyl-[3-(4-methyl-benzenesulfonyl)-thieno[2,3-e][1,2,3]triazolo[1,5-a]pyrimidin-5-yl]-amine; [see Table 1, compound 2ac];

furan-2-ylmethyl-[3-(3,4-dimethyl-benzenesulfonyl)-thieno[2,3-e][1,2,3]triazolo[1,5-a]pyrimidin-5-yl]-amine; [see Table 1, compound 2am];

furan-2-ylmethyl-[3-(4-chloro-benzenesulfonyl)-thieno[2,3-e][1,2,3]triazolo[1,5-a]pyrimidin-5-yl]-amine; [see Table 1, compound 2bf];

furan-2-ylmethyl-[3-(4-ethyl-benzenesulfonyl)-thieno[2,3-e][1,2,3]triazolo[1,5-a]pyrimidin-5-yl]-amine; and [see Table 1, compound 2 bp];

furan-2-ylmethyl-[3-(2,5-dimethyl-benzenesulfonyl)-thieno[2,3-e][1,2,3]triazolo[1,5-a]pyrimidin-5-yl]-amine. [see Table 1, compound 2cs].

In other embodiments of the compound of structure (II), n is 1 or 2; X is a $C_{1-3}$ alkylene chain; each $R^3$ and $R^4$ is independently hydrogen, alkyl, halo or haloalkyl; $R^7$ is alkyl, halo, haloalkyl, or —$OR^9$; $R^8$ is —$OR^9$; and $R^9$ is hydrogen, alkyl or haloalkyl.

In yet other embodiments of the compound of structure (II), the compound is any one of the following: {3-benzenesulfonyl-thieno[2,3-e][1,2,3]triazolo[1,5-a]pyrimidin-5-yl}-3-methoxypropyl-amine; [see Table 1, compound 2ab];

{3-[4-methyl-benzenesulfonyl]-thieno[2,3-e][1,2,3]triazolo[1,5-a]pyrimidin-5-yl}-3-(1-methylethoxyl)propyl-amine; [see Table 1, compound 2af];

{3-[4-methyl-benzenesulfonyl]-thieno[2,3-e][1,2,3]triazolo[1,5-a]pyrimidin-5-yl}-2-methoxyethyl-amine; [see Table 1, compound 2ai];

{3-[3,4-dimethyl-benzenesulfonyl]-thieno[2,3-e][1,2,3]triazolo[1,5-a]pyrimidin-5-yl}-3-ethoxylpropyl-amine; [see Table 1, compound 2aw];

{3-[3,4-dimethyl-benzenesulfonyl]-thieno[2,3-e][1,2,3]triazolo[1,5-a]pyrimidin-5-yl}-3-(1-methylethoxyl)propyl-amine; [see Table 1, compound 2ax];

{3-[3,4-dimethyl-benzenesulfonyl]-thieno[2,3-e][1,2,3]triazolo[1,5-a]pyrimidin-5-yl}-2-methoxyethyl-amine; [see Table 1, compound 2ba];

{3-[4-chloro-benzenesulfonyl]-thieno[2,3-e][1,2,3]triazolo[1,5-a]pyrimidin-5-yl}-2-methoxyethyl-amine; [see Table 1, compound 2bh];

{3-[4-chloro-benzenesulfonyl]-thieno[2,3-e][1,2,3]triazolo[1,5-a]pyrimidin-5-yl}-3-methoxypropyl-amine; [see Table 1, compound 2bj];

{3-[4-isopropyl-benzenesulfonyl]-thieno[2,3-e][1,2,3]triazolo[1,5-a]pyrimidin-5-yl}-3-ethoxylpropyl-amine; [see Table 1, compound 2bl];

{3-[4-isopropyl-benzenesulfonyl]-thieno[2,3-e][1,2,3]triazolo[1,5-a]pyrimidin-5-yl}-2-methoxyethyl-amine; [see Table 1, compound 2bo];

{3-[4-ethyl-benzenesulfonyl]-thieno[2,3-e][1,2,3]triazolo[1,5-a]pyrimidin-5-yl}-2-methoxyethyl-amine; [see Table 1, compound 2by];

{3-[4-ethyl-benzenesulfonyl]-thieno[2,3-e][1,2,3]triazolo[1,5-a]pyrimidin-5-yl}-3-methoxypropyl-amine; [see Table 1, compound 2cb];

{3-[4-ethyl-benzenesulfonyl]-thieno[2,3-e][1,2,3]triazolo[1,5-a]pyrimidin-5-yl}-3-(1-methylethoxyl)propyl-amine; [see Table 1, compound 2cf];

{3-[2,5-dimethyl-benzenesulfonyl]-thieno[2,3-e][1,2,3]triazolo[1,5-a]pyrimidin-5-yl}-3-ethoxypropyl-amine; [see Table 1, compound 2ck];

{3-[2,5-dimethyl-benzenesulfonyl]-thieno[2,3-e][1,2,3]triazolo[1,5-a]pyrimidin-5-yl}-3-(1-methylethoxyl)propyl-amine; [see Table 1, compound 2cl];

{3-[2,5-dimethyl-benzenesulfonyl]-thieno[2,3-e][1,2,3]triazolo[1,5-a]pyrimidin-5-yl}-2-methoxyethyl-amine; and [see Table 1, compound 2co];

{3-[2,5-dimethyl-benzenesulfonyl]-thieno[2,3-e][1,2,3]triazolo[1,5-a]pyrimidin-5-yl}-3-methoxypropyl-amine; [see Table 1, compound 2cr].

In other embodiments of the compound of structure (II), n is 1 or 2; X is a $C_{1-2}$ alkylene chain; each $R^3$ and $R^4$ are independently hydrogen, alkyl, halo or haloalkyl; $R^7$ is alkyl, halo, haloalkyl, or —$OR^9$; $R^8$ is optionally substituted aryl; and $R^9$ is hydrogen, alkyl or haloalkyl.

In more specific embodiments of structure (II), the compound is any one of the following: [3-(4-isopropyl-benzenesulfonyl)-thieno[2,3-e][1,2,3]triazolo[1,5-a]pyrimidin-5-yl]-(4-methoxy-benzyl)-amine; [see Table 2, compound 3e];

[3-(4-isopropyl-benzenesulfonyl)-thieno[2,3-e][1,2,3]triazolo[1,5-a]pyrimidin-5-yl]-naphthalen-1-ylmethyl-amine; [see Table 2, compound 3j];

[3-(4-methyl-benzenesulfonyl)-thieno[2,3-e][1,2,3]triazolo[1,5-a]pyrimidin-5-yl]-(4-methoxy-benzyl)-amine; [see Table 1, compound 2ad];

[3-(4-methyl-benzenesulfonyl)-thieno[2,3-e][1,2,3]triazolo[1,5-a]pyrimidin-5-yl]-(1-phenyl-1-methyl)methyl-amine; [see Table 1, compound 2ag];

[3-(4-methyl-benzenesulfonyl)-thieno[2,3-e][1,2,3]triazolo[1,5-a]pyrimidin-5-yl]-(3-methoxy-benzyl)-amine; [see Table 1, compound 2ah];

[3-(4-methyl-benzenesulfonyl)-thieno[2,3-e][1,2,3]triazolo[1,5-a]pyrimidin-5-yl]-(4-fluoro-benzyl)-amine; [see Table 1, compound 2aj];

[3-(3,4-dimethyl-benzenesulfonyl)-thieno[2,3-e][1,2,3]triazolo[1,5-a]pyrimidin-5-yl]-benzyl-amine; [see Table 1, compound 2ao];
[3-(3,4-dimethyl-benzenesulfonyl)-thieno[2,3-e][1,2,3]triazolo[1,5-a]pyrimidin-5-yl]-(2-chloro-benzyl)-amine; [see Table 1, compound 2ar];
[3-(3,4-dimethyl-benzenesulfonyl)-thieno[2,3-e][1,2,3]triazolo[1,5-a]pyrimidin-5-yl]-(2-methoxy-benzyl)-amine; [see Table 1, compound 2as];
[3-(3,4-dimethyl-benzenesulfonyl)-thieno[2,3-e][1,2,3]triazolo[1,5-a]pyrimidin-5-yl]-(4-methoxy-benzyl)-amine; see Table 1, compound [2at];
[3-(3,4-dimethyl-benzenesulfonyl)-thieno[2,3-e][1,2,3]triazolo[1,5-a]pyrimidin-5-yl]-(3-methoxy-benzyl)-amine; [see Table 1, compound 2ay];
[3-(3,4-dimethyl-benzenesulfonyl)-thieno[2,3-e][1,2,3]triazolo[1,5-a]pyrimidin-5-yl]-(4-chloro-benzyl)-amine; [see Table 1, compound 2bc];
[3-(3,4-dimethyl-benzenesulfonyl)-thieno[2,3-e][1,2,3]triazolo[1,5-a]pyrimidin-5-yl]-(4-fluoro-benzyl)-amine; [see Table 1, compound 2be];
[3-(4-ethyl-benzenesulfonyl)-thieno[2,3-e][1,2,3]triazolo[1,5-a]pyrimidin-5-yl]-benzyl-amine; [see Table 1, compound 2br];
[3-(4-ethyl-benzenesulfonyl)-thieno[2,3-e][1,2,3]triazolo[1,5-a]pyrimidin-5-yl]-(4-chloro-benzyl)-amine; [see Table 1, compound 2bt];
[3-(4-ethyl-benzenesulfonyl)-thieno[2,3-e][1,2,3]triazolo[1,5-a]pyrimidin-5-yl]-(1-phenyl-1-methyl)methyl-amine; [see Table 1, compound 2bw];
[3-(4-ethyl-benzenesulfonyl)-thieno[2,3-e][1,2,3]triazolo[1,5-a]pyrimidin-5-yl]-(3-methoxy-benzyl)-amine; [see Table 1, compound 2bx];
[3-(4-ethyl-benzenesulfonyl)-thieno[2,3-e][1,2,3]triazolo[1,5-a]pyrimidin-5-yl]-(4-fluoro-benzyl)-amine; [see Table 1, compound 2ca];
[3-(2,5-dimethyl-benzenesulfonyl)-thieno[2,3-e][1,2,3]triazolo[1,5-a]pyrimidin-5-yl]-(1-phenyl-1-methyl)methyl-amine; [see Table 1, compound 2 cm];
[3-(2,5-dimethyl-benzenesulfonyl)-thieno[2,3-e][1,2,3]triazolo[1,5-a]pyrimidin-5-yl]-(4-fluoro-benzyl)-amine; and [see Table 1, compound 2cp];
[3-(2,5-dimethyl-benzenesulfonyl)-thieno[2,3-e][1,2,3]triazolo[1,5-a]pyrimidin-5-yl]-benzyl-amine; [see Table 1, compound 2cq].

In another embodiment of a compound of structure (II), n is 1 or 2; X is a $C_{1-2}$ alkylene chain; each $R^3$ and $R^4$ is independently hydrogen, alkyl, halo or haloalkyl; $R^7$ is alkyl, halo, haloalkyl, or —$OR^9$; $R^8$ is optionally substituted heterocyclyl; and $R^9$ is hydrogen, alkyl or haloalkyl.

In certain embodiments, $R^8$ is tetrahydrofuranyl.

In still more specific embodiments, the compound of structure (II) is any one of the following compounds: tetrahydrofuran-2-ylmethyl-[3-(4-methyl-benzenesulfonyl)-thieno[2,3-e][1,2,3]triazolo[1,5-a]pyrimidin-5-yl]-amine; [see Table 1, compound 2ae];
tetrahydrofuran-2-ylmethyl-[3-(4-isopropyl-benzenesulfonyl)-thieno[2,3-e][1,2,3]triazolo[1,5-a]pyrimidin-5-yl]-amine; or [see Table 1, compound 2bk];
tetrahydrofuran-2-ylmethyl-[3-(4-ethyl-benzenesulfonyl)-thieno[2,3-e][1,2,3]triazolo[1,5-a]pyrimidin-5-yl]-amine; [see Table 1, compound 2bu].

In another embodiment of the compound of structure (I), $R^1$ is optionally substituted heteroaryl; $R^2$ is —$N(R^5)(R^6)$; each $R^3$ and $R^4$ is independently hydrogen, alkyl, halo or haloalkyl; $R^5$ is hydrogen or alkyl; and $R^6$ is optionally substituted alkyl, optionally substituted cycloalkyl, optionally substituted heterocyclylalkyl, optionally substituted aralkyl, or optionally substituted heteroarylalkyl.

In yet another embodiment of the compound of structure (I), $R^1$ is optionally substituted heteroaryl; $R^2$ is —$N(R^5)(R^6)$; each $R^3$ and $R^4$ is independently hydrogen, alkyl, halo or haloalkyl; $R^5$ is hydrogen or alkyl; and $R^6$ is optionally substituted heteroarylalkyl.

In still another embodiment of the compound of structure (I), $R^1$ is optionally substituted thiophenyl; $R^2$ is —$N(R^5)(R^6)$; each $R^3$ and $R^4$ are independently hydrogen, alkyl, halo or haloalkyl; $R^5$ is hydrogen or alkyl; and $R^6$ is optionally substituted thiophenyl.

In a specific embodiment, a compound of structure I is the following: [3-(thiophene-2-sulfonyl)-thieno[2,3-e][1,2,3]triazolo[1,5-a]pyrimidin-5-yl]-thiophen-2-ylmethyl-amine, [see Table 2, compound 3g].

In another embodiment, a compound of structure (III) is provided wherein structure (III) has the following formulae:

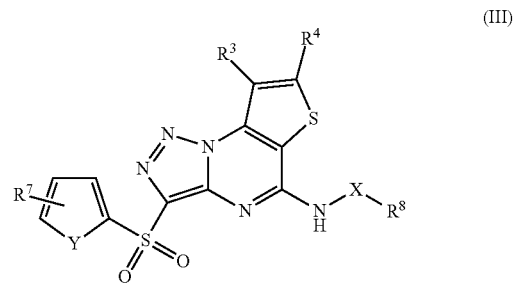

(III)

or a single stereoisomer, a mixture of stereoisomers, tautomer or pharmaceutically acceptable salt thereof, wherein,
X is an alkylene chain;
Y is —CH=$CH_2$—, —CH=N—, S, or O;
each $R^3$ and $R^4$ is independently hydrogen, alkyl, halo or haloalkyl;
$R^7$ is —$C(R^{10})(R^{11})$—$R^{12}$, —$OR^9$ or halo;
$R^8$ is optionally substituted aryl, optionally substituted heteroaryl or optionally substituted heterocyclyl, or —$OR^9$;
$R^9$ is alkyl or haloalkyl;
$R^{10}$ and $R^{11}$ are each halo or alkyl; and
$R^{12}$ is alkyl, halo or haloalkyl.

In certain embodiments, X is a $C_{1-5}$ alkylene chain or a $C_{1-3}$ alkylene chain. In a more particular embodiment, X is —$CH_2$—.

In certain embodiments, at least one of $R^3$ and $R^4$ is hydrogen (H). In particular embodiments, $R^3$ and $R^4$ are each hydrogen. In other particular embodiments, $R^3$ and $R^4$ are each independently hydrogen, $C_1$-$C_3$ alkyl, halo or $C_1$-$C_3$ halo alkyl.

In certain embodiments of a compound of structure (III), Y is —CH=$CH_2$— (to form a phenyl) and $R^7$ is —$C(R^{10})(R^{11})$—$R^{12}$, —$OR^9$ or halo. In certain particular embodiments, at least one of $R^{10}$ and $R^{11}$ and $R^{12}$ is alkyl (e.g., $C_1$-$C_3$ alkyl). In certain particular embodiments, each of $R^{10}$ and $R^{11}$ and $R^{12}$ is alkyl (e.g., $C_1$-$C_3$ alkyl). In other particular embodiments, each of $R^{10}$ and $R^{11}$ and $R^{12}$ is methyl. In certain particular embodiments, at least one of $R^{10}$ and $R^{11}$ and $R^{12}$ is methyl. In other particular embodiments, at least one of $R^{10}$ and $R^{11}$ and is $R^{12}$ is halo (i.e., F, Cl, Br, or I, for example, F). In other particular embodiments, at least two of $R^{10}$ and $R^{11}$ and $R^{12}$ are halo (e.g., F). In still other particular embodiments, each of $R^{10}$ and $R^{11}$ and $R^{12}$ is halo (e.g., F). In other particular embodiments, $R^7$ is halo. In certain particular embodiments, $R^7$ is F. In other certain embodiments, $R^7$ is —$OR^9$, and $R^9$ may be $C_1$-$C_3$ alkyl (e.g., —$CH_3$, —$CH_2CH_3$, —$CH_2(CH_3)_2$) or $C_1$-$C_3$ haloalkyl, which in certain particular embodiments, is a fluoroalkyl. In more particular embodiments, $R^9$ is —$CH_3$, or —$CF_3$. In other embodiments, Y is S.

In certain particular embodiments, when Y is —CH=$CH_2$— and $R^7$ is isopropyl at the position para to the linking carbon (i.e., the carbon linking to S), $R^8$ is not furanyl or thiophenyl. In another more specific embodiment, when Y is —CH=$CH_2$— and $R^7$ is Br at the position para to the linking carbon (i e, linking to S), $R^8$ is not thiophenyl.

In particular embodiments of a compound of structure (III), Y is —CH=$CH_2$—; and $R^8$ is optionally substituted heteroaryl. In particular embodiments, the heteroatom of the heteroaryl is S or O.

In a more particular embodiment, $R^8$ is optionally substituted thiophenyl.

In certain specific embodiments, $R^8$ is unsubstituted thiophenyl.

In a specific embodiment, a compound of structure (III) is any one of the following: 3-[4-(1,1-difluoro-ethyl)-benzenesulfonyl]-thieno[2,3-e][1,2,3]triazolo[1,5-a]pyrimidin-5-yl}-thiophen-2-ylmethyl-amine; [see Table 2, compound 3k];

thiophen-2-ylmethyl-[3-(4-trifluoromethyl-benzenesulfonyl)-thieno[2,3-e][1,2,3]triazolo[1,5-a]pyrimidin-5-yl]-amine; [see Table 2, compound 3c];

thiophen-2-ylmethyl-[3-(4-trifluoromethoxy-benzenesulfonyl)-thieno[2,3-e][1,2,3]triazolo[1,5-a]pyrimidin-5-yl]-amine; [see Table 2, compound 3d];

3-[4-methoxy-benzenesulfonyl]-thieno[2,3-e][1,2,3]triazolo[1,5-a]pyrimidin-5-yl}-thiophen-2-ylmethyl-amine; [see Table 2, compound 3f];

3-[4-fluoro-benzenesulfonyl]-thieno[2,3-e][1,2,3]triazolo[1,5-a]pyrimidin-5-yl}-thiophen-2-ylmethyl-amine; or [see Table 2, compound 3h];

3-[4-bromo-benzenesulfonyl]-thieno[2,3-e][1,2,3]triazolo[1,5-a]pyrimidin-5-yl}-thiophen-2-ylmethyl-amine; [see Table 2, compound 3i].

In another embodiment of the compound of structure (III), Y is S; and $R^8$ is optionally substituted heteroaryl.

In a more particular embodiment, $R^8$ is optionally substituted thiophenyl.

In a specific embodiment, a compound of structure (III) is [3-(thiophene-2-sulfonyl)-thieno[2,3-e][1,2,3]triazolo[1,5-a]pyrimidin-5-yl]-thiophen-2-ylmethyl-amine; [see Table 2, compound 3g].

In other embodiments, provided herein are pharmaceutical compositions comprising at least one of the compounds of structures (I), (II), and (III) described above and herein and a pharmaceutically acceptable (i.e., suitable) excipient.

In another embodiment, methods of using the compounds and pharmaceutical compositions comprising the compounds are provided herein. In one embodiment, a method is provided for treating a disease, disorder, or condition that is treatable by inhibiting transport of urea in a subject. This method comprises administering to the subject a pharmaceutical composition comprising a pharmaceutically acceptable excipient and at least one of the compounds of structure (I), (II), and (III) described above and herein. In one embodiment, the disease, disorder, or condition to be treated by inhibiting transport of urea is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis. In another specific embodiment, the disease, disorder, or condition to be treated is associated with a fluid retention imbalance; in another certain specific embodiment, the fluid retention imbalance comprises urea clearance insufficiency. In still another embodiment, treating the disease, disorder, or condition comprises inhibiting the capability of at least one urea transporter to transport urea. In certain specific embodiments, the at least one urea transporter is a UT-B transporter.

In other embodiments, methods are provided for inhibiting transport of urea across a cell membrane comprising contacting a cell with a composition that comprises at least one of the compounds of structure (I), (II), and (III) (including substructures and specific compounds) described herein, wherein the cell comprises at least one urea transporter. In one embodiment, at least one compound described herein inhibits the capability of a UT-B transporter to transport urea.

As described herein the aforementioned triazolothienopyrimidine compounds are capable of inhibiting the transport activity a urea transporter (e.g., UT-B) and are therefore useful for treating a disease, disorder, or condition treatable by inhibiting transport of urea. The compounds described herein are potent inhibitors that selectively and reversibly inhibit urea transport thereby reducing urinary concentration in a subject to whom the compound is administered. These compounds, particularly those referred to herein and in Table 2 (compounds 3a-3k), also have excellent metabolic stability in vivo.

DEFINITIONS

The terms below, as used herein, have the following meanings unless indicated otherwise.

Certain chemical groups named herein are preceded by a shorthand notation indicating the total number of carbon atoms that are to be found in the indicated chemical group. For example; $C_1$-$C_6$ alkyl describes an alkyl group, as defined below, having a total of 1 to 6 carbon atoms, and $C_3$-$C_{12}$ cycloalkyl describes a cycloalkyl group, as defined below, having a total of 3 to 12 carbon atoms. The total number of carbons in the shorthand notation does not include carbons that may exist in substituents of the group described. In addition to the foregoing, as used herein, unless specified to the contrary, the following terms have the meaning indicated.

"Alkyl" refers to a straight or branched hydrocarbon chain radical consisting solely of carbon and hydrogen atoms, which is saturated, having from one to six carbon atoms ($C_1$-$C_6$ alkyl), and which is attached to the rest of the molecule by a single bond. An alkyl radical may also be called herein a "lower alkyl," which refers to an alkyl radical, that has between, for example, 1 to 6 carbon atoms, 1 to 5 carbon atoms ($C_1$-$C_5$ alkyl) or 1 to 3 carbon atoms ($C_1$-$C_3$ alkyl). Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, isopentyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated and having from one to twelve carbon atoms, e.g., methylene, ethylene, propylene, n-butylene, ethenylene, propenylene, n-butenylene, propynylene, n-butynylene, and the like. The alkylene chain may be attached to the remainder of the molecule and to the radical group through one carbon or any two carbons, typically, the two terminal carbon atoms, within the chain. Unless stated otherwise specifically in the specification, an alkylene chain may be optionally substituted.

"Alkenylene" and "alkenylene chain" refer to a straight or branched divalent hydrocarbon chain consisting solely of carbon and hydrogen, containing at least one double bond and having up to 30 carbon atoms, preferably having from 2-12 carbons, e.g., ethenylene, propenylene, n-butenylene, and the like. The alkylene chain links two moieties, e.g., the remainder of the molecule and another radical. The alkenylene chain may be attached to the remainder of the molecule and to the radical group through any two carbons, typically, the two terminal carbon atoms, within the chain. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like.

"Alkoxy" refers to a radical of the formula —$OR_a$ where $R_a$ is an alkyl, or haloalkyl radical as defined above containing one to six carbon atoms. Representative alkoxy groups include methoxy and ethoxy. Unless stated otherwise specifically in the specification, an alkoxy group may be optionally substituted. An alkoxy that is substituted with halo may be called herein a haloalkoxy, which includes for example trifluoromethoxy, trichloromethoxy and the like.

Acyl refers to a radical —C(O)—R, wherein R is alkyl, aralkyl, carbocyclyl, aryl, heteroaryl or heterocyclyl, as defined herein. Where R is methyl, the acyl group is also referred to as acetyl.

Halo refers to fluoro, chloro, bromo or iodo radical.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 1,2-dibromoethyl, and the like. A "fluoroalkyl" is a haloalkyl, which comprises at least one fluorine substitution. Unless stated otherwise specifically in the specification, a haloalkyl group may be optionally substituted.

"Carbocyclyl" or "carbocycle" refers to a stable monocyclic or bicyclic hydrocarbon radical consisting solely of carbon and hydrogen atoms, having from three to fifteen ring carbon atoms, preferably having from three to ten ring carbon atoms, and which is saturated (no double bond) or unsaturated (having at least one double bond). Carbocyclyl may also be non-aromatic or aromatic. Non-aromatic carbocyclyl includes, e.g., cyclopropyl, cyclobutyl, cyclopentyl, cyclohexyl, decalinyl and the like. Aromatic carbocyclyl is also referred to as aryl, as further defined herein. In certain embodiments, the carbocycle may be a monovalent radical that is attached to the remainder of the molecule via a single or double bond at any one of the ring carbon atom. In other embodiments, the carbocycle may be a bivalent radical that is attached to two radicals (e.g., an alkylene chain and an alkyl) via single or double bonds at any two of the ring carbon atoms. Unless otherwise stated specifically in the specification, the term "carbocyclyl" is meant to include radicals which are optionally substituted by one or more substituents independently selected from the group consisting of alkyl (e.g., a lower alkyl, $C_{1-6}$, $C_{1-5}$, $C_{1-3}$), halo, hydroxy, —$NR_aR_b$, oxo, alkoxy, haloalkoxy, and wherein $R_a$ and $R_b$ are each independently hydrogen, acyl, or alkyl.

"Aryl" is a subset of carbocycle and refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl (e.g., $C_{1-6}$, $C_{1-5}$, or $C_{1-3}$ lower alkyl), halo, hydroxy, —$NR_aR_b$, oxo, alkoxy, haloalkoxy, and wherein $R_a$ and $R_b$ are each independently hydrogen, acyl, or alkyl.

"Aralkyl" refers to a radical of the formula —$R_xR_y$ where $R_x$ is an alkylene radical as defined above and $R_y$ is one or more aryl radicals as defined above. Examples of aralkyl include benzyl, diphenylmethyl and the like. The aryl radical(s) may be optionally substituted as described above.

"Heterocyclyl" refers to a stable 3- to 18-membered non-aromatic ring radical which consists of carbon atoms and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Aromatic heterocycles are also referred to as heteroaryls, as further defined herein. Examples of such heterocyclyl radicals include, but are not limited to, furanyl, thienyl (i.e., thiophenyl), pyrrolyl, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In certain embodiments, the heterocycle may be a monovalent radical that is attached to the remainder of the molecule via a single or double bond at any one of the ring atom (e.g., carbon or nitrogen). In other embodiments, the heterocycle may be a bivalent radical that is attached to two radicals (e.g., an alkylene chain and an alkyl) via single or double bonds at any two of the ring atoms (e.g., carbon or nitrogen). Unless stated otherwise specifically in the specification, the term "heterocyclyl" is meant to include heterocyclyl radicals as defined above which are optionally substituted by one or more substituents independently selected from the group consisting of alkyl (e.g., $C_{1-6}$, $C_{1-5}$, or $C_{1-3}$ lower alkyl), halo, hydroxy, —$NR_aR_b$, oxo, alkoxy, haloalkoxy, and wherein $R_a$ and $R_b$ are each independently hydrogen, acyl, or alkyl. "N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heteroaryl" is a subset of heterocycle and refers to a 3- to 18-membered aromatic ring radical which consists of carbon atoms and from one to five heteroatoms selected from the group consisting of nitrogen, oxygen and sulfur. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl (e.g., $C_{1-6}$, $C_{1-5}$, or $C_{1-3}$ lower alkyl), halo, hydroxy, —$NR_aR_b$, oxo, and $C_{1-6}$, $C_{1-5}$, or $C_{1-3}$ lower alkyl, and wherein $R_a$ and $R_b$ are each independently hydrogen, acyl, or alkyl. "N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

Oxo refers to the =O radical.

"Optional" or "optionally" means that the subsequently described event or circumstance may or may not occur, and that the description includes instances where the event or circumstance occurs and instances in which it does not. For example, "optionally substituted aryl," (or optionally substituted heteroaryl, alkyl, cycloalkyl, heterocyclyalkyl, aralkyl, heteroarylalkyl, N-heterocycle, or N-heteraryl, thienyl, furanyl, phenyl, and the like) means that the aryl radical (or heteroaryl, alkyl, cycloalkyl, heterocyclyalkyl, aralkyl, heteroarylalkyl, N-heterocycle, or N-heteraryl, thienyl, furanyl, phenyl, and the like) may or may not be substituted and that the description includes both substituted radicals and radicals having no substitution (i.e., unsubstituted).

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of structures (I), (II), (III), and substructures thereof, as well as any and all substructures and specific compounds described herein is intended to encompass any and all pharmaceutically suitable salt forms.

Compounds of structures (I), (II), (III), and substructures thereof may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

Furthermore, some of the crystalline forms of any compound described herein may exist as polymorphs, which are also included and contemplated by the present disclosure. In addition, some of the compounds may form solvates with water or other organic solvents. Often crystallizations produce a solvate of the disclosed compounds. As used herein, the term "solvate" refers to an aggregate that comprises one or more molecules of any of the disclosed compounds with one or more molecules of solvent. The solvent may be water, in which case the solvate may be a hydrate. Alternatively, the solvent may be an organic solvent. Thus, the presently disclosed compounds may exist as a hydrate, including a monohydrate, dihydrate, hemihydrate, sesquihydrate, trihydrate, tetrahydrate and the like, as well as the corresponding solvated forms. Certain embodiments of the compounds may be true solvates, while in other cases, some embodiments of the compounds may merely retain adventitious water or be a mixture of water plus some adventitious solvent.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

With regard to stereoisomers, the compounds of structure (I), (II) and (III), as well as any substructure herein, may have one or more chiral (or asymmetric) centers, and may thus give rise to enantiomers, diastereomers, and other stereoisomeric forms that may be defined, in terms of absolute stereochemistry, as (R)— or (S)—. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are non-superimposeable mirror images of one another. Thus, the compounds may occur in any isomeric form, including racemates, racemic mixtures, and as individual enantiomers or diastereomers. A "tautomer" refers to a proton shift from one atom of a molecule to another atom of the same molecule. Some embodiments of the disclosed compounds include tautomers of any said compounds.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Compound Synthesis

An exemplary triazolothienopyrimidine compound, $UTB_{inh}$-14, discussed herein has drug-like properties, including the presence of multiple hydrogen bond acceptors, a molecular weight of 455, and computed cLogP of 4.55 and polar surface area of 87 square A (see, e.g., Ghose et al., *J. Comb. Chem.* 1:55-68 (1999)). Other compounds having a triazolothienopyrimidine scaffold were described by Westerlund (*J. Heterocyclic Chem.* 17: 1765-69 (1980)), the synthesis of which involved cycloaddition chemistry to generate the core heterocycle. Generation of lactam 5 (see FIG. 1C) was based on this cycloaddition methodology. Recently, this general scaffold has been reported to show antagonist activity against 5-$HT_6$ receptors in vitro (see, e.g., Ivachtchenko et al., *Bioorg. Med. Chem.* 18:5282-90 (2010)), though no pharmacology or in vivo data were reported. The synthesis of triazolothienopyrimidine $UTB_{inh}$-14 can be accomplished in five steps with an overall yield of approximately 16%. The synthesis is designed to be modular, allowing diversification of the scaffold to improve physico-chemical properties. Notably, the phosphonium-mediated amidine forming conditions previously reported (see, e.g., Wan et al., *Org. Lett.* 8:2425-28 (2006)) was unsuccessful. The conditions described herein are adapted to employ microwave irradiation to effect conversion, and a workup that gave highly pure UTB$_{inh}$-14 by NMR and HPLC criteria.

Synthesis of other triazolothieneopyrimidine compounds described herein may be performed according to the following synthesis procedures and methods.

As shown in General Scheme 1, aryl or heteroaryl sulfonyl acetonitriles (6) may be prepared by reacting a thiol starting material (4), e.g., an appropriately substituted arylthiol or heteroarylthiol, with bromoacetonitrile (a) to provide an intermediate sulfide acetonitrile (5). The sulfide acetonitrile (5) may thereafter be treated with an oxidizing agent (b), e.g., mCPBA, to provide the sulfonyl acetonitrile compound (6).

General Scheme 1.

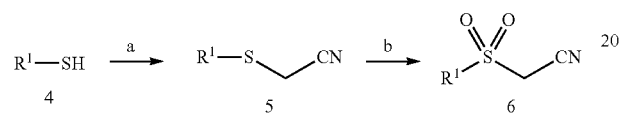

Scheme 1a shows certain exemplary thiol starting materials (4a-4g) and more specific, exemplary reaction conditions. See also Example 7.

Scheme 1a.

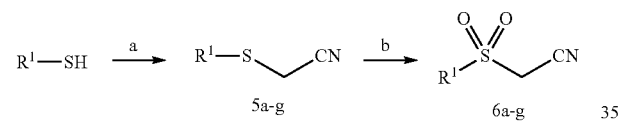

4a R$^1$ = 4-isopropylphenyl
4b R$^1$ = 4-trifluoromethylphenyl
4c R$^1$ = 4-trifluoromethoxyphenyl
4d R$^1$ = 4-methoxyphenyl
4e R$^1$ = thiophene-2-yl
4f R$^1$ = 4-fluorophenyl
4g R$^1$ = 4-bromophenyl Reagents and conditions are as follows: (a) bromoacetonitrile, K$_2$CO$_3$, DMF, 2 h, RT; (b) mCPBA, CH$_2$Cl$_2$, 0° C., 2 h.

As an alternative to the thiol starting material (4) of General Scheme 1, a brominated starting material (7) may be used. As shown in Scheme 2, a brominated aryl or heteroaryl (7) may be reacted with methyl thioacetate (a) to provide a sulfide acetate intermediate (8). Thereafter, the sulfide acetate intermediate (8) may be oxidized (b) to provide a sulfonyl acetate intermediate (9), which may be converted (c) to a sulfonyl amide (10). The sulfonyl amide (10) may undergo dehydration (d) to provide the sulfonyl acetonitrile compound (6).

General Scheme 2.

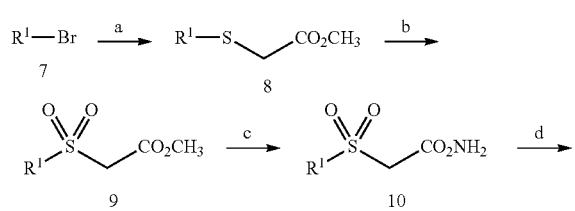

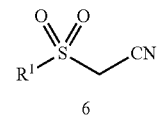

In a more specific reaction scheme, difluoroethyl aryl sulfonyl acetonitrile building block (6h) may be synthesized as illustrated in Scheme 2a. See also Example 7.

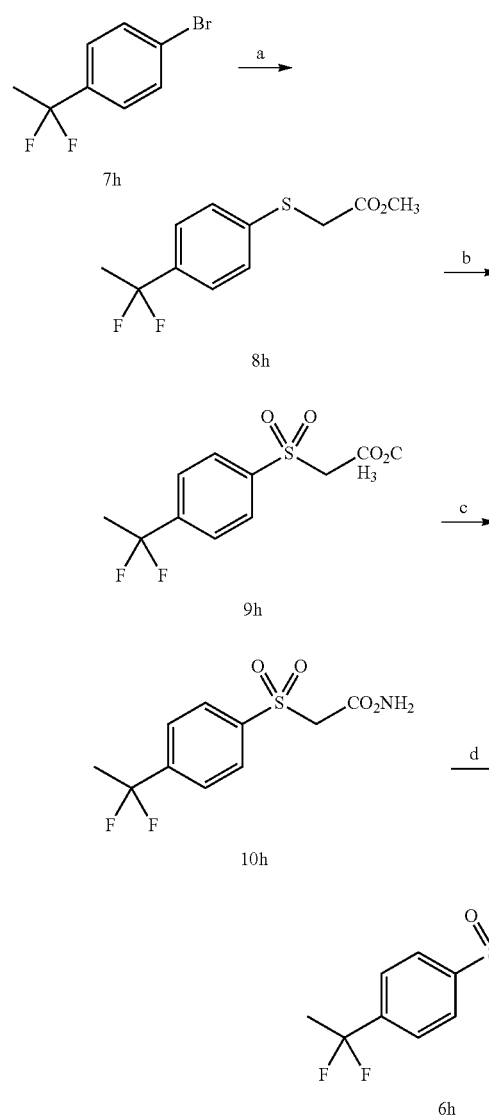

Reagents and conditions are as follows: (a) methyl thioacetate, Pd[PPh$_3$]$_4$, Xanthphos ligand, DIPEA, 1,4-dioxane, 135° C., 16 h; (b) mCPBA, CH$_2$Cl$_2$, 0° C., 2 h; (c) NH$_3$ in MeOH, 50° C. 16 h; (d) phosphorous pentoxide, toluene, 75° C., 1 h.

General Scheme 3 shows a general approach to preparing azidothiophenyl ester building block (14). An appropriately substituted 3-Bromothiophene-2-carboxaldehyde (11) is first azidated by nucleophilic aromatic substitution (a) to generate 3-azidothiophene aldehyde (12). This aldehyde (12) may be oxidized (b) to provide a carboxylic acid (13), which may be further alkylated (d) to provide 2-azidothiophene-1-alkyl ester (14).

General Scheme 3.

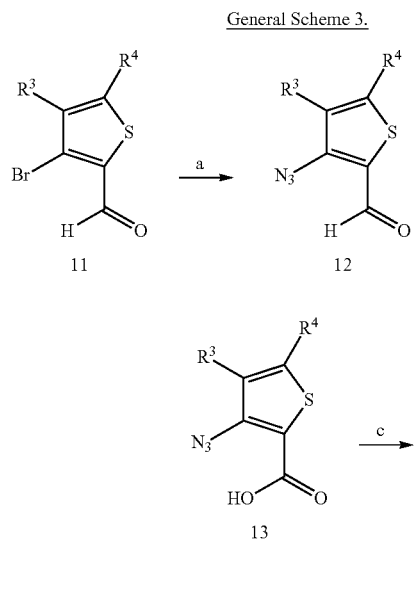

Scheme 3a illustrates an exemplary synthesis process of an azidothiophenyl isobutyl ester building block.

Scheme 3a.

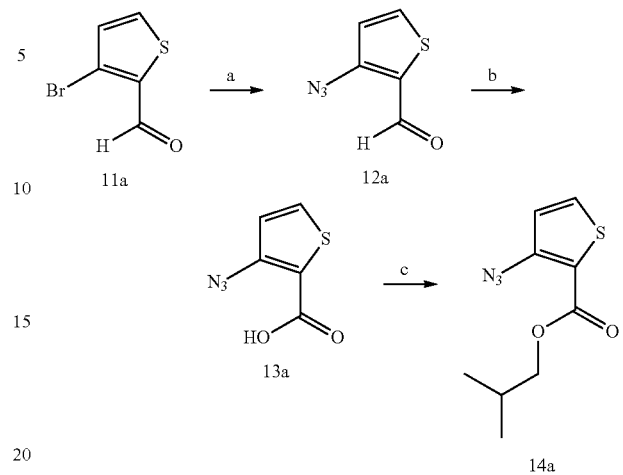

Reagents and conditions: (a) NaN$_3$, DMSO, 65° C., 48 h; (b) sodium chlorite, sulfamic acid, H$_2$O:acetone (1:1), 0° C., 30 min; (c) isobutyl bromide, Cs$_2$CO$_3$, DMF, 80° C., 6 h.

Triazolothienopyrimidine UTB inhibitors may then be synthesized according to the following General Scheme 4. An aryl sulfonyl acetonitrile building block (4) and an azidothiophenyl ester building block (14) may first undergo a [2+3] cycloaddition (a) to provide a lactam intermediate (15), which may further undergo a dehydrative amidine coupling with an amine (R$^2$—NH$_2$) (b) to provide the triazolothienopyrimidine UTB inhibitors (3).

General Scheme 4.

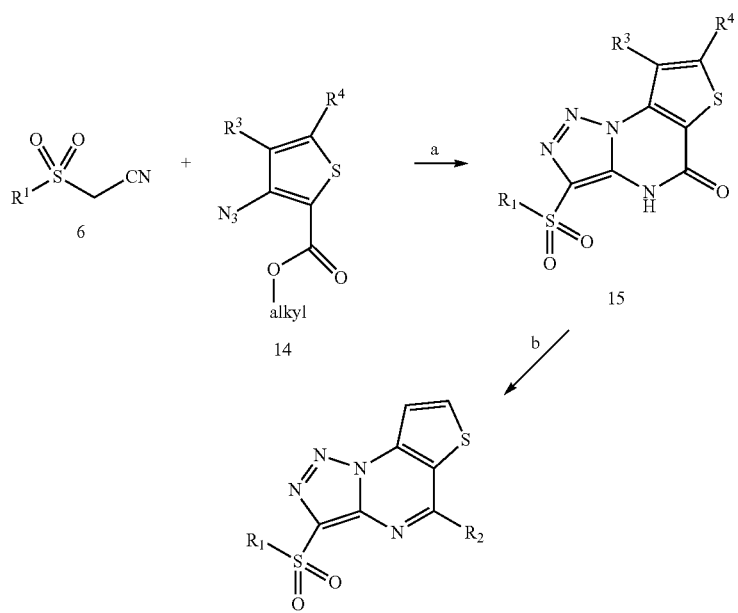

Scheme 4a. shows exemplary synthetic processes for preparing a number of UTB inhibitors via [2+3] cycloaddition and microwave-assisted dehydrative amidine coupling (see also Example 9):

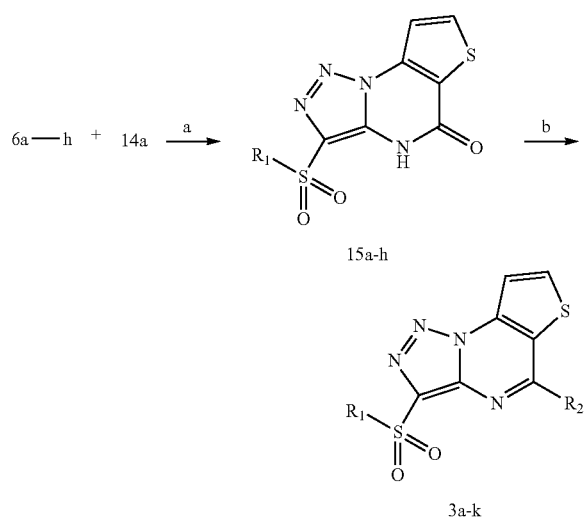

Reagents and conditions: (a) NaOEt, EtOH, 30 min, RT; (b) amines, PyBOP, CH$_3$CN, microwave, 100° C., 30 min.

Inhibition of Urea Transport

Provided herein are methods for using the triazolothienopyrimidine compounds of structure (I), (II), (III), and substructures and specific compounds described herein. As described in detail herein, methods are provided for treating a disease, disorder, or condition treatable by inhibiting transport of a neutrally charged solute (e.g., urea) in a subject by administering to the subject in need thereof a pharmaceutical composition comprising at least one of the compounds of structure (I), (II), (III), and substructures and specific compounds described above. In a particular embodiment, the compounds and compositions described herein may treat a disease, disorder, or condition by inhibiting transport of urea by a urea transporter. The compound may specifically inhibit all urea transporters or may interact with and inhibit only one subfamily of urea transporter (i.e., either UT-A transporters or UT-B transporters). In particular embodiments, the triazolothienopyrimidine compounds described herein may inhibit at least UT-B.

The compounds of the structure (I), (II), (III), and substructures and compounds described herein may be used to alter (i.e., increase or decrease in a statistically significant or biologically significant manner) transport of urea across a cell membrane by at least one urea transporter. In particular embodiments, transport activity of at least one urea transporter is inhibited by a compound of structure (I), (II), (III), and substructures and compounds, thus the compounds are capable of preventing, blocking, or decreasing transport of urea across a cell membrane. Methods are provided for an in vitro assay in which a cell comprising at least one urea transporter is contacted (combined, mixed, or in some manner permitted to interact) with a composition comprising at least one triazolothienopyrimidine compound described herein. In one embodiment, at least one compound described herein inhibits transport of urea by a UT-B transporter. In certain embodiments, the cell is a renal cell, a brain cell, a red blood cell, or a testis cell. In a particular embodiment, the cell is a renal cell. In another particular embodiment, the cell is a red blood cell, which comprises at least a UT-B transporter.

Urea transporters (UTs) are transmembrane proteins that transport urea across cellular membranes. UTs may be expressed in such tissues as the outer and inner medulla of the kidney, erythropoietic tissue, testis and hepatocytes. One function of UTs is production of concentrated urea, which is critical for retention of water.

The Slc14A1 gene encodes a single UT-B isoform (see, e.g., Sands, Curr. Opin. Nephroi. Hypertens. 13:525-32 (2004); Lucien et al., J. Biol. Chem. 273:12973-80 (1998); Bagnasco, Am. J. Physiol. Renal Physiol. 284:F3-F10 (2003); Sidoux et al., J. Biol. Chem. 274:30228-35 (1999); see also e.g., Tsukaguchi et al., J Clin Invest. 99:1506-15 (1997)). Five UT-A urea transporter isoforms (UT-A1, UT-A2, UT-A3, UT-A4, and UT-A5) are encoded by alternatively splicing of the Slc14A2 gene (see, e.g., Bagnasco et al., Am. J. Physiol. Renal Physiol. 281:F400-F406 (2001); Shayakul et al., Pflugers Arch. 447:603-609 (2004); Bagnasco, Pflugers Arch. 450:217-26 (2005); Sands, Curr. Opin. Nephrol. Hypertens. 13:525-32 (2004); Bagnasco, Am. J. Physiol. Renal Physiol. 284:F3-F10 (2003); Sands et al. Am. J. Physiol. 273:F321-39 (1997); Sands, Annu. Rev. Physiol. 65:543-66 (2003)).

In one embodiment, methods are provided for altering (i.e., increasing or decreasing in a statistically significant or biologically significant manner) transport of urea across a cell membrane by a urea transporter in a cell. Such methods comprise contacting (i.e., combining, mixing or in some manner permitting interaction with) the cell and any one or more (i.e., at least one) of the triazolothienopyrimidine compounds of structure (I), (II), (III), and substructures described herein or a composition comprising at least one or more of such compounds. The compounds described herein are capable of inhibiting transport of urea by at least one urea transporter (e.g., a UT-B) in a cell in vivo (i.e., in an animal, including a human) or in vitro in an assay method, for example.

In a specific embodiment, a method is provided for inhibiting transport of urea across a cell membrane, which method comprises contacting (i.e., combining, mixing or in some manner permitting interaction with) a cell with at least one compounds of the structure (I), (II), (III), and substructures or composition comprising such a compound as described herein, wherein the cell comprises at least one urea transporter, particularly the UT-B transporter. The compounds described herein inhibit (i.e., reduce, abrogate, prevent, or decrease in a statistically significant or biologically significant manner) the capability of at least one urea transporter to transport urea across a cell membrane. In a particular embodiment, the compounds interact with and inhibit a UT-B transporter.

Compounds of the structure (I), (II), (III), and substructures inhibit the capability of at least one urea transporter to transport urea across a cell membrane. In a particular embodiment, the transporter is located in the outer cell membrane and is capable of transporting a solute into the cell from the extracellular environment or space (influx) and out of the cell into the extracellular environment or space (efflux).

In a particular embodiment, the triazolothienopyrimidine compound inhibits (i.e., blocks, prevents, reduces, or decreases in a statistically or biologically significant manner) the capability of at least one urea transporter (e.g., UT-B) to transport urea across a cell membrane and thus inhibits urea influx and/or efflux. The compound may inhibit the transport activity of the transporter by binding to the transporter such that the compound inhibits transport of urea into the cell from the extracellular space, and/or the compound may bind to the transporter such that transport of urea out of the cell into the extracellular space is inhibited.

The transporter may be endogenously expressed by the cell (i.e., the genome of the cell comprises a nucleotide sequence that encodes the transporter, which is transcribed into mRNA that is translated). Alternative, for example, with respect to in vitro assay methods, the transporter may be recombinantly expressed in the cell (i.e., the cell comprises an exogenous polynucleotide that directs the expression of the transporter polypeptide).

With respect to assay methods described herein for characterizing a triazolothienopyrimidine compound, cells may be obtained or derived from a biological sample. A biological sample as used herein refers in certain embodiments to a sample containing at least one cell or a plurality of cells that endogenously or exogenously expresses at least one urea transporter. A biological sample may be a blood sample, such as whole blood or a cellular fraction of whole blood, biopsy specimen, body fluids that contain cells that express at least one transporter (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state of the tissue has been disrupted, for example, by dissection, dissociation, solubilization, fractionation, homogenization, biochemical or chemical extraction. The subject or biological source may be a human or non-human animal, a primary cell culture (e.g., kidney cells or other cells that endogenously express a transporter), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

The cells comprising a urea transporter that is inhibited by the compounds and compositions described herein include cells that endogenously express a urea transporter polypeptide. Exemplary cells that endogenously express a urea transporter include but are not limited to a renal cell, a brain cell, a red blood cell, a liver cell, or a testis cell. Transport of urea by urea transporters and transport of water by aquaporins are opposing processes in such cells. An exemplary cell that may be used in the methods described herein and that expresses a urea transporter is a red blood cell (i.e., erythrocyte), which endogenously expresses the urea transporter UT-B (also referred to as the Kidd blood group antigen).

Alternatively, the cells (which may be any one of a renal cell, a brain cell, a red blood cell, a liver cell, or a testis cell or other cell) may comprise an exogenous polynucleotide that encodes a urea transporter polypeptide. The cell may be transfected, transformed, or transduced with a recombinant expression vector, which comprises a polynucleotide that is capable of directing expression of at least one urea transporter. To direct expression of at least one transporter, the polynucleotide comprises a nucleotide sequence that encodes at least one urea transporter, which nucleotide sequence is operatively linked to at least one expression control sequence (e.g., a promoter, enhancer, transcriptional control element, and the like). Recombinant expression vectors may be prepared according to methods and techniques with which a person skilled in the molecular biology art is familiar. An exemplary cell line that may be transfected with a recombinant expression vector comprising a polynucleotide that directs expression of a urea transporter or other transport includes Madin-Darby canine kidney cells (MDCK).

Cells may be obtained or derived from any one of a number of animals, including mammals. Mammalian cells may be obtained or may have originated from humans; non-human primates; rodents such as mice, rats, or rabbits; cats (feline); dogs (canine); cattle (bovine); sheep (ovine); pigs (porcine); llamas; and camels, for example.

Methods that may be used to identify and to characterize urea transporter inhibitors, such as the compounds described herein, include red blood cell lysis methods and a stopped flow light scattering methods (see also, e.g., U.S. Patent Application Publication Nos. 2010/0305105 and 2010/0190796; Levin et al., supra). Such assays may be used to determine the effective concentrations of a particular compound and thus are useful for predicting the capability of the compound to effectively treat a disease, disorder, or condition treatable by inhibiting urea transporter activity in a subject.

Other methods for characterizing compounds include stopped-flow light scattering to measure solute and water permeabilities of a cell (see, e.g., Yang et al., *J Biol Chem.* 277:36782-86 (2002; *Epub* 2002 Jul. 19); Macey et al., *J. Membr. Biol.* 134(3):241-50 (1993)). For example, to determine the urea permeability of a cell, dilutions of indicator cells, such as red blood cells, may be incubated with an agent and then subjected to an inwardly directed gradient of urea. After the cells osmotically shrink (i.e., the cell volume decreases), the kinetics of increasing cell volume caused by urea influx can be measured over a time course during which the cells are exposed to 90° scattered light intensity at 530 nm. As the volume of the cell increases, scattered light intensity is reduced. Stopped flow light scattering may also be used to determine values for inhibition by a urea transporter and may also be used to determine the sideness of the inhibitor action (i.e., whether the inhibitor alters a solute transporter activity by preventing or inhibiting entry of a solute into the cell or whether the inhibitor alters a solute transport activity by preventing or inhibiting efflux of the inhibitor from the cell).

A person skilled in the art will appreciate that the methods and techniques described herein may include appropriate control samples to evaluate and ensure the robustness, accuracy, and precision of the method. Statistical methods may be applied to the determinations of the particular assay in the absence and presence of a candidate agent to evaluate and compare the different candidate agents tested.

Treatment of Urea Clearance Disorders

A composition comprising at least one of the triazolothienopyrimidine compounds described herein may be used for treating a disease, disorder, or condition in a subject. In one embodiment, methods are provided for treating a disease, disorder, or condition that is treatable by inhibiting transport of urea wherein the method comprises administering a composition comprising at least one compound as described herein.

UT inhibitors have a fundamentally different mechanism-of-action from conventional diuretics, which target kidney tubule salt transporters, and so may act in synergy. Diuretics are used widely to increase renal salt and water excretion in fluid overload conditions such as congestive heart failure, cirrhosis and nephrotic syndrome, and when vasopressin levels are inappropriately high such as in syndrome of inappropriate secretion of antidiuretic hormone (SIADH). By disrupting countercurrent mechanisms, UT inhibitors alone or in combination with loop diuretics, may induce a diuresis in states of refractory edema where conventional diuretics are not effective (see, e.g., Zhang *Am J Physiol Renal Physiol* 285: F731-F747 (2003); Fenton et al., *Pflugers Arch* 458:169-177, (2009); Smith, *Exp Physiol* 94:180-185 (2009)).

A disease, condition, or disorder treatable by inhibiting transport of urea includes a fluid retention imbalance, for example, urea clearance insufficiency. In certain instances, the urea clearance insufficiency is a renal urea clearance insufficiency. Triazolothienopyrimidines may be useful for therapy of diuretic-refractory edema in heart and liver failure. The compounds of structures (I), (II), (III), and substructures described herein may be used to treat a refractory edema associated with or caused by a cardiovascular, renal, or metabolic disease, disorder, or condition, such as cirrhosis, nephritic syndrome, acute renal failure, chronic renal insufficiency, hypertension, and congestive heart failure. In certain other embodiments, the disease, disorder, or condition to be treated is syndrome of inappropriate antidiuretic hormone secretion (SIADH), azotemia, fluid retention, and abnormal uresis. In other certain embodiments, at least one of the triazolothienopyrimidines compounds described herein may also be used in combination with a loop diuretic.

In a particular embodiment, methods are provided for treating such a disease, disorder, or condition by inhibiting the capability of at least one urea transporter to transport urea. In one embodiment, at least one of the compounds described herein inhibits the capability of a UT-B transporter to transport urea. A triazolothienopyrimidine compound described herein may be used as a type of diuretic, an "urearetic," that affects renal urea clearance mechanisms.

Methods are also provided for using the compounds described herein for treating a disease, disorder, or condition treatable by inhibiting transport of urea in a subject by administering to the subject in need thereof a pharmaceutical composition comprising at least one of the compounds having the structure and substructures described above. The disease, disorder, or condition that may be treated using the compounds and compositions described herein may be associated with a fluid retention imbalance such as urea clearance insufficiency. Urea is a by-product of protein metabolism that is formed in the liver. Because urea contains ammonia, which is toxic to an animal body, urea must be quickly filtered from the blood by the kidneys and excreted in the urine. Also as described herein, conservation of water in mammals depends significantly on the transport of urea, particularly in the kidney. Urea is generated as the major end product of hepatic nitrogen metabolism and is excreted primarily by the kidney. In a particular embodiment the disease, disorder, or condition to be treated is renal urea clearance insufficiency.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide at least one compound of structures (I), (II), (III), and substructures described herein in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, dogs (canine); cats (feline), cattle (bovine); sheep (ovine); pigs (porcine); llamas; and camels; and other domestic, farm, and zoo animals.

In one embodiment, treating any one of the aforementioned diseases or conditions comprises inhibiting (i.e., preventing, decreasing, reducing, abrogating, or inhibiting in a statistically significant or biologically significant manner) the capability of at least one urea transporter (e.g., UT-B) to transport urea by administering a composition comprising any one or more of the compounds of the structure (I), (II), (III), and substructures. The subject, and thus the source of the urea transporter, may be a human or non-human mammal.

To evaluate and to monitor the effectiveness of any one of the compounds described herein to treat a disease, disorder, or condition, one or more of several clinical assay methods may be performed that are familiar to a person skilled in the clinical art. For example, a clinical method called a urea clearance test may be performed. By way of example, a blood sample is obtained from a subject to whom the compound is being administered so that the amount of urea in the bloodstream can be determined. In addition, a first urine sample may be collected from the subject and additional samples may be collected over time (for example, at least one hour later). The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

Pharmaceutical Compositions

Also provided herein are pharmaceutical compositions that comprise any one or more of the triazolothienopyrimidine compounds of structures I, II, and III (and substructures and specific structures thereof). The compounds described herein may be formulated in a pharmaceutical composition for use in treatment or preventive (or prophylactic) treatment (e.g., reducing the likelihood of occurrence or exacerbation of disease or of one or more symptoms of the disease).

As used herein, a subject may be any mammal, including a human, that may have or be afflicted with a disease, condition, or disorder described herein. A pharmaceutical composition may be a sterile aqueous or non-aqueous solution, suspension or emulsion, which additionally comprises at least one physiologically acceptable excipient (i.e., a physiologically and pharmaceutically suitable non-toxic and inactive material or ingredient that does not interfere with the activity of the active ingredient; an excipient also may be called a carrier). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

In pharmaceutical dosage forms, any one or more of the compounds of structure (I), (II), (III), and substructures, and specific structures described herein may be administered in the form of a pharmaceutically acceptable derivative, such as a salt, or they may also be used alone or in appropriate association, as well as in combination, with other pharmaceutically active compounds. The methods and excipients described herein are exemplary and are in no way limiting. An effective amount or therapeutically effective amount refers to an amount of a compound or a composition comprising one or more compounds that when administered to a subject, either as a single dose or as part of a series of doses, is effective to produce a desired therapeutic effect.

Optimal doses may generally be determined using experimental models and/or clinical trials. The optimal dose may depend upon the body mass, weight, or blood volume of the subject. In general, the amount of a compound described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising at least one of the compounds described herein for treating a disease or condition may depend upon the subject's condition, that is, stage of the disease, severity of symptoms caused by the disease, general health status, as well as age, gender, and weight, and other factors apparent to a person skilled in the medical art. Similarly, the dose of the compound for treating a disease or disorder treatable by inhibiting urea transporters as described herein may be determined according to parameters understood by a person skilled in the medical art.

Pharmaceutical compositions comprising at least one triazolothienopyrimidine compound may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least one compound as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein that comprise at least one of the triazolothienopyrimidine compounds described herein may be administered to a subject in need by any one of several routes that effectively deliver an effective amount of the compound. Such administrative routes include, for example, oral, parenteral, enteral, rectal, intranasal, buccal, sublingual, intramuscular, and transdermal. Compositions administered by these routes of administration and others are described in greater detail herein.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, at least one of the compounds described herein can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

A composition comprising any one of the triazolothienopyrimidine compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The triazolothienopyrimidine compounds described herein can be formulated in pharmaceutical compositions as suppositories by mixing with a variety of bases such as emulsifying bases or water-soluble bases. These compounds may be administered rectally via a suppository. The suppository can include vehicles such as cocoa butter, carbowaxes and polyethylene glycols, which melt at body temperature, yet are solidified at room temperature.

The triazolothienopyrimidine compounds described herein may be used in aerosol formulation to be administered via inhalation. The compounds may be formulated into pressurized acceptable propellants such as dichlorodifluoromethane, propane, nitrogen and the like.

Any one or more of the triazolothienopyrimidine compounds described herein may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a triazolothienopyrimidine compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5):655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., *Urology* 2001;

57(2):301-5; Kiijavainen et al., *Eur. J. Pharm. Sci.* 2000; 10(2):97-102; and Tenjarla et al., *Int. J. Pharm.* 1999; 192(2): 147-58.

When a triazolothienopyrimidine compound is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. A triazolothienopyrimidine compound may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Also provided herein are methods of manufacturing the pharmaceutical compositions described herein that comprise at least one of the triazolothienopyrimidine compounds, as described herein. In one embodiment, the method of manufacture comprises synthesis of the compound. Synthesis of one of more of the compounds described herein may be performed according to methods described herein and practiced in the art. In another method of manufacture, the method comprises comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound, formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Other embodiments and uses will be apparent to one skilled in the art in light of the present disclosures. The following examples are provided merely as illustrative of various embodiments and shall not be construed to limit the claims in any way.

EXAMPLES

Materials and Methods

In addition to materials and methods described in specific examples, the following materials and methods were used in the examples described herein. Materials and methods are also described in Example 13, which provide certain experimental details for methods and techniques described in Examples 14 and 15.

Collection of Mouse and Human Blood

Whole blood was collected from 8-12 week-old (25-35 g) wild-type or UT-B-null mice (see, e.g., Yang et al., *J. Biol. Chem.*, supra (2002)) or AQP1-null mice (see, e.g., Ma et al., *J. Biol. Chem.* 273:4296-99 (1998)) in a CD1 genetic background by orbital puncture following subcutaneous injection of sodium heparin. Procedures were approved by the UCSF Committee on Animal Research. Human venous blood was collected into heparinized tubes, stored at 4° C., and used within 48 h.

Stopped-Flow Measurement of Erythrocyte Urea and Osmotic Water Permeabilities

Erythrocyte urea and water permeabilities were measured by stopped-flow light scattering using a Hi-Tech Sf-51 instrument (Wiltshire, UK). For measurement of urea permeability, dilutions of whole blood (mouse or human) in PBS (hematocrit ~0.5%) were incubated with test compounds for 5 min and then subjected to a 100-mM inwardly directed urea gradient. After an initial osmotic shrinking phase, the kinetics of increasing cell volume caused by urea influx was measured as the time-course of 90° scattered light intensity at 530 nm, with increasing cell volume producing reduced scattered light intensity. Urea permeability and percentage inhibition were computed as described (see, e.g., Levin et al., *FASEB J.* supra, 2007)). In some experiments, different urea gradients (25-200 mM) were used, or inhibitor was added only to the erythrocyte-containing or urea-containing solutions. In some experiments an outwardly directed urea gradient was used in which erythrocytes were incubated for 30 min with PBS containing specified urea and mixed in the stopped-flow apparatus with PBS. In reversibility experiments, erythrocytes were incubated for 30 min with inhibitor, washed three times to remove inhibitor, and urea transport assayed. Osmotic water permeability was measured using a 100 mM gradient of sucrose.

$UTB_{inh}$-14 Influx Kinetics in Erythrocytes $UTB_{inh}$-14 (2 µM) was added to 2% suspension of erythrocytes in PBS. At specified times 600-µL aliquots were removed and layered over 350 µL of silicone oil (density 1.05 g/mL) overlying 100 µL of 0.55 M sucrose in PBS (density 1.075 g/mL). Samples were spun for 30 s at 12,000 rpm to rapidly separate cells from supernatant. $UTB_{inh}$-14 was assayed in the cell pellet by liquid chromatography/mass spectrometry following ethyl acetate extraction as described herein.

Example 1

Identification of UT-B Inhibitors by High-Throughput Screening

One hundred thousand chemically diverse small molecules were screened in order to identify potent and selective inhibitors of UT-B that were suitable for efficacy studies in mice. Screening was performed using mouse erythrocytes, which strongly express UT-B and are highly water permeable because the cells also express aquaporin-1 (AQP1) water channels. The screening method involved assay of erythrocyte lysis in response to a large, outwardly directed gradient of acetamide, a urea analog that is transported efficiently by UT-B. A large, outwardly directed gradient of acetamide causes transient cell swelling, but little cell lysis, because UT-B-facilitated acetamide efflux limits water influx (see FIG. 1A). UT-B inhibition prevents acetamide efflux, allowing unopposed cell swelling and consequent cell lysis, which was recorded by reduced near-infrared light absorption at 710 nm. Acetamide, rather than urea or other urea analogs, was selected because its efflux occurs over a comparable time as osmotic equilibration in mouse erythrocytes, which increases assay sensitivity. The acetamide loading concentration to best resolve UT-B inhibition was determined empirically as 1.25 M, giving a Z'-factor for UT-B inhibitor screening of >0.6. Screening was done at a 25 µM concentration of test compounds based on initial studies showing a low percentage of active compounds.

Screening was carried out using a Beckman Coulter (Fullerton, Calif.) integrated system equipped with liquid handling robot (Biomek FX) and plate readers (FLUOstar Optima; BMG; Durham, N.C.), as described (see, e.g., Ma et al., *J. Biol. Chem.* 277:37235-41 (2002)). Primary screening was done using a collection of 100,000 diverse, drug-like compounds from commercial sources (ChemDiv, San Diego, Calif.; Asinex, Winston-Salem, N.C.). For assay of UT-B inhibition, whole blood was diluted to a hematocrit of approximately 1% in PBS containing 1.25 M acetamide and 5 mM glucose. 100 µL of the erythrocyte suspension was added to each well of a 96-well round-bottom microplate to which test compounds were added (1 µL, 25 µM compound concentration, 1% final DMSO). After 10 min incubation, 20 µL of the erythrocyte suspension was added rapidly to each well of a 96-well black-walled plate (Costar, Corning, N.Y.) containing 180 µL isosmolar buffer (PBS containing 1% DMSO). Vigorous mixing was achieved by repeated pipetting. Erythrocyte lysis was quantified by absorbance at 710 nm wavelength, made within 5 min after hypo-osmolar shock. Each assay plate contained eight negative 'no-lysis' controls (isotonic buffer; PBS+1.25 M acetamide with 1% DMSO) and eight positive 'full-lysis' controls (distilled $H_2O$). Percentage erythrocyte lysis was calculated using control values from the same plate as: % lysis=100%·$(A_{neg}-A_{test})/(A_{neg}-A_{pos})$, where $A_{test}$ is the absorbance value from a test well. For analysis of structure-activity relationships >900 commercially available analogs (ChemDiv and Asinex) were tested.

Primary screening yielded active inhibitors of mouse UT-B (>75% inhibition at 25 µM) in three chemical classes, which included two classes not previously identified (triazlothienopyrimidines and phthalazinamines) and benzenesulfonanilides (see FIG. 1B). A related benzenesulfonanilide ($UTB_{inh}$-201) was identified in a prior screen of 50,000 compounds (unrelated to the 100,000 compounds screened as described herein) for inhibitors of human UT-B (see, e.g., Levin et al., *FASEB J.* supra, 2007)). Screening of ~900 commercially available analogs of the three chemical classes revealed triazlothienopyrimidines with nanomolar potency for inhibition of UT-B. One compound, $UTB_{inh}$-14, was selected for further in vitro and in vivo characterization because of its low nanomolar potency for inhibition of mouse and human UT-B, and its high UT-B vs. UT-A selectivity.

Example 2

Synthesis of $UTB_{inh}$-14

$UTB_{inh}$-14 (also called compound 1 herein) was synthesized as a highly pure (>99% by HPLC) crystalline powder according to a synthesis scheme illustrated in FIG. 1C and described in greater detail below. The synthesis involved reaction of 3-bromothiophene-2-carbaldehyde 11a with sodium azide in DMSO to generate an azidothiophene carbaldehyde (Gronowitz et al., *Acta Chem. Scand. B* 29:224-32 (1975)), which was oxidized using the Lindgren reaction (see, e.g., Lindgren et al., *Acta Chem. Scand.* 27:888-90 (1973)) to generate 3-azidothiophene-2-carboxylic acid 13a Steglich esterification (Neises et al., *Angew Chem Int Ed* 17:522-24 (1978)) gave the azido ester intermediate 14a. Arylsulfonylacetonitrile intermediate 6m, was generated by alkylation of 4-ethylbenzenethiol with bromoacetonitrile followed by oxidation with mCPBA. Lactam 15m was then synthesized by base-mediated [2+3] cycloaddition of 14a and 6m, and converted to $UTB_{inh}$-14 using the PyBOP coupling reagent in the presence of thiophene-2-methylamine (see, e.g., Wan et al., *Org. Lett.* 8:2425-28 (2006)) by microwave irradiation.

3-Azidothiophene-2-carbaldehyde

3-Bromothiophene-2-carbaldehyde (1) (2000 mg, 10.47 mmol) was treated with sodium azide (1994 mg, 30.7 mmol) in DMSO (27 ml). The reaction was heated to 65° C. for 48 h in a sealed 40 mL vial. The reaction mixture was then taken up into $H_2O$ (35 mL) and extracted with diethyl ether (3×20 mL). The organic product layer was washed with 25 ml of saturated NaCl solution, dried over $Na_2SO_4$, and concentrated in vacuo to give 3-azidothiophene-2-carbaldehyde (1.22 g, 76% yield).

3-Azidothiophene-2-carboxylic acid (13a)

3-Azidothiophene-2-carbaldehyde (1.22 g, 8.0 mmol) was dissolved in 30 mL of acetone:$H_2O$ (2:1) and treated with sulfamic acid (1.16 g, 12.0 mmol). Sodium chlorite (1.27 g, 17.1 mmol) was added and stirred at 0° C. for 30 min. The mixture was alkalinized to pH 9 with sodium carbonate, and the product was washed with diethyl ether (10 mL). The aqueous layer was carefully treated with aqueous concentrated HCl to pH 1. The product was extracted with diethyl ether (3×10 mL), dried over $Na_2SO_4$, and concentrated in vacuo to give 13a (1.01 g, 75% yield).

Isobutyl-3-azidothiophene-2-carboxylate (14a)

Compound 13a (5.8 g, 34.3 mmol) was treated with 1-bromo-2-methylpropane (4.47 mL, 1.2 equiv.) and cesium carbonate (7.82 g, 0.7 equiv.) in anhydrous DMF (0.1 M) and heated to 80° C. for 6 h under argon. The mixture was cooled, dissolved in $H_2O$ (150 mL), and extracted with 1:1 diethyl ether:ethyl acetate (3×200 mL). The organic layer was washed with distilled $H_2O$ (5×100 mL), dried over $Na_2SO_4$, and concentrated in vacuo to give 14a as an oil (6.77 g, 77% yield).

3-(4-Ethyl-benzenesulfonyl)-4H-thieno[2,3-e][1,2,3]triazolo[1,5-a]pyrimidin-5-one (15m)

To a solution of compound 6m (0.71 g, 3.4 mmol, 1.5 equivalent) in anhydrous ethanol (22 mL) was added sodium ethoxide (1.54 g, 22.6 mmol, 10 equivalent). The reaction solution was stirred for 15 min followed by addition of azido ester 14a (0.51 g, 2.3 mmol) and the reaction mixture was further stirred for 3 h. Solid $NaHCO_3$ (4.75 g, 56.5 mmol) was added and the reaction mixture was taken up in $CHCl_3$ (100 mL), washed with aqueous HCl (1 M) (3×100 mL), concentrated in vacuo, and crystallized to give 15m (568 mg, 70%) as a white solid.

[3-(4-Ethyl-benzenesulfonyl)-thieno[2,3-e][1,2,3]triazolo[1,5-a]pyrimidin-5-yl]-thiophen-2-ylmethylamine ($UTB_{inh}$-14) (also called Compound 1 herein)

Pyrimidin-5-one 15m (560 mg, 1.55 mmol) was treated with 2-thiophenemethylamine (0.48 mL, 4.66 mmol, 3 equivalent), DBU (0.70 mL, 4.66 mmol, 3 equivalent) and PyBOP (2.43 g, 4.66 mmol, 3 equivalent) in anhydrous acetonitrile (5.1 mL), and placed in a microwave vessel. The mixture was heated in a microwave synthesizer at 100° C. for 30 min. The reaction mixture was treated with aqueous HCl (1 M, 20 mL) and stirred for 30 min before Na$_2$CO$_3$ was added to adjust pH to approximately 9. The reaction mixture was dissolved in CHCl$_3$ (75 mL), washed with aqueous HCl (1 M, 3×75 mL). The organic product layer was concentrated in vacuo and UTB$_{inh}$-14 was purified by flash column chromatography: dichloromethane+1% acetic acid→dichloromethane:methanol (100:1+1% acetic acid). The residue was re-crystallized from ethanol to yield UTB$_{inh}$-14 (392 mg, 55% yield) as a white solid. $^1$H NMR (CDCl$_3$, 500 MHz): δ 1.21 (t, 3H, J=10 Hz), 2.67 (q, 2H, J=10 Hz), 5.15 (d, 2H, J=5 Hz), 5.86 (t, 1H, J=5 Hz), 7.01 (dd, 1H, J=5 Hz), 7.23 (d, 1H, J=5 Hz), 7.26 (d, 1H, J=5 Hz), 7.28 (d, 2H, J=5 Hz), 7.88 (d, 1H, J=5 Hz), 7.95 (d, 1H, J=5 Hz), 8.12 (d, 2H, J=10 Hz). $^{13}$C NMR (CDCl$_3$, 125 Hz): δ 15.73, 29.55, 41.04, 118.13, 126.42, 127.89, 128.07, 128.64, 129.08, 133.84, 153.22. HR-ESI-MS (M+H)$^+$ calc 456.0622. found 456.0583 for C$_{20}$H$_{17}$N$_5$O$_2$S$_3$.

Example 3

Inhibition Potency of UTB$_{inh}$-14

Figure 2:
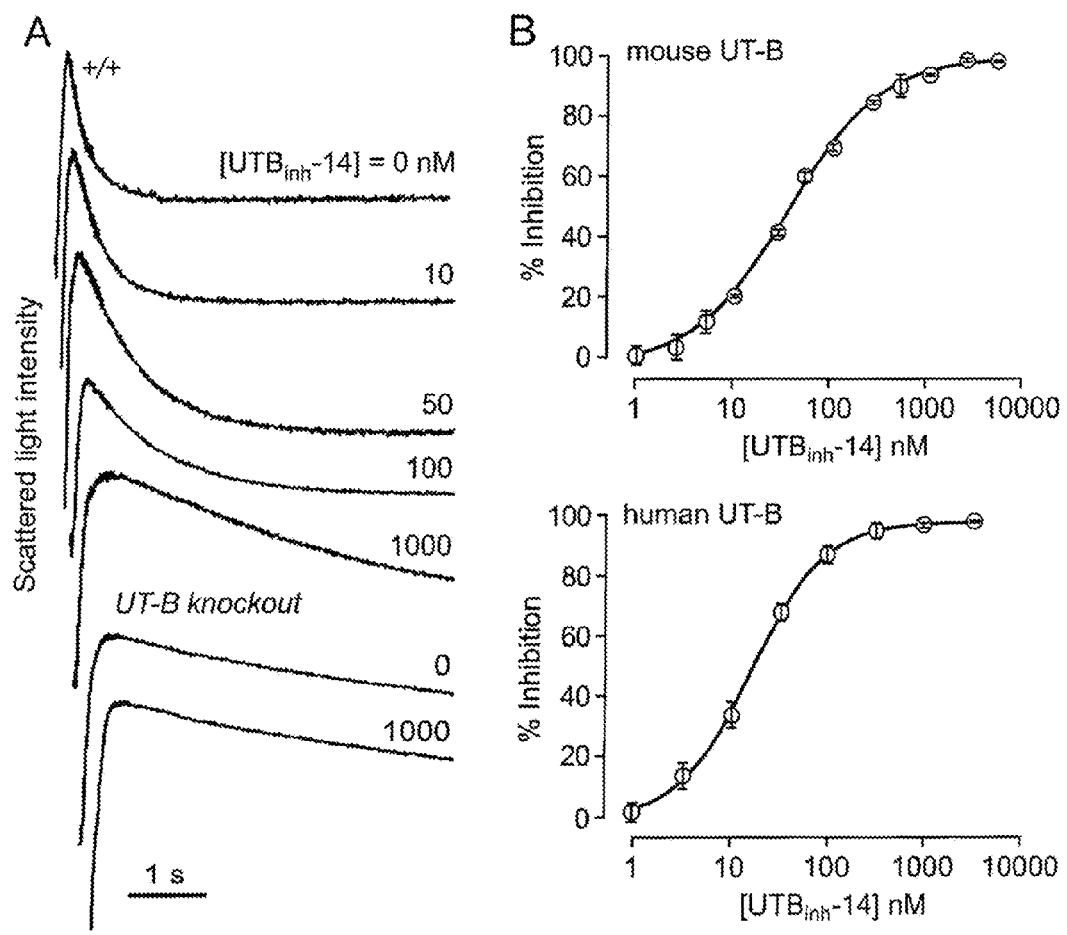
FIGS. 2A-2B illustrate that an exemplary triazolothienopyrimidine UT-B inhibitor, $UTB_{inh}$-14, exhibits nanomolar potency inhibition of UT-B urea transport.

UT-B inhibition potency was assayed quantitatively by stopped-flow light scattering from the kinetics of urea influx in response to an inwardly directed urea gradient (see Materials and Methods above). Rapid mixing of an erythrocyte suspension with an equal volume of a hyperosmolar, urea-containing solution to give a 100 mM inwardly directly urea gradient produced rapid cell shrinking due to osmotic water efflux, followed by cell swelling as a consequence of urea (and water) influx. FIG. 2A shows light scattering kinetics at different UTB$_{inh}$-14 concentrations, which was present in both the erythrocyte- and urea-containing solutions. Increasing UTB$_{inh}$-14 concentration greatly slowed the kinetics of erythrocyte swelling. UTB$_{inh}$-14 at 1 µM produced near 100% inhibition, as evidenced by the comparable swelling kinetics to that measured in erythrocytes from UT-B knock-out mice (lower curves). UTB$_{inh}$-14 did not inhibit urea transport in UT-B null erythrocytes, which is mediated by transport across the lipid bilayer by a solubility-diffusion mechanism. Concentration-inhibition data gave an IC$_{50}$ of 25.1 nM for mouse UT-B and 10.3 nM for human UT-B (see FIG. 2B).

Example 4

Inhibition Mechanism and Specificity of UTB$_{inh}$-14

Figure 3:
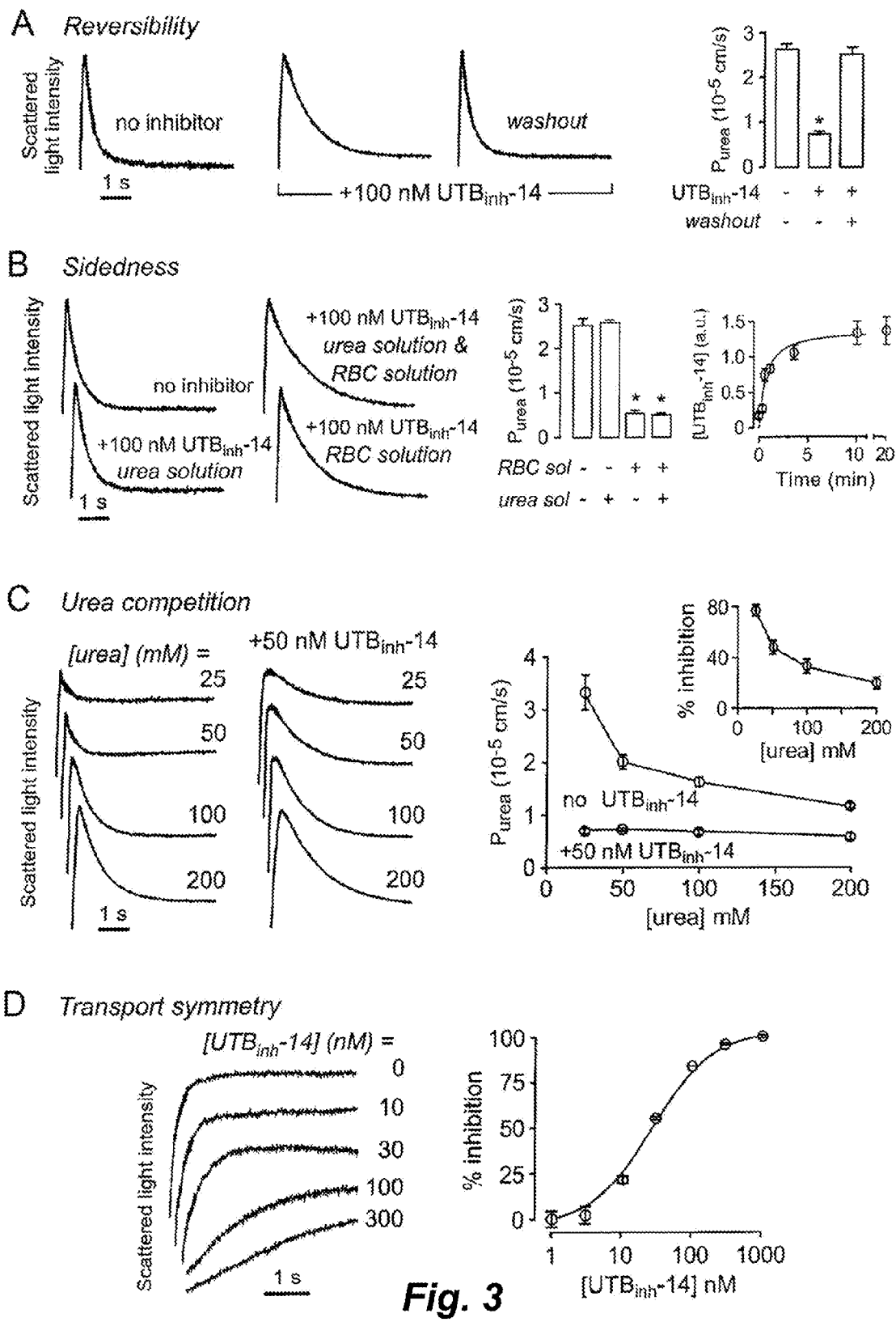
FIGS. 3A-3D provide experimental results that describe the mechanism of UT-B inhibition by $UTB_{inh}$-14.

FIG. 3A illustrates reversible UT-B inhibition by UTB$_{inh}$-14, as expected from the absence of reactive functional groups in the UTB$_{inh}$-14 chemical structure. Incubation of mouse erythrocytes with 100 nM UTB$_{inh}$-14, which reduced urea transport by approximately 75%, followed by washout, restored the original high urea permeability. To investigate the sidedness of UT-B inhibitor action, erythrocytes were exposed externally to UTB$_{inh}$-14 at a final concentration of 100 nM just at the time of stopped-flow measurement by inclusion of 200 nM UTB$_{inh}$-14 only in urea-containing solution. For comparison, measurements were made in which 100 nM UTB$_{inh}$-14 was included in both erythrocyte- and urea-containing solutions, and in which 100 nM UTB$_{inh}$-14 was included only in the erythrocyte-containing solution. FIG. 3B shows urea transport inhibition only when UTB$_{inh}$-14 was present in the erythrocyte-containing solutions, providing evidence for an intracellular site of action. UTB$_{inh}$-14 permeation into erythrocytes was rapid, though not instantaneous, as shown in FIG. 3B (right).

To investigate whether UTB$_{inh}$-14 competes with urea at a common binding site on the UT-B transporter, UTB$_{inh}$-14 inhibition efficacy was measured as a function of urea gradient. Measurements were done at UTB$_{inh}$-14 concentrations of 0 and 50 nM. FIG. 3C shows urea concentration-dependent reduction in UTB$_{inh}$-14 inhibition potency, suggesting a competitive mechanism for UTB$_{inh}$-14 inhibition of UT-B urea transport. To study transport inhibition symmetry, urea efflux was induced by pre-loading erythrocytes with 100 mM urea, which were then mixed in the stopped-flow apparatus with urea-free PBS. FIG. 3D shows slowed kinetics of urea efflux with increasing UTB$_{inh}$-14 concentration, with IC$_{50}$ of 26.7 nM, similar to that of 25.1 for UTB$_{inh}$-14 inhibition urea influx as shown in FIG. 2B.

Example 5

Computational Modeling of UTB$_{inh}$-14 and the UT-B Protein

A homology model of human UT-B was generated using the SWISS MODEL online utility (see Internet web site: swissmodel.expasy.org) in automated mode, using the sequence of the full human UT-B1 protein (see, e.g., GenBank Accession No. CAB60834). Residues 43 to 378 were modeled, based a urea transporter from *Desulfofibrio vulgaris* (PDB code 3M6E) (see, e.g., Levin et al., *Nature*, supra (2009)). UTB$_{inh}$-14 was drawn in ChemDraw (Cambridge Software, Cambridge, Mass.), converted to a SMILES strings, transformed to a 3D conformation, and minimized using PIPELINE PILOT (Accelrys, San Diego, Calif.). The single conformation was passed through MOLCHARGE (OpenEyes, Santa Fe, N. Mex.) to apply AM1BCC charges, and through OMEGA (OpenEyes) to generate a multi-conformational library for UTB$_{inh}$-14. The UT-B protein was prepared for docking using the FRED-RECEPTOR (OpenEyes) utility, employing the homology model of human UT-B. The receptor site was generated using a 12 cubic Å box. Docking was performed using FRED (v2.2.5) (OpenEyes), which was configured to employ consensus scoring functions ChemGauss3, OEChemScore, ScreenScore, PLP, and ZapBind. Docking of the inhibitor was carried out free of pharmacophore restraint. Each final pose was minimized by FRED by molecular dynamics using the MMFF94 force field within the active site. The final protein-ligand complex was visualized using PYMOL (Schrödinger, San Diego, Calif.).

Figure 4:
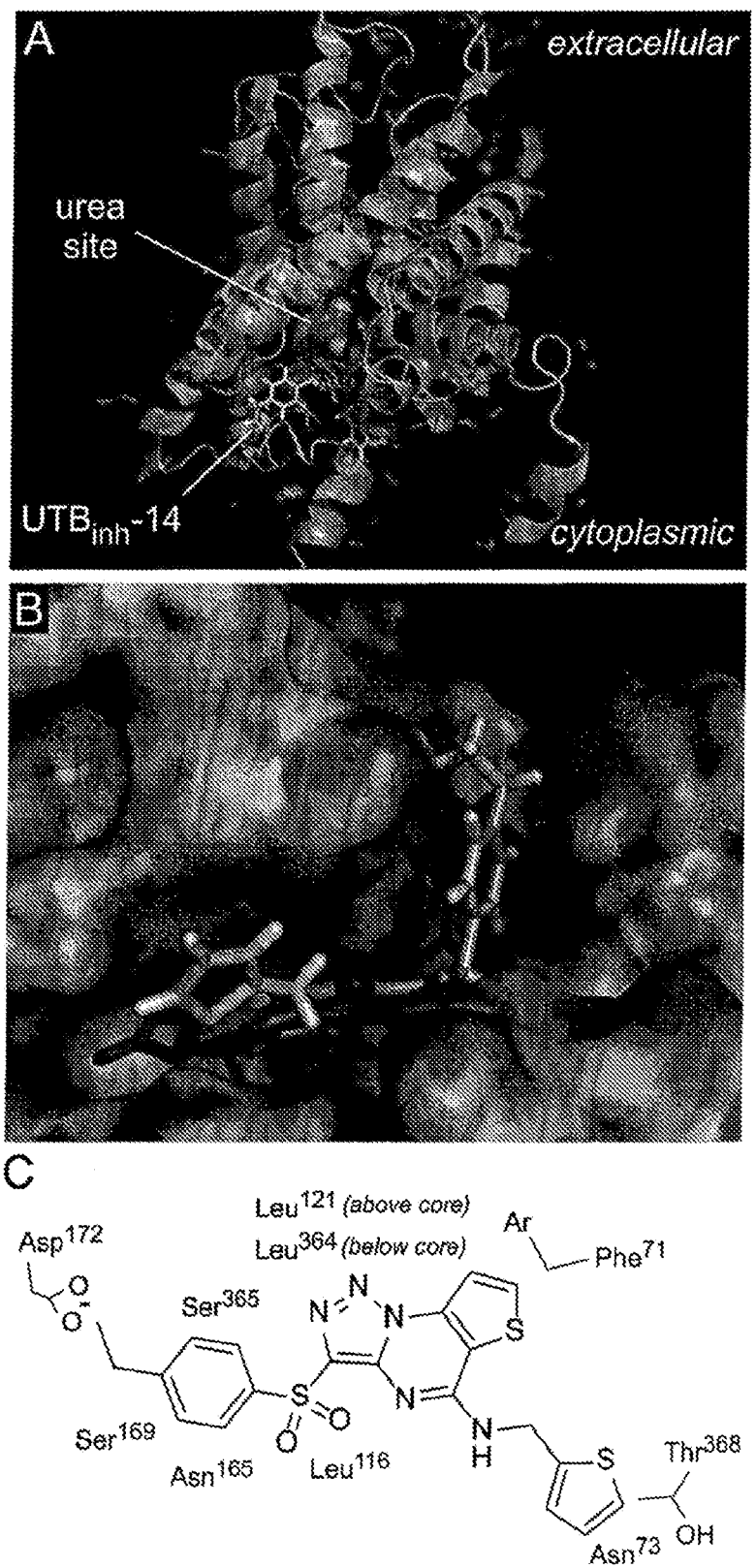
FIGS. 4A-4C present docking of $UTB_{inh}$-14 in a homology structural model of human UT-B.

The putative site of UTB$_{inh}$-14 binding to the UT-B protein was determined by docking computations following homology modeling of the human UT-B structure based on crystal structure data for a bacterial urea transporter homolog as shown in FIG. 4A (see, e.g., Levin, *Nature*, supra). The predicted UTB$_{inh}$-14 binding site was in a centrally located groove in the channel used for urea transport (see FIG. 4B). This location is consistent with the data above (see Example 4) showing urea competition and an intracellular site of action of UTB$_{inh}$-14. FIG. 4C summarizes the key interactions predicted by the model. Most of the interactions involve hydrophobic and neutral-polar amino acids in the binding pocket: Leu-121, Leu-364, Phe-71, Thr-368, Leu-116, Asn-165, Ser-169 and Ser-365.

Example 6

Selectivity of UTB$_{inh}$-14 for UT-B Protein and Compound Cytotoxicity Study UT-B selectivity and cytotoxicity were studied. Because of sequence similarities between UT-B and UT-A isoforms, UT-A inhibition was measured. Transepithelial urea transport was measured in MDCK cells stably expressing UT-A1, UT-A3, and UT-B. UT-A1 and UT-A3 are cAMP-regulated urea transporters expressed in kidney tubule epithelia (see, e.g., Frohlich et al., *Am. J. Physiol. Cell Physiol.* 291:C600-606 (2006); Tickle et al., *Am. J. Physiol. Regul. Integr. Comp Physiol* 0.297: R323-329 (2009); Stewart et al., *Am. J. Physiol. Renal Physiol.* 292:F1157-63 (2006)). MDCK cells were cultured on collagen-coated porous filters for measurement of urea accumulation in the apical solution following addition of urea to the basolateral solution.

Urea Transport Across MDCK Cell Monolayers.

cDNAs encoding mouse UT-A3 and UT-B were cloned into pcDNA3.1 and used to generate stably transfected MDCK cell lines. MDCK cells stably expressing rat UT-A1 (MDCK-UT-A1) (see, e.g., Frohlich et al., supra) were obtained as described (see, e.g., Levin et al., *FASEB J.*, supra). Cells were cultured in DMEM containing 10% FBS and 0.5 mg/mL G418. Cells were grown on 12-mm collagen-coated Transwell inserts (0.4 μm pore size; Costar) in 12-well plates and used after culture for 4 days (transepithelial resistance 500-600 Ω·cm²). Urea flux in the basolateral-to-apical direction across unstimulated and forskolin-stimulated cell layers was measured in response to a 15-mM urea gradient. Cultures were preincubated for 30 min at 37° C. with DMSO vehicle or forskolin, with or without UT-B inhibitor, in both the apical-facing (0.2 mL) and basal-facing (1 mL) solutions. The basal-facing solution was replaced with PBS containing 15 mM urea. Five-μL aliquots of apical fluid were collected at specified times for assay of urea concentration (QUANTICHROM™ Urea Assay Kit, Bioassay System, Hayward, Calif.).

Figure 5:
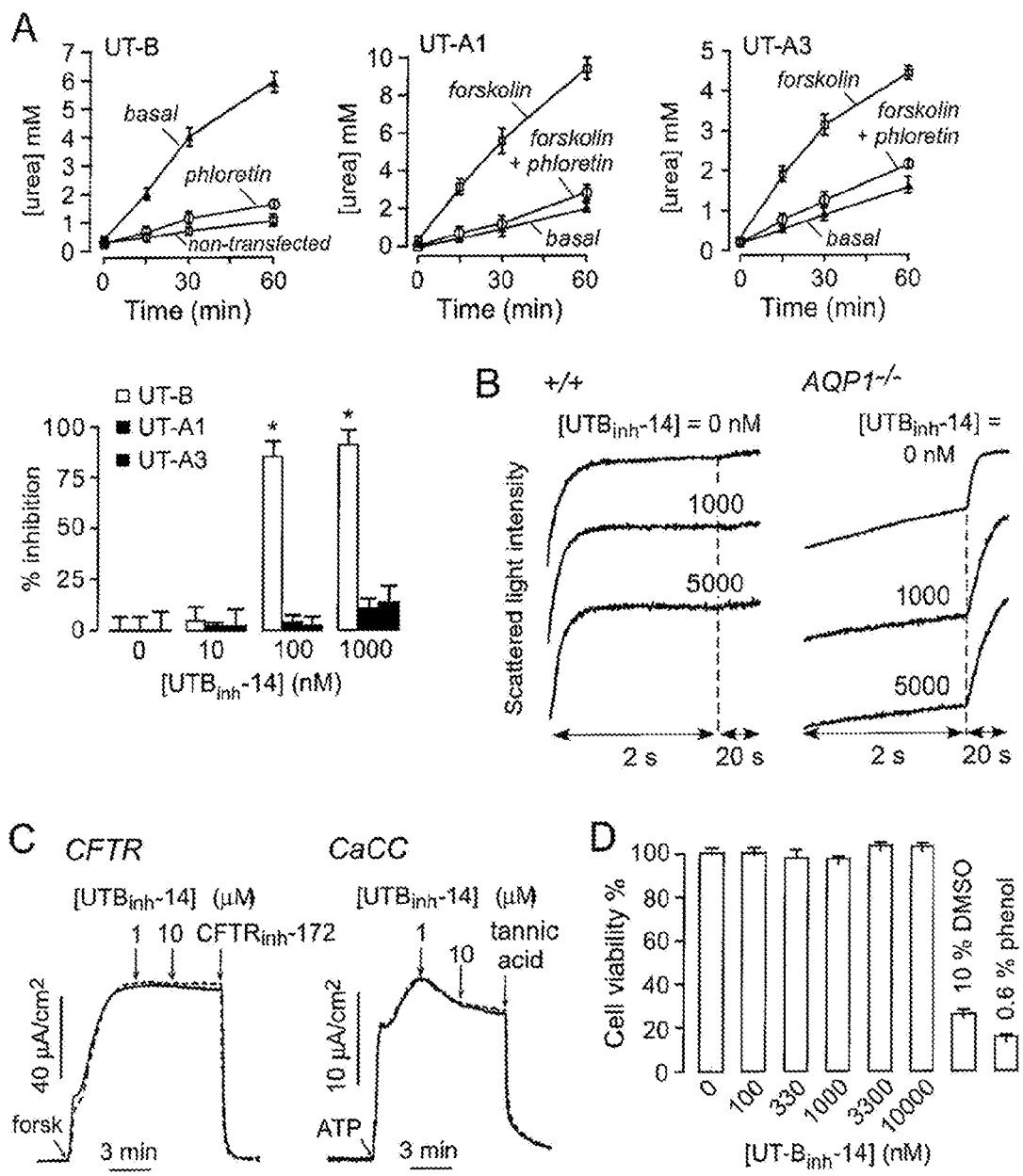
FIGS. 5A-5D show results of experiments for determining $UTB_{inh}$-14 transport specificity and cellular toxicity.

FIG. 5A (top panels) shows increased urea permeability in each of the transfected cell lines. Increased urea permeability by UT-A1 and UT-A3 required forskolin, whereas UT-B did not. UT-facilitated urea transport was inhibited for phloretin. FIG. 5A (bottom) shows little inhibition of UT-A1 and UT-A3 facilitated urea transport by UTB$_{inh}$-14 under conditions in which UT-B facilitated urea transport was strongly inhibited, indicating high specificity for UT-B. Without wishing to be bound by any particular theory, a possible explanation for this specificity is that UT-B encodes a Leu residue at position 116, while UT-A1 encodes an Ala at the corresponding position, 176, as do UT-A2 and UT-A3. As seen in the docking model (FIG. 4C), Leu-116 presents a surface at the binding site of the central sulfone functional group in the inhibitor, which might account for the specificity of UTB$_{inh}$-14 for UT-B over UT-A isoforms.

Effects of UTB$_{inh}$-14 on water (AQP1) and chloride (CFTR and TMEM16A) transport were also measured because these transporters often co-localize with urea transporters. Erythrocyte osmotic water permeability was measured by stopped-flow light scattering. As noted in a previous report, approximately 90% of water transport in erythrocytes is mediated by AQP1, approximately 8% by UT-B, and the remainder through the lipid bilayer (see, e.g., Yang et al., *J. Biol. Chem.* 277:36782-86 (2002). FIG. 5B (left) shows no significant inhibition of water transport in erythrocytes from wild type mice, indicating that UTB$_{inh}$-14 does not inhibit AQP1. However, UTB$_{inh}$-14 inhibited water transport significantly in AQP1-null erythrocytes (FIG. 5B, right), supporting a prior conclusion that erythrocyte water transport is mediated, in part, by UT-B (see, e.g., Levin et al. *Nature*, supra; Meng et al., *Sci. China C. Life Sci.* 52:474-78 (2009)). FIG. 5C shows no significant inhibition of CFTR or TMEM16A chloride conductance by 10 μM UTB$_{inh}$-14, as measured by short-circuit current. Last, by MTT assay, incubation of MDCK cells with UTB$_{inh}$-14 up to 10 μM for 24 h (where it remains soluble) showed no cytotoxicity (FIG. 5D).

Chloride Conductance and Cytotoxicity.

CFTR chloride conductance was measured by short-circuit current analysis in Fisher rat thyroid (FRT) cells stably expressing CFTR, as described (see, e.g., Ma et al., *J. Biol. Chem.* (2002), supra). CFTR chloride conductance was stimulated by forskolin and inhibited by a thiazolidinone compound that inhibits CFTR (CFTR$_{inh}$-172). TMEM16A calcium-activated chloride conductance was measured by short-circuit current analysis in FRT cells stably expressing TMEM16A, as described (see, e.g., Namkung et al., *J. Biol. Chem.* 286:2365-2374, 2011. TMEM16A was stimulated by ATP and inhibited by tannic acid (100 μM). Cytotoxicity was measured in MDCK using the MTT assay [3(4,5-dimethyl-thiazol-2-yl)-2,5-diphenyl tetrazolium bromide] by standard procedures.

Example 7

Reduction of Urinary Concentration by UTB$_{inh}$-14 In Vivo

UTB$_{inh}$-14 was formulated at 1 mg/ml in 5% DMSO, 2.5% TWEEN-80 and 2.5% PEG400 in H$_2$O, based on formulations used for compounds of similar polarity and chemical properties (see, e.g., Strickley, *Pharm. Res.* 21:201-30 (2004)). Male mice (wild type or UT-B knockout) in a CD1 genetic background (age 8-10 weeks, 25-35 g) were administered 300 μL of the UTB$_{inh}$-14 formulation or formulation alone by intraperitoneal injection. Urine samples were collected by placing mice on a wire mesh platform in a clean glass beaker during food and water deprivation. dDAVP ([1-deamino-8-D-arginine]-vasopressin, 1 μg/kg) was given 1 h after UTB$_{inh}$-14. In some studies, mice were placed on low, normal or low-protein diets (4%, 20% or 40% casein, Harlan Labs.) for 1 week prior study of dDAVP effects. Urine osmolality was measured in water-diluted urine samples by freezing-point osmometry (Micro-osmometer; Precision Systems, Natick, Mass.). Urea concentration was determined by a colorimetric enzymatic assay as described above. Measurements were also done in the absence of dDAVP in which urine was collected during free access to food and water.

To investigate the efficacy of UTB$_{inh}$-14 in reducing maximum urinary concentration in mice in vivo, a formulation to deliver UTB$_{inh}$-14 was established that gave predicted therapeutic concentration of UTB$_{inh}$-14 in mouse kidneys for several hours following a single administration. Several vehicles and administration routes were tested; intraperitoneal administration of UTB$_{inh}$-14 in 5% DMSO, 2.5% Tween-80 and 2.5% PEG-400 gave target UTB$_{inh}$-14 concentration in kidneys and urine.

Liquid Chromatography/Mass Spectrometry.

A quantitative LC/MS assay was developed to measure [UTB$_{inh}$-14] in kidney homogenates in which UTB$_{inh}$-14 was extracted in an organic phase, concentrated, separated by reverse-phase HPLC, and detected by gated electrospray mass spectrometry. Kidneys from UTB$_{inh}$-14-treated (or control) mice were rapidly removed after renal arterial perfusion with PBS. Kidneys were weighed, mixed with acetic acid (100 μL per 1 g tissue) and ethyl acetate (10 mL per 1 g tissue), and homogenized. The homogenate was centrifuged at 3,000 rpm for 15 min at room temperature. Calibration standards were prepared in kidney homogenates from control mice to which was added known amounts of $UTB_{inh}$-14. The ethyl acetate-containing supernatant was dried under nitrogen and the residue was reconstituted in acetonitrile:$H_2O$ (3:1) containing 0.1% formic acid. $UTB_{inh}$-14 recovery from kidney homogenates was ~85%. Reverse-phase HPLC was carried out using a XTERRA MS C18 column (2.1×100 mm, 3.5 μm particle size; Waters, Milford, Mass.) connected to a solvent delivery system (model 2690; Waters). The solvent system consisted of a linear gradient from 5% to 95% acetonitrile containing 0.1% formic acid over 16 min (0.2 mL/min flow). $UTB_{inh}$-14 was detected by absorbance at 262 nm. Mass spectra were acquired on a mass spectrometer (Alliance HT 2790+ZQ; Waters) using positive ion detection. For analysis of blood and urine, fluids were diluted with equal volume of water and extracted with ethyl acetate.

Figure 6:
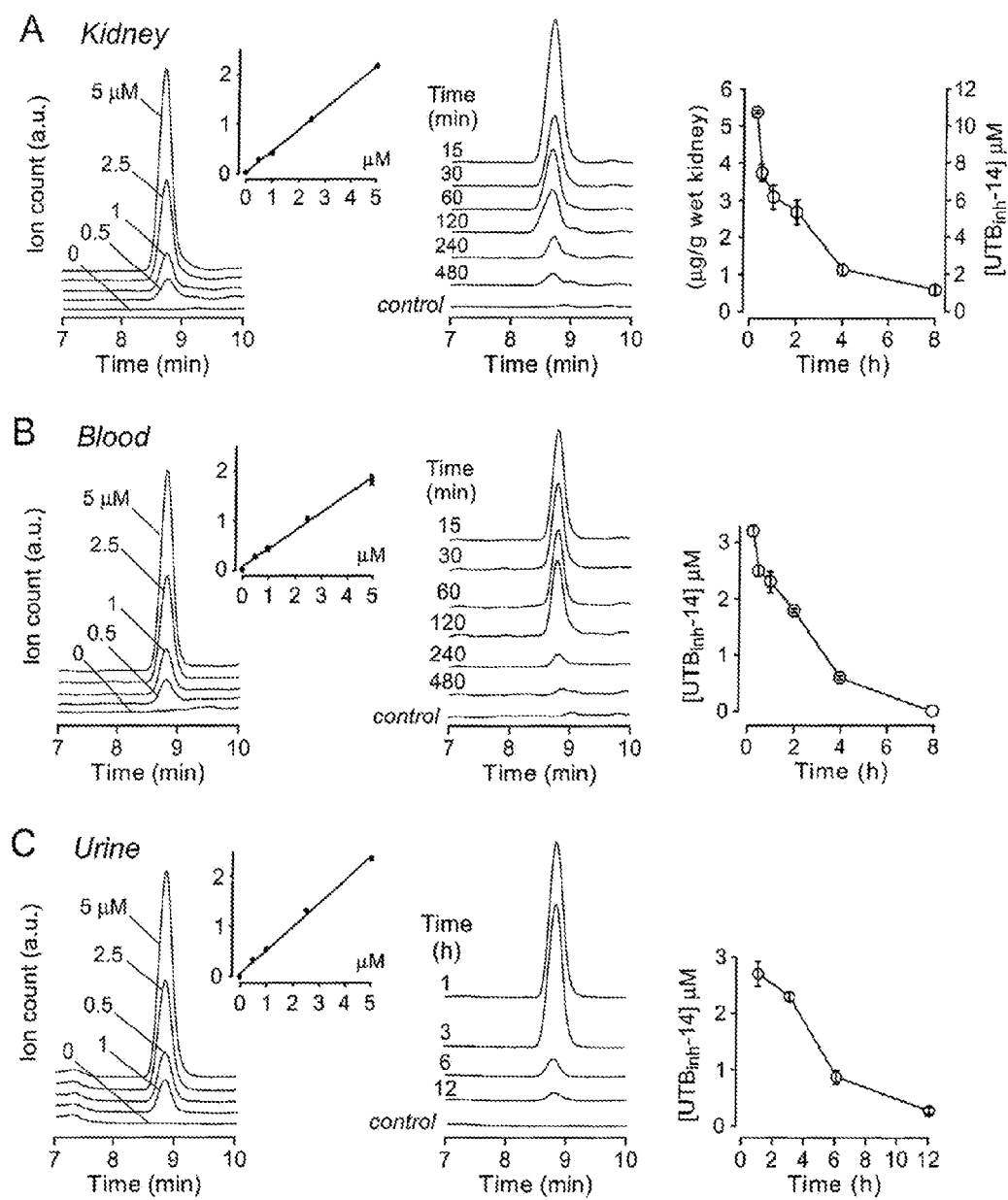
FIGS. 6A-6C present LC/MS analysis of $UTB_{inh}$-14 in mouse kidney, blood and urine.

FIG. 6A (left) showed ion current chromatograms and the deduced linear assay response, in which known amounts of $UTB_{inh}$-14 were added to kidney homogenates. FIG. 6A (right) shows the kinetics of $UTB_{inh}$-14 in kidney following a single intraperitoneal injection of $UTB_{inh}$-14 using the above-described formulation. Peak [$UTB_{inh}$-14] was approximately 10 μM (normalized to kidney water volume) and remained greater than 1 μM for at least 4 h, well above the $IC_{50}$ for UT-B inhibition in vitro. $UTB_{inh}$-14 was similarly assayed in blood and urine following intravenous administration (see FIGS. 6B and 6C). $UTB_{inh}$-14 concentration was greater than 1 μM in blood and urine for several hours following a single intraperitoneal administration.

Figure 7:
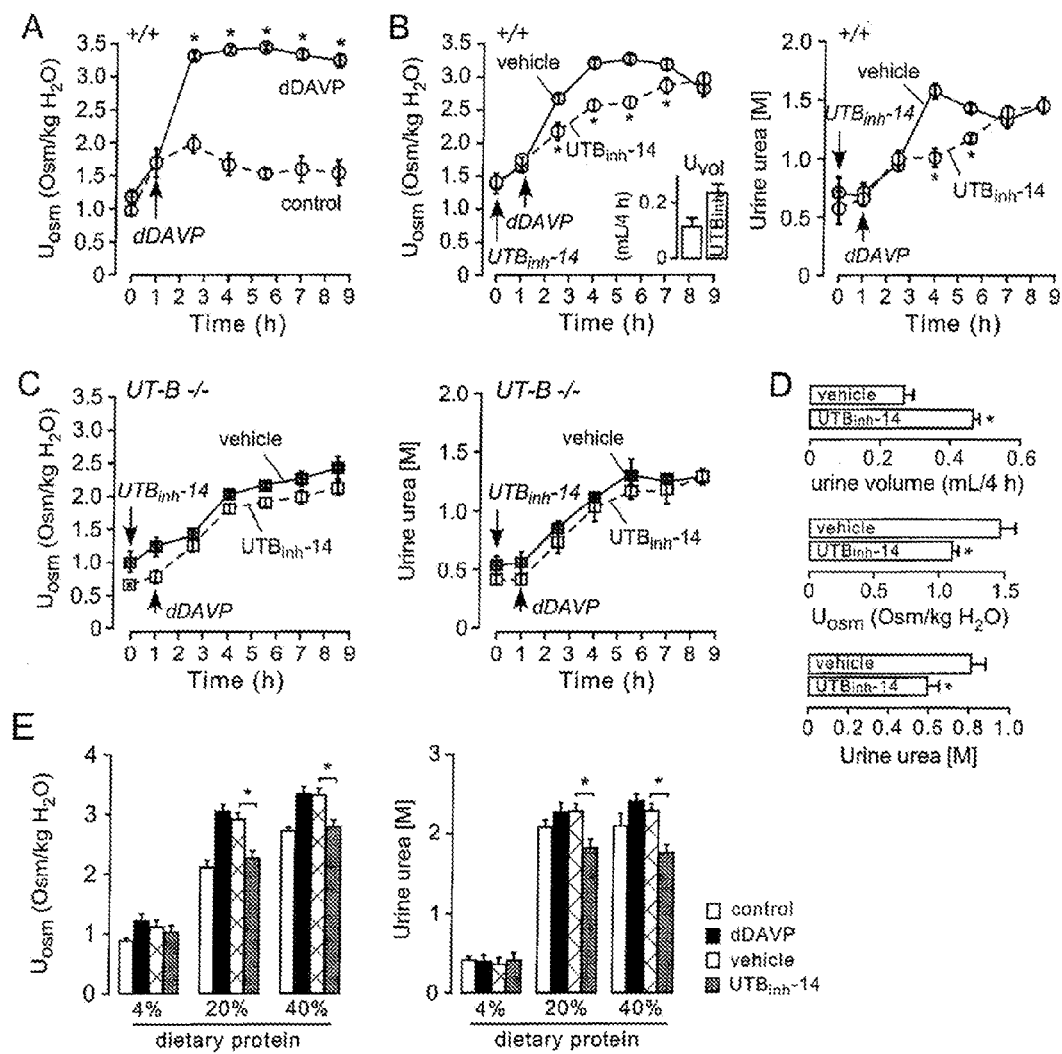
FIG. 7A-E illustrate that $UTB_{inh}$-14 reduces urinary concentration in mice.

UT-B gene disruption in mice reduces maximum urinary concentrating ability (see, e.g., Yang et al., *J. Biol. Chem.*, supra, (2002)). To study $UTB_{inh}$-14 effect on maximum urinary concentration, mice were administered 300 μg $UTB_{inh}$-14 (or formulation (vehicle) control) followed 1 h later by the $V_2$-receptor agonist dDAVP. FIG. 7A shows a stable, high urine osmolality of >3000 mosm/kg $H_2O$ over several hours following dDAVP administration. FIG. 7B (left) shows a similar, through slower response in mice receiving control formulation (lacking $UTB_{inh}$-14) before dDAVP, probably because of the osmotic load. Urine osmolality was significantly reduced by inclusion of $UTB_{inh}$-14 in the formulation. The inset in FIG. 7B shows urine volume in 4-hour collections from a separate set of studies. $UTB_{inh}$-14 did not significantly reduce urine osmolality or urea concentration in UT-B knockout mice (FIG. 7C), with values similar to those in $UTB_{inh}$-14-treated wild-type mice. Under baseline conditions, in mice given free access to food and water and in the absence of dDAVP, $UTB_{inh}$-14 significantly increased urine volume and reduced urine osmolality and urea concentration (see FIG. 7D). Last, the effects of $UTB_{inh}$-14 on dDAVP-stimulated urinary concentration were measured in mice placed for 1 week on low, normal and high-protein diets. FIG. 7E shows little effect of $UTB_{inh}$-14 in mice on a low-protein diet, where urine concentration was low, but a robust effect of $UTB_{inh}$-14 in mice on a high-protein diet.

Example 8

Synthesis of Aryl Sulfonyl Acetonitrile Building Blocks

In general, the following information applies to compounds synthesized and characterized in this example and in the following examples.

Chemistry:

All solvents used in reactions were anhydrous and obtained from commercial sources unless otherwise specified. $^1H$ and $^{13}C$ NMR spectra were recorded on a Bruker DRX 300 MHz or Bruker Avance 500 MHz spectrometer. $^1H$ NMR chemical shifts are relative to TMS (δ=0.00 ppm) or $CDCl_3$ (δ=7.26 ppm). $^{13}C$ NMR chemical shifts are relative to $CDCl_3$ (δ=77.23 ppm). Low-resolution LCMS was performed using a Waters Micromass ZQ instrument, or an Agilent-1100 HPLC equipped with an Agilent 1956B mass spectrometer. High-resolution mass spectra were obtained by the University of Notre Dame Mass Spectrometry & Proteomics Facility (Notre Dame, Ind. 46556-5670) using ESI either by direct infusion on a Bruker micrOTOF-II or by LC elution via an ultra-high pressure Dionex RSLC with C18 column coupled with a Bruker micrOTOF-Q II. Microwave-assisted organic synthesis was performed using a Biotage Isolera instrument. Commercial triazolothienopyrimidine analogues were purchased from ChemDiv (San Diego, Calif.). The reactants and intermediates described in the following chemistry examples are outlined in the synthesis schematics 1-4 described herein in the Detailed Description.

General Conditions for Conversion of Substituted Aryl Thiols (4) to Substituted Aryl Sulfonyl Acetonitriles (6).

Bromoacetonitrile was dissolved in DMF (0.4M), stirred in an ice bath, and then treated with substituted benzenethiol (4) (0.95 eq) and $K_2CO_3$ (2 eq), and allowed to stir for two hours at 0° C. The reaction mixture was taken up into excess $H_2O$ and extracted 3 times with $Et_2O$. The combined organic extracts were washed twice with water and NaCl (satd. aq), followed by concentration in vacuo to generate the intermediate aryl sulfide acetonitrile (5) compound in approximately 90% yield. The sulfide was then dissolved in DCM (0.4 M) and treated with mCPBA (77% peroxybenzoate, 2 eq). The reaction was stirred at 0° C. under argon for 2 h to give complete conversion by TLC. The reaction mixture was quenched with excess sodium sulfite solution, and extracted twice with DCM; the organic layer was washed by brine, dried over $Na_2SO_4$, and concentrated in vacuo to generate 6.

(4-isopropylbenzenesulfonyl)-acetonitrile (6a)

(1.5g). White solid, yield over two steps 76%. $^1H$ NMR ($CDCl_3$, 500 MHz): δ 1.31 (d, J=5 Hz, 6H), 3.01-3.07 (mult, 1H), 4.04 (s, 2H), 7.50 (d, J=5 Hz, 2H), 7.95 (d, J=5 Hz, 2H).

(4-trifluoromethylbenzenesulfonyl)-acetonitrile (6b)

Reaction mixture was purified by flash column chromatography using hexanes:ethyl acetate (3:1); yield over two steps 18%. $^1H$ NMR ($CDCl_3$, 300 MHz): δ 4.10 (s, 2H), 7.94 (d, J=9 Hz, 2H), 8.20 (d, J=6 Hz, 2H). This compound is available commercially.

(4-trifluoromethoxybenzenesulfonyl)-acetonitrile (6c)

Colorless solid, yield over two steps 62%. $^1H$ NMR ($CDCl_3$, 300 MHz): δ 4.08 (s, 2H), 7.49 (d, J=9 Hz, 2H), 8.12 (d, J=9 Hz, 2H). $^{13}C$ NMR ($CDCl_3$, 75 Hz): δ 34.1, 46.5, 121.9, 132.1. This compound is available commercially.

(4-methoxybenzenesulfonyl)-acetonitrile (6d)

Colorless solid, yield over two steps 38%. $^1H$ NMR ($CDCl_3$, 300 MHz): δ 3.92 (s, 3H), 4.03 (s, 2H), 7.10 (d, J=9

Hz, 2H), 7.97 (d, J=9 Hz, 2H). $^{13}$C NMR (CDCl$_3$, 75 Hz): δ 46.7, 56.5, 115.7, 131.9, 163.4. This compound is available commercially.

(thiophene-2-sulfonyl)-acetonitrile (6e)

Colorless solid, yield over two steps 56%. $^1$H NMR (CDCl$_3$, 300 MHz): δ 4.17 (s, 2H), 7.28 (t, J=3 Hz, 1H), 7.89-7.90 (mult, 1H), 7.91-7.93 (mult, 1H). $^{13}$C NMR (CDCl$_3$, 75 MHz): δ 47.7, 129.3, 137.3, 137.5. This compound is available commercially.

(4-fluorobenzenesulfonyl)-acetonitrile (6f)

(1.7g). Colorless solid, yield over two steps 50%. $^1$H (CDCl$_3$, 500 MHz): δ 4.07 (s, 2H), 7.35-7.36 (mult, 2H), 8.06-8.09 (mult, 2H). $^{13}$C NMR (CDCl$_3$, 125 Hz): δ 46.6, 111.0, 118.0, 132.7, 135.8, 168.6. [jz4_77, 1.7 g remaining] The substance is available commercially.

(4-bromobenzenesulfonyl)-acetonitrile (6g)

White solid (yield over two steps 19%). $^1$H NMR (CDCl$_3$, 500 MHz): δ 4.06 (s, 2H), 7.82 (d, J=10 Hz, 2H), 7.90 (d, J=10 Hz, 2H). $^{13}$C NMR (CDCl$_3$, 125 Hz): δ 46.5, 110.9, 131.1, 132.1, 134.0, 136.2. This compound is available commercially.

[4-(1,1-Difluoro-ethyl)-phenylsulfanyl]-acetic acid methyl ester (9h)

1-Bromo-4-(1,1-difluoro-ethyl)-benzene (7h) (1000 mg, 4.52 mmol, 1.00 eq) was treated with mercapto-acetic acid methyl ester (0.809 ml, 9.05 mmol, 2.00 eq) in 1,4-dioxane (45 ml) and N-ethyldiisopropylamine (1.495 ml, 9.05 mmol, 2.0 eq), tetrakis(triphenylphosphine)-palladium(0) (523 mg, 0.45 mmol, 0.1 eq), 9,9-dimethyl-4,5-bis(diphenylphosphino)xanthene (451.2 mg, 0.91 mmol, 0.2 eq). The reaction was heated at 135° C. under argon for 16 h. After cooling to room temperature, the mixture was filtered and the filtrate was concentrated under reduced pressure. The mixture was purified by flash column chromatography eluting with hexanes:EtOAc (6:1) to afford the sulfide (8h), crude yield 99%. The sulfide (1084 mg, 4.40 mmol) was dissolved in DCM (44 ml) and oxidized by treatment with mCPBA (4341 mg, 17.61 mmol, 4.0 eq) at 0° C. for 2h. The reaction mixture was taken up in DCM (150 ml), and was then washed with NaSO$_3$ (aq. 5%) (3×50 ml). The organic layer was washed with NaCl (satd. aq) and dried over anhydrous NaSO$_4$ to generate the product as a colorless oil. $^1$H NMR (CDCl$_3$, 500 MHz): δ 1.97 (t, J=15.0 Hz, 3H), 3.74 (s, 3H), 4.16 (s, 2H), 7.74 (d, J=5.0 Hz, 2H), 8.04 (d, J=10.0 Hz, 2H). $^{13}$C NMR (CDCl$_3$, 125 MHz): δ 25.9 (t, J=28.8 Hz), 53.4, 61.1, 126.0 (t, J=6.3 Hz), 129.2, 134.6, 144.3, 162.9. ESI(+)-HRMS [M+Na]$^+$ calculated 301.0322, observed 301.0319 for C$_{11}$H$_{12}$F$_2$O$_4$S.

[4-(1,1-Difluoro-ethyl)-benzenesulfonyl]-acetonitrile (6h)

The precursor methyl ester (9h) (1232 mg, 4.43 mmol, 1.0 eq) was treated with NH$_3$ (7N in MeOH) (15 ml, 132.8 mmol, 30 eq) in the presence of catalytic NaCN (0.71 mg, 0.44 mmol, 0.1 eq) in a sealed vial, and heated at 50° C. for 16 h. After extraction with DCM and washing with NaCl (satd. aq) the solvent was removed under vacuum. The crude product was washed by ether, and subjected to vacuum filtration to generate the primary amide (10h) which was used directly without purification or characterization. This material (500 mg, 1.90 mmol, 1.0 eq) was dehydrated with phosphorous pentoxide (16175 mg, 56.98 mmol, 30 eq) in toluene (95 ml) at 75° C. for 1h. The reaction mixture was added to ice water (300 ml) and then extracted with DCM (200 ml). The aqueous layer was extracted by additional DCM (3×50 ml), and the final organic layer was dried over NaSO$_4$. Flash column chromatography was performed to purify the crude product, eluting with hexane:EtOAc (3:1) to yield the aryl sulfonyl acetonitrile target compound (6h) as white needle-like crystals. (145.90 mg, yield 31%). $^1$H NMR (CDCl$_3$, 300 MHz): δ 1.97 (t, J=18.0 Hz, 3H), 4.08 (s, 1H), 7.80 (d, J=9.0 Hz, 2H), 8.12 (d, J=6.0 Hz, 2H). $^{13}$C NMR (Acetone-d$_6$, 75 MHz): δ 24.6 (t, J=29.3 Hz), 44.7, 111.2, 126.1 (t, J=6.0 Hz), 129.2, 139.1, 144.2 (t, J=26.3 Hz). ESI(+)-HRMS [M+Na]$^+$ calculated 301.0322, observed 301.0319 for C$_{11}$H$_{12}$F$_2$O$_4$S.

Example 9

Coupling of Substituted Aryl Sulfonyl Acetonitriles with Azido Thiophene Ester to Generate Cycloadduct General Conditions for Coupling of Substituted Aryl Sulfonyl Acetonitriles (6a-h) with Azido Thiophene Ester (14a) to Generate Cycloadduct (15a-h).

Sodium ethoxide (2 mmol scale typically, 10 eq based on starting material 14a) was dissolved in absolute EtOH (0.3M), and then a substituted aryl sulfonyl acetonitrile (6) was added (1.5 eq based on 14a) and stirred for 15 min at RT. Next, the 3-azidothiophene ester starting material (14a) was added (1.0 eq), and stirred for 30 min at RT. TLC and HPLC analysis confirmed the consumption of SM and formation of product. Solid NaHCO$_3$ (25 eq) was added to neutralize the excess alkoxide base, and the reaction mixture was taken up into CHCl$_3$ and washed by HCl (1M aq., three times). The organic was typically purified by crystallization with chloroform, additional purification techniques may be listed for the specific examples below.

3-(4-isopropylbenzenesulfonyl)-4H-thieno[2,3-e][1,2,3]triazolo[1,5-a]pyrimidin-5-one (15a)

The crude mixture was purified by flash column chromatography, using pure DCM [+Et$_3$N (1%)]→DCM:MeOH [50:1 plus Et$_3$N (1%)]. Yellow solid, yield 15%. $^1$H NMR (DMSO-d$_6$, 300 MHz): δ 1.16 (d, J=6 Hz, 6H), 2.93-3.07 (mult, 1H), 7.25 (d, J=6 Hz, 1H), 7.42 (d, J=9 Hz, 2H), 7.94 (d, J=9 Hz, 2H), 8.05 (d, J=6 Hz, 1H). This compound is available commercially. ESI(+)-HRMS [M+H]$^+$ calculated 375.0585, observed 375.0574 for C$_{16}$H$_{14}$N$_4$O$_3$S$_2$.

3-(4-trifluoromethylbenzenesulfonyl)-4H-thieno[2,3-e][1,2,3]triazolo[1,5-a]pyrimidin-5-one (15b)

The reaction mixture is purified by flash column chromatography, using pure DCM [+1% Et$_3$N]→DCM:MeOH [50:1 plus TEA (1%)]. The combined fractions were taken up into CHCl$_3$ and washed by (1M, twice). White solid, yield 5%. $^1$H NMR (CDCl$_3$, 500 MHz): δ 7.85 (d, J=5 Hz, 1H), 7.86 (d, J=10 Hz, 2H), 8.06 (d, J=5 Hz, 1H), 8.25 (d, J=10 Hz, 2H). ESI(+)-HRMS [M+H]$^+$ calculated 400.9990, observed 400.9982 for C$_{14}$H$_7$F$_3$N$_4$O$_3$S$_2$.

3-(4-trifluoromethoxybenzenesulfonyl)-4H-thieno[2,3-e][1,2,3]triazolo[1,5-a]pyrimidin-5-one (15c)

The reaction mixture is purified by flash column chromatography, using DCM:MeOH [50:1, plus Et$_3$N (1%)]. The combined fractions were taken up into chloroform and washed by HCl (1M aq., twice). Colorless solid, yield 12%. $^1$H NMR (CDCl$_3$, 500 MHz): δ 7.37 (d, J=5 Hz, 1H), 7.73 (d, J=5 Hz, 2H), 8.16 (d, J=10 Hz, 1H), 8.30 (d, J=10 Hz, 2H).

3-(4-methoxybenzenesulfonyl)-4H-thieno[1,2,3-e][1,2,3]triazolo[1,5-a]pyrimidin-5-one (15d)

The reaction mixture is purified by flash column chromatography, using DCM:MeOH [50:1, plus Et$_3$N (1%)]. The combined fractions were taken up into CHCl$_3$ and washed by 1M (aq. HCL, twice). Yellow solid, yield 32%. $^1$H NMR (CDCl$_3$, 300 MHz): δ 3.87 (s, 3H), 7.02 (d, J=15 Hz, 2H), 7.84 (d, J=10 Hz, 1H), 8.02 (d, J=10 Hz, 1H), 8.03 (d, J=10 Hz, 2H). $^{13}$C NMR (CDCl3, 75 Hz): δ 56.4, 115.4, 117.7, 130.7, 138.1. ESI(+)-HRMS [M+H]$^+$ calculated 363.0221, observed 363.0216 for C$_{14}$H$_{10}$N$_4$O$_4$S$_2$.

3-(thiophene-2-sulfonyl)-4H-thieno[2,3-e][1,2,3]triazolo[1,5-a]pyrimidin-5-one (15e)

Brown solid, yield 11%. $^1$H NMR (CDCl$_3$, 300 MHz): δ 7.15-7.18 (mult, 1H), 7.74 (d, J=6 Hz, 1H), 7.86 (d, J=6 Hz, 1H), 7.91 (d, J=6 Hz, 1H), 8.04 (d, J=6 Hz, 1H). ESI(+)-HRMS [M+H]$^+$ calculated 338.9680, observed 338.9677 for C$_{11}$H$_6$N$_4$O$_3$S$_3$.

3-(4-fluorobenzenesulfonyl)-4H-thieno[2,3-e][1,2,3]triazolo[1,5-a]pyrimidin-5-one (15f)

White solid, yield 43%. $^1$H NMR (CDCl$_3$, 500 MHz): δ 7.85 (d, J=5 Hz, 1H), 8.05 (d, J=5 Hz, 1H), 8.13 (mult, 2H). ESI(+)-HRMS [M+Na]$^+$ calculated 372.9842, observed 372.9832 for C$_{13}$H$_7$FN$_4$O$_3$S$_2$.

3-(4-bromobenzenesulfonyl)-4H-thieno[1,2,3-e][1,2,3]triazolo[1,5-a]pyrimidin-5-one (15g)

Yellow solid, yield 53%. $^1$H NMR (CDCl$_3$, 500 MHz): δ 7.72 (d, J=10 Hz, 2H), 7.85 (d, J=5 Hz, 1H), 7.97 (d, J=10 Hz, 2H), 8.05 (d, J=5 Hz, 1H). ESI(+)-HRMS [M+Na]$^+$ calculated 432.9041, observed 432.9018 for C$_{13}$H$_7$BrN$_4$O$_3$S$_2$. (see, e.g., Ivachtchenko et al., *Bioorg. Med. Chem.* 18(14), 5282-5290 (2010); *Epub* 2010 May 24).

3-(4-difluoroethylbenzenesulfonyl)-4H-thieno[2,3-e][1,2,3]triazolo[1,5-a]pyrimidin-5-one (15h)

White solid, yield 74%. $^1$H NMR (CDCl$_3$, 300 MHz): δ 1.91 (t, J=18.0 Hz, 3H), 7.70 (d, J=9.0 Hz, 2H), 7.84 (d, J=6.0 Hz, 1H), 8.04 (d, J=3.0 Hz, 1H), 8.17 (d, J=9.0 Hz, 2H). ESI(+)-HRMS [M+H]$^+$ calculated 397.0240, observed 397.0251 for C$_{15}$H$_{10}$F$_2$N$_4$O$_3$S$_2$.

Example 10

Coupling of Heterocyclic Lactams with Primary Amines to Generate Amidines

General Conditions for Coupling of Heterocyclic Lactams (15a-h) with Primary Amines to Generate Amidines (3a-k)
Heterocyclic lactam starting material (15a-h) (1 mol eq) was dissolved in anhydrous CH$_3$CN (0.3M) and treated with primary amine (3 mol eq) and DBU (3 mol eq) and PyBOP (3 mol eq) and the mixture was irradiated by microwave at 100° C. for 30 min. HPLC was performed, showing consumption of starting material and formation of tentative product. The crude reaction mixture was treated with 1M HCl (10 eq) and stirred for 30 min at RT. Sodium carbonate (1M aq) was added to adjust pH to 9. The crude reaction mixture was dissolved in ethyl acetate, washed with HCl (1M, three times). The organic layer was concentrated in vacuum and the product typically precipitated out. The reaction mixture sat overnight, after which the crystalline product was isolated by vacuum filtration. In certain cases, the products were purified by tritueration with CHCl$_3$. Additional or alternative purification measures are documented below for individual compounds. See also Synthesis Scheme 4 described herein.

[3-(4-Isopropylbenzenesulfonyl)-thieno[2,3-e][1,2,3]triazolo[1,5-a]pyrimidin-5-yl]-thiophen-2-ylmethyl-amine (3a)

Crude product was purified by flash column chromatography using pure DCM [+AcOH (1%)] to isolate the SM, then changed to DCM:MeOH [50:1, plus AcOH (1%)]. Isolated product as a yellow solid, yield 21%. $^1$H NMR (DMSO-d$_6$, 300 MHz): δ 1.17 (d, J=9 Hz, 6H), 2.91-2.95 (mult, 1H), 4.97 (d, J=6 Hz, 2H), 7.03-7.04 (mult, 1H), 7.23-7.24 (mult, 1H), 7.39 (d, J=9 Hz, 2H), 7.45-7.46 (mult, 1H) 7.95-7.98 (mult, 1H), 7.99-8.01 (mult, 2H), 8.42 (d, J=6 Hz, 1H), 9.48 (t, J=3 Hz, 1H). $^{13}$C NMR (CDCl$_3$, 125 Hz): δ 24.6, 34.6, 117.5, 126.5, 128.0, 128.3, 128.4, 138.0, 140.5, 155.5, 156.5. ESI(+)-HRMS [M+H]$^+$ calculated 470.0779, observed 470.0782 for C$_{21}$H$_{19}$N$_5$O$_2$S$_3$. Compound 3a is also called herein compound 2bn.

Furan-2-ylmethyl-[3-(4-isopropyl-benzenesulfonyl)-thieno[2,3-e][1,2,3]triazolo[1,5-a]pyrimidin-5-yl]-amine (3b)

Crude product was purified by flash column chromatography using pure DCM [+AcOH (1%)] to isolate the SM, then changed to DCM:MeOH [100:1, plus Et$_3$N (1%)]. Yellow solid, yield 3%. $^1$H NMR (CDCl$_3$, 500 MHz): δ 1.20 (d, J=5 Hz, 6H), 2.92-2.94 (mult, 1H), 4.20-4.23 (mult, 2H), 7.05 (s, 1H), 7.17 (t, J=5 Hz, 1H), 7.35 (d, J=5 Hz, 2H), 7.53 (mult, 1H), 8.14 (d, J=5 Hz, 2H), 8.19 (d, J=5 Hz, 1H), 8.36 (d, J=5 Hz, 2H). This compound is commercially available and reported (see, e.g., Ivachtchenko et al., *Bioorg. Med. Chem.* 18(14), 5282-5290 (2010); Epub 2010 May 24).

Thiophen-2-ylmethyl-[3-(4-trifluoromethyl-benzenesulfonyl)-thieno[2,3-e][1,2,3]triazolo[1,5-a]pyrimidin-5-yl]-amine (3c)

Crude product was purified by flash column chromatography using pure DCM (+AcOH (1%)) to isolate the SM, then changed to DCM:MeOH [100:1, plus Et$_3$N (1%)]. Solid, yield 26%. $^1$H NMR (CDCl$_3$, 300 MHz): δ 5.17 (d, J=6 Hz, 2H), 7.04-7.05 (mult, 1H), 7.51 (d, J=6 Hz, 1H), 7.53 (d, J=6 Hz, 1H), 7.68-7.71 (mult, 2H), 7.93 (d, J=6 Hz, 1H), 8.00 (d, J=6 Hz, 1H), 8.33-8.35 (mult, 2H). ESI(+)-HRMS [M+H]$^+$ calculated 400.9990, observed 400.9982 for C$_{14}$H$_7$F$_3$N$_4$O$_3$S$_2$.

Thiophen-2-ylmethyl-[3-(4-trifluoromethoxy-benzenesulfonyl)-thieno[2,3-e][1,2,3]triazolo[1,5-a]pyrimidin-5-yl]-amine (3d)

Additional purification: Prep-RP-HPLC, yield 2%. $^1$H NMR (CDCl$_3$, 500 MHz): δ 5.17 (d, J=5 Hz, 2H), 5.80 (t, J=5 Hz, 1H), 7.03-7.05 (mult, 1H), 7.22 (d, J=5 Hz, 1H), 7.25 (d, J=10 Hz, 2H), 7.30 (d, J=5 Hz, 1), 7.93 (d, J=5 Hz, 1H), 8.00

(d, J=5 Hz, 1H), 8.26 (d, J=10 Hz, 2H). ESI(+)-HRMS [M+H]+ calculated 512.0132, observed 512.0139 for $C_{19}H_{12}F_3N_5O_3S_3$.

[3-(4-Isopropyl-benzenesulfonyl)-thieno[2,3-e][1,2,3]triazolo[1,5-a]pyrimidin-5-yl]-(4-methoxy-benzyl)-amine (3e)

The crude product was purified by flash column chromatography using pure DCM [+AcOH (1%)] to isolate SM, and then changed to DCM:MeOH [50:1, plus acetic acid (1%)]. Solid, yield 20%. $^1$H NMR (CDCl$_3$, 300 MHz): δ 1.21 (d, 6H, J=6 Hz), 2.89-2.93 (mult, 1H), 4.92 (d, J=6 Hz, 2H), 6.93 (d, J=9 Hz 2H), 7.17 (d, J=3 Hz, 1H), 7.42 (d, J=9 Hz, 2H), 7.89-7.91 (mult, 2H), 7.97-7.98 (mult, 1H), 8.12 (d, J=9 Hz, 2H). LC-ESI-LRMS [M+H]+ calculated 494.1; observed 494.0 for $C_{24}H_{23}N_5O_3S_2$.

[3-(4-Methoxy-benzenesulfonyl)-thieno[2,3-e][1,2,3]triazolo[1,5-a]pyrimidin-5-yl]-thiophen-2-ylmethyl-amine (3f)

The crude product was purified by flash column chromatography using DCM:MeOH [120:1, plus AcOH (1%)]. Brown solid, yield 36%. $^1$H NMR (CDCl$_3$, 500 MHz): δ 3.82 (s, 3H), 5.17 (d, J=10 Hz, 2H), 6.90-6.93 (mult, 2H), 7.04 (d, J=5 Hz, 1H), 7.23 (d, J=5 Hz, 1H), 7.30 (dd, J=10 Hz, 5 Hz, 1H), 7.91 (d, J=10 Hz, 1H), 8.00 (d, J=10 Hz, 1H), 8.16 (d, J=15 Hz, 2H). $^{13}$C NMR (CDCl$_3$, 125 Hz): δ 41.0, 50.3, 114.7, 114.8, 118.1, 126.4, 127.9, 128.0, 134.0, 134.2, 139.2, 139.5, 140.2, 153.2, 164.1. ESI(+)-HRMS [M+H]+ calculated 458.0415, observed 458.0421 for $C_{19}H_{15}N_5O_3S_3$.

[3-(Thiophene-2-sulfonyl)-thieno[2,3-e][1,2,3]triazolo[1,5-a]pyrimidin-5-yl]-thiophen-2-ylmethyl-amine (3g)

Solid, yield 10%. $^1$H NMR (MeOH-d$_4$, 500 MHz): δ 5.09 (s, 2H), 6.98 (dd, J=5 Hz, 1H), 7.08 (dd, J=5 Hz, 1H), 7.23 (d, 1H), 7.29 (d, J=5 Hz, 1H), 7.80 (dd, J=10 Hz, 5 Hz, 1H), 7.82 (dd, J=5 Hz, 1H), 7.96 (d, J=5 Hz, 1H), 8.25 (d, J=5 Hz, 1H).

[3-(4-Fluoro-benzenesulfonyl)-thieno[2,3-e][1,2,3]triazolo[1,5-a]pyrimidin-5-yl]-thiophen-2-ylmethyl-amine (3h)

Yellow solid, yield 43%. $^1$H NMR (CDCl$_3$, 500 MHz): δ 5.16 (d, J=5 Hz, 2H), 5.74 (s, 1H), 7.04 (s, 1H), 7.11 (t, J=5 Hz, 2H), 7.22 (s, 1H), 7.31 (d, J=5 Hz, 1H), 7.92 (d, J=5 Hz, 1H), 8.00 (d, J=5 Hz, 1H), 8.23 (t, J=5 Hz, 2H). ESI(+)-HRMS [M+H]+ calculated 446.0215, observed 446.0220 for $C_{18}H_{12}FN_5O_2S_3$.

[3-(4-Bromo-benzenesulfonyl)-thieno[2,3-e][1,2,3]triazolo[1,5-a]pyrimidin-5-yl]-thiophen-2-ylmethyl-amine (3i)

Solid, yield 35%. $^1$H NMR (CDCl$_3$, 500 MHz): δ 5.16 (d, J=5 Hz, 2H), 5.78 (t, J=5 Hz, 1H), 7.04-7.06 (mult, 1H), 7.32-7.33 (mult, 1H), 7.33 (mult, 1H), 7.58 (d, J=10 Hz, 2H), 7.93 (d, J=5 Hz, 1H), 8.00 (d, J=5 Hz, 1H), 8.05 (d, J=10 Hz, 2H).). This compound is commercially available and reported (see, e.g., Ivachtchenko et al., *Bioorg. Med. Chem.* 18(14), 5282-5290 (2010); Epub 2010 May 24).

[3-(4-Isopropyl-benzenesulfonyl)-thieno[2,3-e][1,2,3]triazolo[1,5-a]pyrimidin-5-yl]-naphthalen-1-ylm-ethyl-amine (3j)

Crude material was purified by flash column chromatography using pure DCM (+AcOH (1%)) to isolate SM, then changed to DCM:MeOH [50:1 plus AcOH (1%)]. Solid, yield 32%. $^1$H NMR (CDCl$_3$, 500 MHz): δ 1.19 (d, J=5 Hz, 6H), 2.88 (mult, 1H), 5.46 (d, J=5 Hz, 2H), 5.61 (t, J=5 Hz, 1H), 7.47-7.51 (mult, 1H), 7.53 (d, J=5 Hz, 2H), 7.55 (s, 1H), 7.56 (s, 1H), 7.62 (d, J=5 Hz, 1H), 7.91 (d, J=5 Hz, 1H), 7.95 (d, J=5 Hz, 1H), 7.98 (d, J=5 Hz, 1H), 8.10 (d, J=5 Hz, 1H), 8.13 (d, J=10 Hz, 2H). LC-ESI-LRMS [M+H]+ calculated 514.1 observed 514.0 for $C_{27}H_{23}N_5O_2S_2$.

{3-[4-(1,1-Difluoro-ethyl)-benzenesulfonyl]-thieno[2,3-e][1,2,3]triazolo[1,5-a]pyrimidin-5-yl}-thiophen-2-ylmethyl-amine (3k)

After microwave irradiation, the reaction mixture was treated with 1 M HCl (10 eq), stirred 10 minutes, and then extracted with DCM (×3). The organic layer was washed with HCl (aq. 1M) three times, and then was dried over Na$_2$SO$_4$. The organic layer was concentrated in vacuo, and the product was precipitated by the addition of MeOH and was then isolated by vacuum filtration. The final product was purified by triteration with a small amount of CHCl3, to generate the final product (3k) as a white solid, yield 15%. $^1$H NMR (acetone-d$_6$, 300 MHz): δ 1.94 (s, J=18.0 Hz, 3H), 5.15 (s, 2H), 7.01 (dd, J=9.0, 3.0 Hz, 1H), 7.30-7.31 (mult, 1H), 7.36-7.39 (mult, 1H). 7.72 (d, J=6.0 Hz, 2H), 7.97 (d, J=6.0 Hz, 1H), 8.26 (d, J=9.0 Hz, 2H), 8.34 (d, J=6.0 Hz, 1H). $^{13}$C NMR (acetone-d$_6$, 125 MHz): δ 25.0 (t, J=28.8 Hz), 39.7, 114.5, 116.7, 125.3, 125.8 (t, J=5.0 Hz), 127.0, 127.1, 127.0, 131.4, 135.6, 139.1, 141.0, 141.9, 142.6 (t, J=27.5 Hz), 144.6, 153.7. LC-ESI(+)-HRMS [M+H]+ calculated 492.0356, observed 492.0423 for $C_{15}H_{10}F_2N_4O_3S_2$.

Example 11

Figure 8:
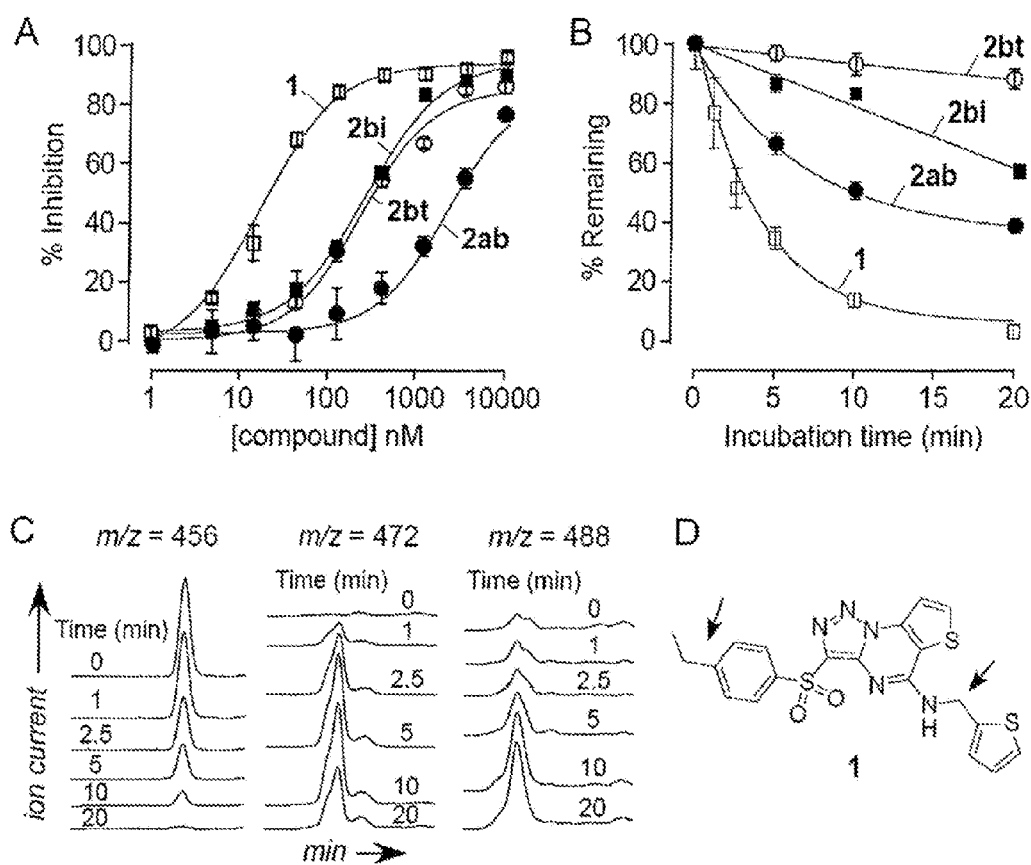
FIG. 8A-D illustrate the UT-B inhibition potency and metabolic stability of selected triazolothienopyrimidine analogues.

Structure-Activity Relationships of Triazolothienopyrimidine UT-B Inhibitors Initial SAR was deduced from analysis of 273 commercially available triazolothieno-pyrimidine analogues of the UT-B inhibitor, UTB$_{inh}$-14 (also called inhibitor 1 in this example). UT-B inhibition was measured by an erythrocyte lysis assay. Of the compounds tested, 103 compounds inhibited UT-B urea permeability by >60% at 25 μM. Twelve compounds had IC$_{50}$<500 nM, with IC$_{50}$ of 22 nM for UTBi$_{nh}$-14. FIG. 8A shows concentration-inhibition data for selected inhibitors. The data fitted well to a single-site inhibition model with near 100% inhibition at high concentration. Table 1 provides IC$_{50}$ and metabolic stability data for 75 compounds (2aa-2cw).

Figure 9:
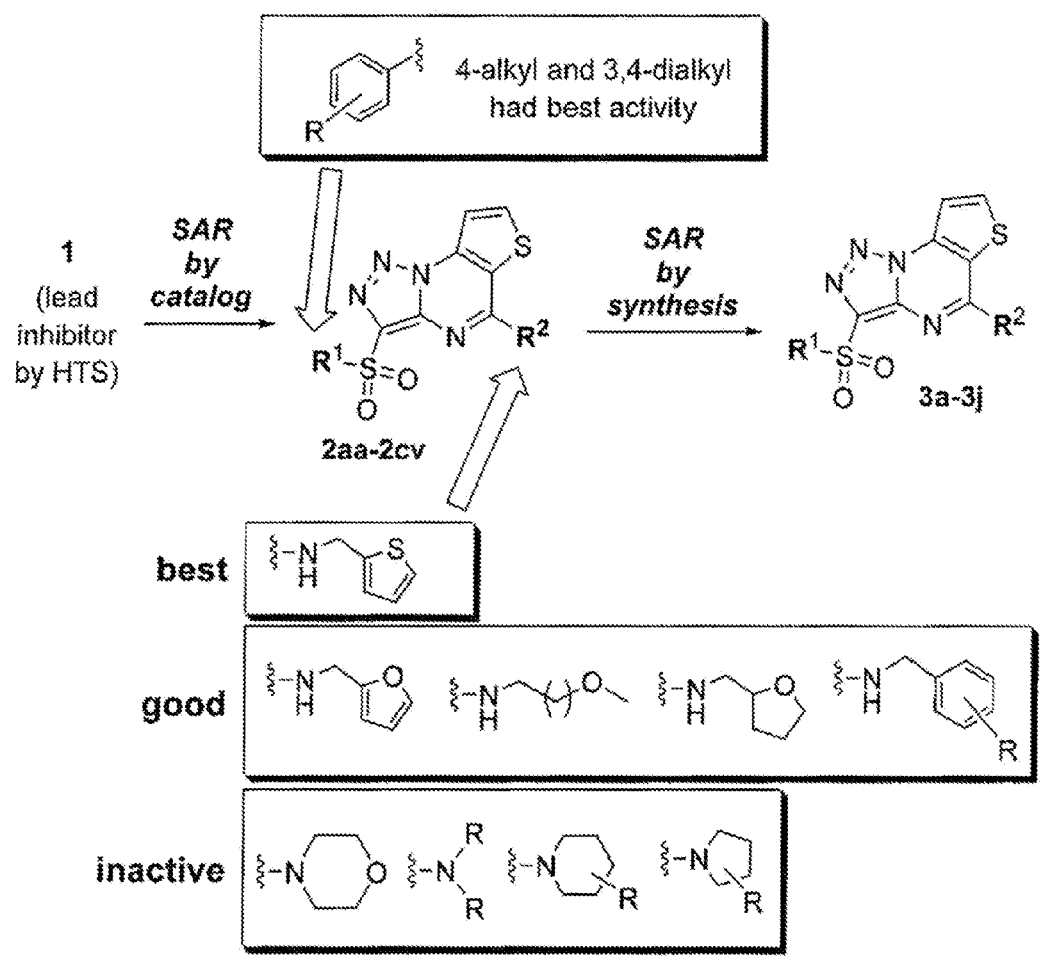
FIG. 9 presents a general strategy for optimization of triazolothienopyrimidines. Structural determinants of triazolothienopyrimidine inhibition activity identified from commercially available analogs ('SAR-by-catalog') followed by synthesized of a focused library.

SAR analysis indicated greatest potency for thiophene-2-methylamine at the R$^2$ group. Replacing the heteroaryl sulfur atom by oxygen (thiophene→furan) increased IC$_{50}$ approximately 10 fold from 22 to 239 nM (compare UTB$_{inh}$-14 and 2 bp, Table 1). Bulky R$^2$ groups constrained cyclic rings such as morpholine (2bq, IC$_{50}$ 5.6 mM) and piperidine (IC$_{50}$>25 mM, not shown) greatly reduced activity. The reduced activity with inclusion of a bulky group is consistent with our previous docking model of UTB$_{inh}$-14 to a homology model of UT-B (described above) showing a sterically tight fit near the amidine linkage. Analogs containing a flexible chain with a terminal ether group (2cb, IC$_{50}$ 212 nM) showed moderate potency. At $R^1$, only compounds with alkyl- and halide-substituted aryl sulfonyl ring were available. 4-Methylphenyl and 2,5-dimethylphenyl reduced inhibition potency, whereas 3,4-dimethyl, 4-isopropyl and 4-ethyl increased potency (compare 2 bp and 2cs). Halide-substitution also reduced potency (2bi). Having a two or three carbon hydrophobic group at the meta- and para-position of the aryl ring might increase potency due to a tighter binding into hydrophobic binding pocket of UT-B. FIG. 9 summarizes the major findings of SAR analysis of commercially available analogues of $UTB_{inh}$-14.

In vitro analysis of metabolic stability was done using LC/ESI-MS following compound incubation with hepatic microsomes in the presence of NADPH. FIG. 8B shows kinetics of the microsomal degradation of selected compounds. $UTB_{inh}$-14 showed rapid degradation with $t_{1/2}$ approximately 2.8 min, with appearance of metabolic products at 16 AMU (1× oxygen) or 32 (2× oxygen) as determined (FIG. 8C). As observed by the relative growth of the peaks at m/z=472 versus 488, the first oxidation event appears to be more rapid than the second. Without wishing to be bound by any particular theory, $UTB_{inh}$-14 may undergo rapid hydroxylation at either the benzylic (see, e.g., Khojasteh-Bakht et al., *Xenobiotica*, 2003, 33:1201-1210) or thiophene-2-methylamine linking carbons, positions that are thought to stabilize radical intermediates (FIG. 8D). Metabolic stability was measured of several analogues of $UTB_{inh}$-14 (Table 1). Analogues with $R^1$ substituted with para-chlorophenyl showed greater stability (2bg-2bi), likely because of absence of the benzylic hydroxylation site, and also due to occupation of the para position, which is a known site in P450 metabolism (see, e.g., Baldwin et al., *Br. J. Clin. Pharmacol.*, 1999, 48:424-32). Analogs with $R^2$ bearing electron-rich benzylamine (2ad, 2aj, 2bc, 2bt) also showed improved metabolic stability; however, these analogs have poorer UT-B inhibition potency when compared to $UTB_{inh}$-14.

Example 12

Synthesis of Triazolothienopyrimidine Analogs

SAR of commercial analogs of $UTB_{inh}$-14 indicated thiophene-2-methylamine as the optimal $R^2$ substituent for inhibition potency. The optimal $R^1$ substituent was not identified. A library of focused analogs was prepared to identify aspects of the SAR that were missing from the commercially available inhibitor set (Table 1), with the aim of maintaining or improving UT-B inhibition potency and improving metabolic stability. Most of the synthesized compounds were designed to maintain the $R^2$ substituent as thiophene-2-methylamine, while investigating a small number of alkyl (3a, 3c), alkoxy (3d, 3f), halo (3h, 3i), and heteroaryl (3g) substituents at $R^1$ (see Table 2). A small number of additional inhibitors with variation of $R^2$ (substitutions for thiophene-2-methylamine) was also explored (3b, 3e, and 3j) to confirm the importance of this heterocycle. One novel compound (3k), the 1,1-difluoroethyl analog of $UTB_{inh}$-14, was synthesized to be bioisosteric with ethyl but lacking the benzylic hydrogens that are likely involved in the poor metabolic stability of $UTB_{inh}$-14.

The general synthetic approach begins with the synthesis of aryl sulfonyl acetonitrile building blocks (General Scheme 1 described herein). More specifically, as shown in Scheme 1a, commercially available substituted arylthiols (4a-4g) were alkylated with bromoacetonitrile to generate the corresponding sulfides (5a-5g), which were then oxidized with mCPBA to give the desired aryl sulfonyl acetonitriles 6a-6g.

An additional variation of this building block (4-difluoroethylphenyl) was prepared by a multi-step approach (General Scheme 2 and Scheme 2a described herein) due to unavailability of the precursor benzenethiol. As such, 1-bromo-4-(1,1-difluoroethyl)benzene (7) was transformed under Pd-catalyzed conditions with the Xanthphos ligand, analogous to the Buchwald-Hartwig reaction, to generate sulfide ester 7. This was oxidized to sulfone 9, converted to primary amide 10, and dehydrated using phosphorous pentoxide to the desired 4-difluoroethyl aryl sulfone acetonitrile (6 or 6h).

The second key synthetic precursor is a 3-azidothiophene ester (General Scheme 3 and Scheme 3a). 3-Bromothiophene-2-carboxaldehyde (11a) was azidated by nucleophilic aromatic substitution to generate 3-azidothiophene 12a. This aldehyde was oxidized with the Lindgren reaction (see, e.g., Lindgren et al., *Acta Chemica Scandinavica*, 27:888 (1973)) to generate carboxylic acid 13a, which was alkylated with isobutyl bromide to 2-azidothiophene-1-isobutyl ester (14a). (Note that the reactants and intermediates in Scheme 3 are also described in FIG. 1C for the synthesis of $UT_{inh}$-14. No difference in these reactants and intermediates is intended by differences in numbering of same. For example, reactant 1 in FIG. 1C is the same as reactant 11 in Scheme 3.) The attachment of the building blocks is illustrated in Scheme 4 described herein. The aryl sulfonyl acetonitriles 6a-6h were reacted with base to form the nitrile enolates, and coupled with the azidothiophene ester 14a, followed by in situ lactamation to generate the core heterocycles (15a-15h). The conversion of this intermediate to the final library of amidine-containing compounds (3a-3k) was affected with PyBOP with microwave irradiation. The use of PyBOP with microwave irradiation was based on conditions using the related reagent BOP without heating (see, e.g., Wan et al., *Org. Lett.* 8:2425-28 (2006): Wan et al., *J. Org. Chem*, 72:10194-210 (2007)); however, the low-temperature conditions were not successful with triazolothienopyrimidines for BOP or PyBOP. With microwave-assistance, PyBOP readily caused quantitative conversion to the desired amidine products, and was chosen over BOP due to its carcinogenic byproduct hexamethylphosphoramide (HMPA).

Example 13

Methods for Analyzing Biological Activity of Inhibitors Described in Examples 14 and 15

The experimental detail for biological assays used for characterizing compounds shown in Tables 1 and 2 is provided below.

Blood Collection.

Whole blood was collected from 8-12 week-old (25-35 g) wild-type mice in a CD1 genetic background by orbital puncture following subcutaneous injection of sodium heparin. Procedures were approved by the UCSF Committee on Animal Research. Human venous blood was collected into heparinized tubes, stored at 4° C., and used within 48 h.

Erythrocyte Lysis Assay of UT-B Inhibition.

Whole blood was diluted to a hematocrit of ~1% in PBS containing 1.25 M acetamide and 5 mM glucose. 100 μL of the erythrocyte suspension was added to each well of a 96-well round-bottom microplate to which inhibitor was added from DMSO stock solution. After 10 min incubation, 20 μL of the erythrocyte suspension was added rapidly to one well of a 96-well plate (Costar, Corning, N.Y.) containing 180 μL isosmolar buffer (PBS containing 1% DMSO). Erythrocyte lysis was quantified by absorbance at 710 nm, as described (Levin et al., supra 2007). Percentage erythrocyte lysis was calculated using control values from the same plate as: % lysis=100%·($A_{neg}$−$A_{test}$)/($A_{neg}$−$A_{pos}$), where $A_{test}$ is the absorbance value from a test well.

Stopped-Flow Measurement of Erythrocyte Urea Permeability.

Measurements were done using a Hi-Tech Sf-51 instrument (Wiltshire, UK). Whole blood (mouse or human) was diluted in PBS (hematocrit approximately 0.5%), incubated with inhibitor for 5 min and then subjected to a 100-mM inwardly directed urea gradient. The kinetics of increasing cell volume caused by urea influx was measured as the time-course of 90° scattered light intensity at 530 nm. Urea permeability and percentage inhibition were computed as described (see, e.g., Levin et al., supra 2007).

In Vitro Metabolic Stability.

Compounds, each at 5 µM, were incubated for specified times at 37° C. with rat liver microsomes (1 mg protein/ml; Sigma-Aldrich, St. Louis, Mo.) in potassium phosphate buffer (100 mM) containing 1 mM NADPH. The mixture was then chilled on ice, and 0.5 ml of ice-cold ethyl acetate was added. Samples were centrifuged for 15 min at 3,000 rpm, the supernatant evaporated to dryness, and the residue was dissolved in 150 µl mobile phase (acetonitrile:water 3:1, containing 0.1% formic acid) for LC/MS. Reverse-phase HPLC separations were carried out using a Waters C18 column (2.1×100 mm, 3.5 mm particle size) equipped with a solvent delivery system (Waters model 2690, Milford, Mass.). The solvent system consisted of a linear gradient from 5 to 95% acetonitrile run over 16 min (0.2 mL/min flow rate).

Mouse Studies.

Compound 3k (described herein) was formulated in 5% DMSO, 2.5% Tween-80 and 2.5% PEG400 in $H_2O$, as described above in Example 7. Mice (age 8-10 weeks, 25-35 g) were administered 300 µL of formulation (without or with 3k) by intraperitoneal injection. Urine, blood and kidney samples were collected and processed (see Example 7). dDAVP ([1-deamino-8-D-arginine]-vasopressin, 1 µg/kg) was given 1 h after formulation. Urine osmolality was measured in water-diluted urine samples by freezing-point osmometry. Kidneys were homogenized in acetic acid (100 µL per 1 g tissue) and ethyl acetate (10 mL per 1 g tissue). The homogenate was centrifuged at 3,000 rpm for 15 min. Calibration standards were prepared in kidney homogenates from untreated mice to which was added known amounts of 3k. The ethyl acetate-containing supernatant was dried under nitrogen and the residue dissolved in acetonitrile:$H_2O$ (3:1) containing 0.1% formic acid. HPLC was done on a XTERRA MS C18 column (2.1×100 mm, 3.5 µm particle size; Waters, Milford, Mass.) connected to a solvent delivery system (model 2690; Waters). The solvent system consisted of a linear gradient from 5% to 95% acetonitrile containing 0.1% formic acid over 16 min (0.2 mL/min flow). 3k was detected by absorbance at 262 nm. Mass spectra were acquired on a mass spectrometer (Alliance HT 2790+ZQ; Waters) using positive ion detection. For analysis of blood and urine, fluids were diluted with equal volume of water and extracted with ethyl acetate.

Example 14

Potency and Metabolic Stability of Triazolothienopyrimidine Analogs

Figure 10:
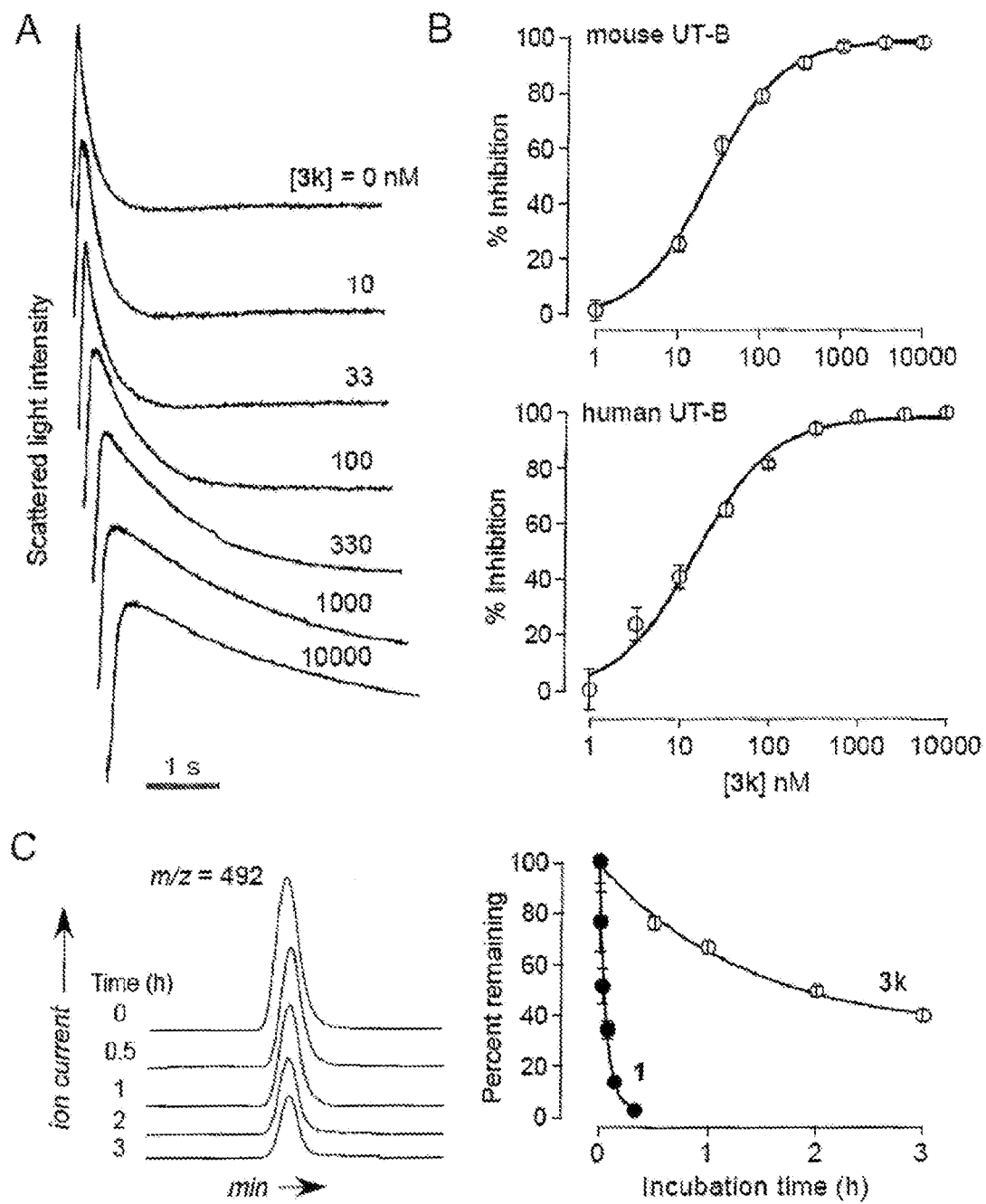
FIGS. 10A-C illustrate UT-B inhibition and in vitro metabolic stability of compound 3k.

The $IC_{50}$ and in vitro metabolic stability of synthesized analogs were determined (Table 2). In general, analogs lacking stabilized benzylic carbon for hydroxylation showed improved metabolic stability (3c, 3d, 3i). The compound 3k showed both excellent inhibition potency and metabolic stability, and was further characterized. UT-B inhibition by 3k was measured by stopped-flow light scattering, which provides a definitive measure of compound potency. The assay measures the kinetics of cell volume following rapid mixing of an erythrocyte suspension with a urea-containing solution. FIG. 10A shows representative light scattering data for inhibition of UT-B urea transport in mouse erythrocytes. Each curve consists of a rapid upward phase, representing osmotic cell shrinkage, followed by a slower downward phase, representing urea (and water) influx. The kinetics of the downward phase was greatly slowed by 3k in a concentration-dependent manner. FIG. 10B summarizes concentration-inhibition data for mouse and human UT-B. Deduced $IC_{50}$ were 23 and 15 nM, respectively.

FIG. 10C showed in vitro metabolic stability in hepatic microsomes. In parallel experiments, the $t_{1/2}$ for disappearance of 3k was approximately 120 min, substantially slower than that of $t_{1/2}$ approximately 2.8 min for disappearance of $UTB_{inh}$ 14 shown for comparison. Thus, compared to $UTB_{inh}$ 14, compound 3k is approximately 40-fold more stable in vitro while retaining comparable potency.

Example 15

In Vivo Mouse Studies

Figure 11:
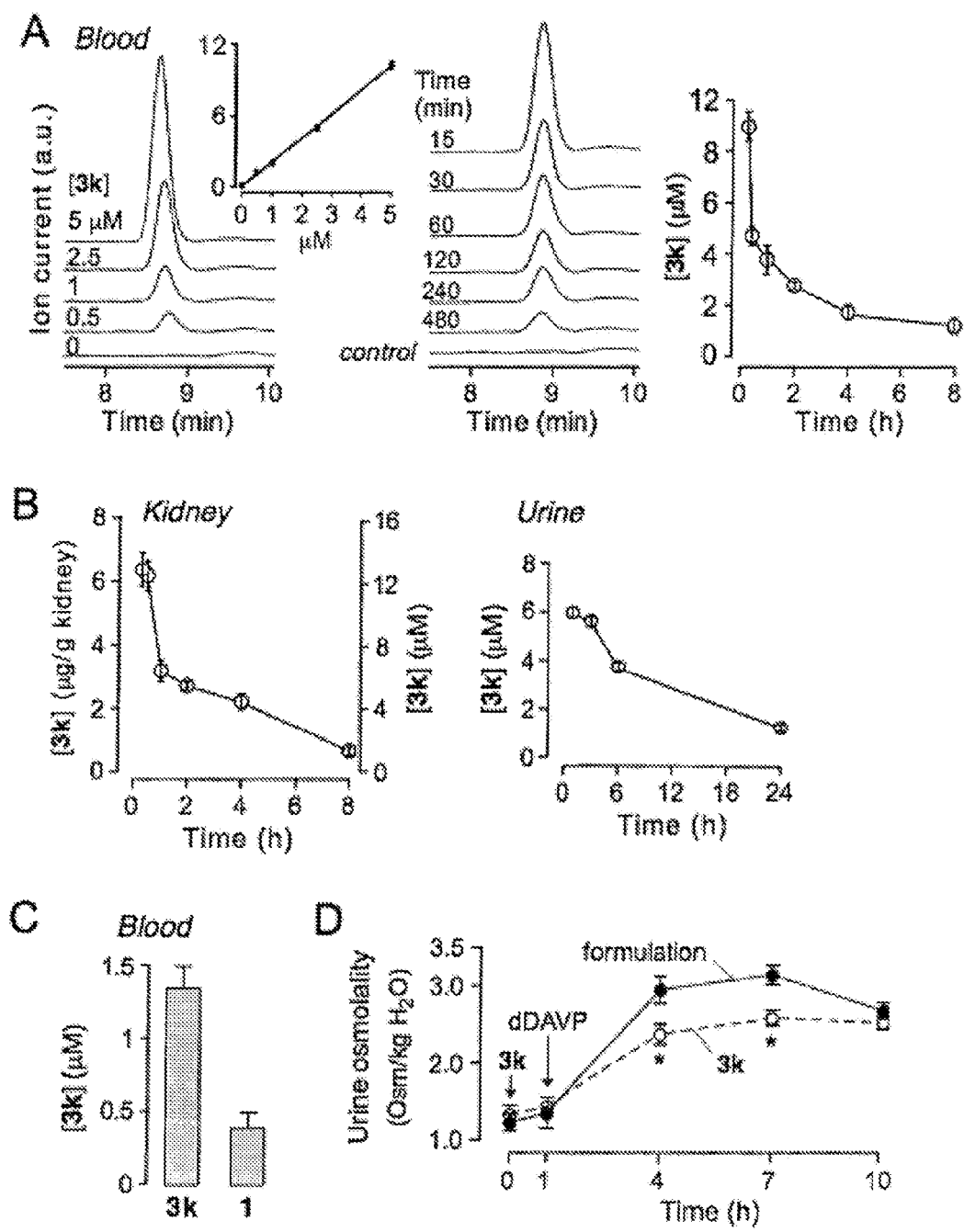
FIGS. 11A-D present data illustrating the in vivo pharmacology and ureareatic efficacy of compound 3k.

The pharmacokinetics and renal accumulation of compound 3k was measured in mice following intraperitoneal bolus administration of 400 µg 3k in a suitable formulation chosen for efficient dissolution and absorption. Blood, urine, and kidney tissues were obtained at different times, and 3k was assayed by LC/MS after organic extraction, comparing with appropriate standards. FIG. 11A shows the LC/MS calibration for blood measurements (left), and the kinetics of 3k concentration (right); FIG. 11B shows the kinetics of 3k concentration in kidney and urine. These data show high concentrations (<1 µM) of 3k for many hours, well above its $IC_{50}$ approximately 25 nM for inhibition of UT-B urea transport. In a separate comparative study, mice received 200 µg of 3k and $UTB_{inh}$ 14 at the same time by intraperitoneal injection. At 6 h, 3k concentration was approximately 3-fold greater than $UTB_{inh}$ 14 in blood (FIG. 11C).

The urearetic activity of 3k was assayed by measurement of urine osmolality in mice under maximal antidiuretic stimulation by the vasopressin analog dDAVP. dDAVP was administrated 1 h after intraperitoneal injection of formulation without or with 3k. FIG. 11D shows that dDAVP increased urine osmolality to >3 Osm/kg $H_2O$ in control (formulation alone) mice, which was reduced by approximately 0.5 Osm/kg $H_2O$ in mice receiving 3k. This reduction in urine osmolality is similar to that produced by UT-B gene knockout (see, e.g., Yang et al., *J. Biol. Chem.* 277:10633-137 (2002)).

TABLE 1

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|------|-------|-------|----------------|-----------------------------------------------------------|
| 2aa | phenyl | piperidine-4-carboxamide | 7660 | |
| 2ab | phenyl | NH-CH$_2$CH$_2$CH$_2$-OCH$_3$ | 4348 | 27 |
| 2ac | p-tolyl | NH-CH$_2$-furan | 2145 | |
| 2ad | p-tolyl | NH-CH$_2$-(4-methoxyphenyl) | 1665 | 80 |
| 2ae | p-tolyl | NH-CH$_2$-tetrahydrofuran | 5744 | |
| 2af | p-tolyl | NH-CH$_2$CH$_2$CH$_2$-O-iPr | 11666 | |
| 2ag | p-tolyl | NH-CH(CH$_3$)-phenyl | 11227 | |
| 2ah | p-tolyl | NH-CH$_2$-(3-methoxyphenyl) | 2749 | |

TABLE 1-continued

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2ai | 4-methylphenyl | NH-CH$_2$CH$_2$-OCH$_3$ | 2870 | |
| 2aj | 4-methylphenyl | NH-CH$_2$-(4-fluorophenyl) | 733 | 86 |
| 2ak | 4-methylphenyl | 4-ethylpiperazin-1-yl | 7884 | |
| 2al | 4-methylphenyl | NH-cyclopentyl | 6380 | |
| 2am | 3,4-dimethylphenyl | NH-CH$_2$-(furan-2-yl) | 156 | <2 |
| 2an | 3,4-dimethylphenyl | morpholin-4-yl | 1711 | 6 |
| 2ao | 3,4-dimethylphenyl | NH-CH$_2$-phenyl | 1002 | 3 |
| 2ap | 3,4-dimethylphenyl | N(CH$_2$CH$_3$)$_2$ | 2494 | |

TABLE 1-continued

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2aq | 3,4-dimethylphenyl | 1-(piperidin-4-yl)carboxamide | 2118 | |
| 2ar | 3,4-dimethylphenyl | 2-methoxybenzylamino | 883 | 26 |
| 2as | 3,4-dimethylphenyl | 2-methoxybenzylamino | 1042 | 15 |
| 2at | 3,4-dimethylphenyl | 4-methoxybenzylamino | 1542 | 12 |
| 2au | 3,4-dimethylphenyl | isopentylamino | 854 | 35 |
| 2av | 3,4-dimethylphenyl | isopropylamino | 2194 | |
| 2aw | 3,4-dimethylphenyl | 3-ethoxypropylamino | 520 | 2 |
| 2ax | 3,4-dimethylphenyl | 3-isopropoxypropylamino | 2483 | |

TABLE 1-continued

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2ay | 3,4-dimethylphenyl | -NH-CH$_2$-(3-methoxyphenyl) | 3769 | |
| 2az | 3,4-dimethylphenyl | piperidin-1-yl | 1760 | <2 |
| 2ba | 3,4-dimethylphenyl | -NH-CH$_2$CH$_2$-OCH$_3$ | 2504 | |
| 2bb | 3,4-dimethylphenyl | -NH-cyclohexyl | 8186 | |
| 2bc | 3,4-dimethylphenyl | -NH-CH$_2$-(4-chlorophenyl) | 582 | 83 |
| 2bd | 3,4-dimethylphenyl | -NH-CH$_2$-(thiophen-2-yl) | 37 | <2 |
| 2be | 3,4-dimethylphenyl | -NH-CH$_2$-(4-fluorophenyl) | 5638 | |
| 2bf | 4-chlorophenyl | -NH-CH$_2$-(furan-2-yl) | 1866 | 21 |

TABLE 1-continued

UT-B inhibition potency and in vitro metabolic stability of
commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2bg | 4-Cl-C$_6$H$_4$ | NH-butyl | 1265 | 74 |
| 2bh | 4-Cl-C$_6$H$_4$ | NH-CH$_2$CH$_2$OCH$_3$ | 1906 | 63 |
| 2bi | 4-Cl-C$_6$H$_4$ | NH-CH$_2$-(2-thienyl) | 214 | 52 |
| 2bj | 4-Cl-C$_6$H$_4$ | NH-CH$_2$CH$_2$CH$_2$OCH$_3$ | 2306 | |
| 2bk | 4-iPr-C$_6$H$_4$ | NH-CH$_2$-(tetrahydrofuran-2-yl) | 2661 | |
| 2bl | 4-iPr-C$_6$H$_4$ | NH-CH$_2$CH$_2$CH$_2$OEt | 4079 | |
| 2bm | 4-iPr-C$_6$H$_4$ | NH-butyl | 191 | <2 |

TABLE 1-continued

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2bn | 4-isopropylphenyl | NH-CH$_2$-(2-thienyl) | 125 | |
| 2bo | 4-isopropylphenyl | NH-CH$_2$CH$_2$-OCH$_3$ | 711 | 14 |
| 2bp | 4-ethylphenyl | NH-CH$_2$-(2-furyl) | 239 | 12 |
| 2bq | 4-ethylphenyl | morpholino | 5709 | |
| 2br | 4-ethylphenyl | NH-CH$_2$-phenyl | 664 | 44 |
| 2bs | 4-ethylphenyl | N(CH$_2$CH$_3$)$_2$ | 1766 | 6 |
| 2bt | 4-ethylphenyl | NH-CH$_2$-(4-chlorophenyl) | 374 | 81 |

TABLE 1-continued
UT-B inhibition potency and in vitro metabolic stability of commercially available analogues of UTB$_{inh}$-14
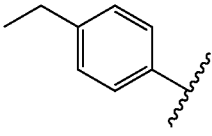 [SMILES: *c1ccc(CC)cc1]
| Cmpd | R¹ | R² | IC$_{50}$ (nM) | % Remaining after 10 min incubation with liver microsomes |
|---|---|---|---|---|
| 2bu | 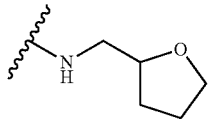 [SMILES: *NCC1CCCO1] | 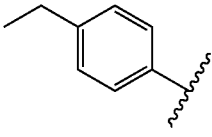 | 891 | 26 |
| 2bv | 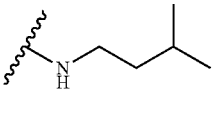 | 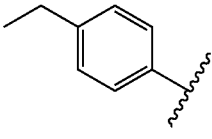 [SMILES: *c1ccc(CC)cc1] | 662 | 59 |
| 2bw | 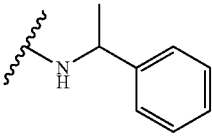 [SMILES: *NC(C)c1ccccc1] | 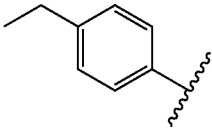 [SMILES: *c1ccc(CC)cc1] | 585 | 34 |
| 2bx | 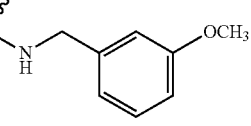 | 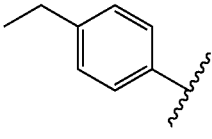 [SMILES: *c1ccc(CC)cc1] | 291 | <2 |
| 2by | 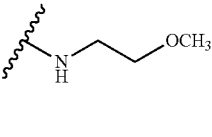 | 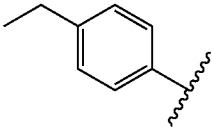 [SMILES: *c1ccc(CC)cc1] | 334 | <2 |
| 2bz | 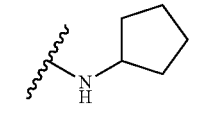 [SMILES: *NC1CCCC1] | 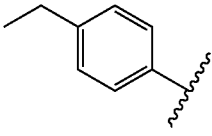 [SMILES: *c1ccc(CC)cc1] | 1543 | |
| 2ca | 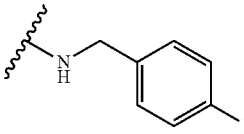 | 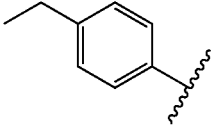 [SMILES: *c1ccc(CC)cc1] | 384 | 41 |
| 2cb | 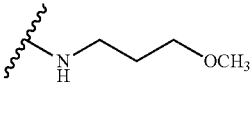 [SMILES: *NCCCOC] | | 212 | <2 |

TABLE 1-continued
UT-B inhibition potency and in vitro metabolic stability of commercially available analogues of UTB$_{inh}$-14
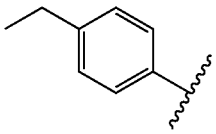 [SMILES: *c1ccc(CC)cc1]
| Cmpd | R$^1$ | R$^2$ | IC$_{50}$ (nM) | % Remaining after 10 min incubation with liver microsomes |
|---|---|---|---|---|
| 2cc | 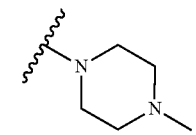 [SMILES: *N1CCN(C)CC1] | 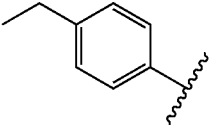 [SMILES: *c1ccc(CC)cc1] | 590 | |
| 2cd | 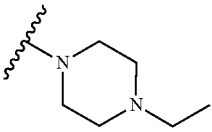 [SMILES: *N1CCN(CC)CC1] | 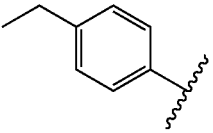 | 11925 | |
| 2ce | 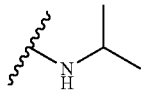 | 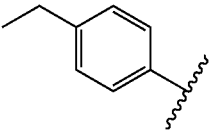 | 948 | 4 |
| 2cf | 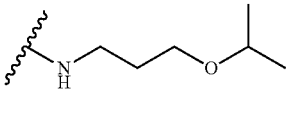 [SMILES: *NCCCOC(C)C] | 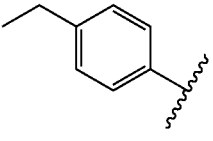 [SMILES: *c1ccc(CC)cc1] | 433 | <2 |
| 2cg | 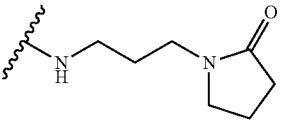 [SMILES: *NCCCN1CCCC1=O] | 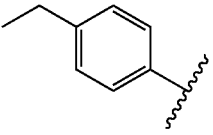 [SMILES: *c1ccc(CC)cc1] | 1496 | 2 |
| 2ch | 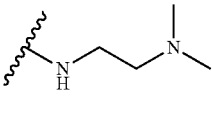 | 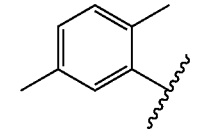 | 8460 | |
| 2ci | 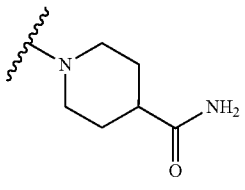 [SMILES: *N1CCC(C(N)=O)CC1] | 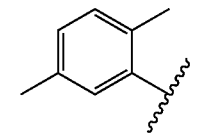 | 3341 | |
| 2cj | 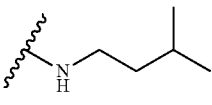 | | 1447 | 61 |

TABLE 1-continued

UT-B inhibition potency and in vitro metabolic stability of commercially available analogues of UTB$_{inh}$-14

| Cmpd | R$^1$ | R$^2$ | IC$_{50}$ (nM) | % Remaining after 10 min incubation with liver microsomes |
|---|---|---|---|---|
| 2ck | 2,4-dimethylphenyl | −NH−(CH$_2$)$_3$−O−CH$_2$CH$_3$ | 9847 | |
| 2cl | 2,4-dimethylphenyl | −NH−(CH$_2$)$_3$−O−CH(CH$_3$)$_2$ | 2058 | |
| 2cm | 2,4-dimethylphenyl | −NH−CH(CH$_3$)−Ph | 702 | |
| 2cn | 2,4-dimethylphenyl | −NH−(CH$_2$)$_3$CH$_3$ | 865 | 57 |
| 2co | 2,4-dimethylphenyl | −NH−CH$_2$CH$_2$−OCH$_3$ | 1187 | 29 |
| 2cp | 2,4-dimethylphenyl | −NH−CH$_2$−(4-F-C$_6$H$_4$) | 671 | |
| 2cq | 2,4-dimethylphenyl | −NH−CH$_2$−Ph | 1647 | |
| 2cr | 2,4-dimethylphenyl | −NH−(CH$_2$)$_3$−OCH$_3$ | 1402 | 26 |

TABLE 1-continued

UT-B inhibition potency and in vitro metabolic stability of commercially available analogues of UTB$_{inh}$-14

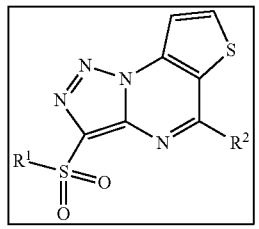

| Cmpd | R$^1$ | R$^2$ | IC$_{50}$ (nM) | % Remaining after 10 min incubation with liver microsomes |
|---|---|---|---|---|
| 2cs | 2,5-dimethylphenyl | NHCH$_2$-furan-2-yl | 2662 | |
| 2ct | 4-bromophenyl | NHCH$_2$CH$_2$OCH$_3$ | 959 | 53 |
| 2cu | 4-bromophenyl | NH-butyl | 1897 | 76 |
| 2cv | 3-chlorophenyl | piperidine-4-carboxamide (N-linked) | 3140 | |
| 2cw | 3-chlorophenyl | NHCH$_2$-thiophen-2-yl | 2083 | |

TABLE 2

UT-B inhibition activity[a] and microsomal stability[b] of synthesized UT-B inhibitors.

| Cmpd | R[1] | R[2] | IC$_{50}$ (nM) | % Remaining[b] |
|---|---|---|---|---|
| 1 | 4-ethylphenyl | thiophen-2-ylmethylamino | 11 | <5 |
| 3a | 4-isopropylphenyl | thiophen-2-ylmethylamino | 153 | <5 |
| 3b | 4-isopropylphenyl | furan-2-ylmethylamino | 16552 | >99 |
| 3c | 4-(trifluoromethyl)phenyl | thiophen-2-ylmethylamino | 537 | 99 |
| 3d | 4-(trifluoromethoxy)phenyl | thiophen-2-ylmethylamino | 1116 | 95 |
| 3e | 4-isopropylphenyl | (4-methoxybenzyl)amino | 5291 | 7 |
| 3f | 4-methoxyphenyl | thiophen-2-ylmethylamino | 104 | 6 |
| 3g | thiophen-2-yl | thiophen-2-ylmethylamino | 196 | <5 |

TABLE 2-continued

UT-B inhibition activity[a] and microsomal stability[b] of synthesized UT-B inhibitors.

| Cmpd | R¹ | R² | IC$_{50}$ (nM) | % Remaining[b] |
|------|----|----|----------------|----------------|
| 3h | 4-F-phenyl | NH-CH$_2$-thiophene | 468 | 27 |
| 3i | 4-Br-phenyl | NH-CH$_2$-thiophene | 32 | 60 |
| 3j | 4-iPr-phenyl | NH-CH$_2$-naphthyl | >2500 | 45 |
| 3k | 4-(CF$_2$CH$_3$... 1,1-difluoroethyl)-phenyl | NH-CH$_2$-thiophene | 14 | 96 |

[a]Determined using red blood cell lysis assay (n = 3). Data were fitted to a single-site saturation model.
[b]Percent remaining of parent molecule after 30 min incubation with rat liver microsomes.

Compound 3a in Table 2 is the same as compound 2bn in Table 1. As noted herein, Compound 1 in the above Table is the same compound as UTB$_{inh}$-14 described herein.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A method for treating a disease or disorder treatable by inhibiting transport of urea in a subject, said method comprising administering to the subject a pharmaceutical composition comprising a pharmaceutically acceptable excipient and a compound of structure (I):

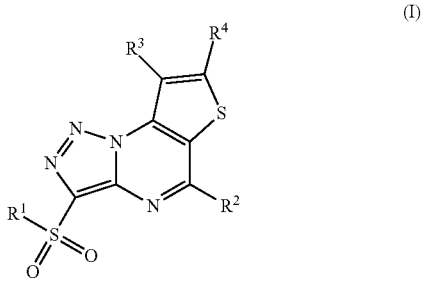

(I)

or a single stereoisomer, a mixture of stereoisomers, tautomer or pharmaceutically acceptable salt thereof, wherein, R$^1$ is optionally substituted aryl or optionally substituted heteroaryl;
R$^2$ is —N(R$^5$)(R$^6$);
R$^3$ and R$^4$ are each independently hydrogen, alkyl, halo or haloalkyl;
R$^5$ is hydrogen or alkyl; and
R$^6$ is optionally substituted alkyl, optionally substituted cycloalkyl, optionally substituted heterocyclylalkyl, optionally substituted aralkyl, or optionally substituted heteroarylalkyl; or
R$^5$ and R$^6$, together with the nitrogen atom to which they are attached, form an optionally substituted N-heterocycle, or optionally substituted N-heteroaryl.

2. The method of claim 1 wherein R$^1$ is optionally substituted phenyl and the compound has a structure of structure (II):

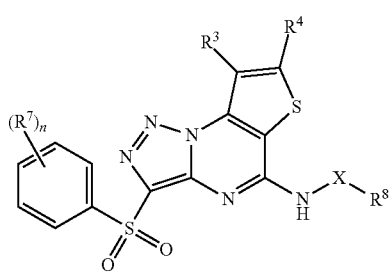

(II)

wherein,
n is 0, 1, 2 or 3;
X is an alkylene chain;
R$^3$ and R$^4$ are each independently hydrogen, alkyl, halo or haloalkyl;
R$^7$ is alkyl, halo, haloalkyl, or —OR$^9$;
R$^8$ is optionally substituted aryl, optionally substituted heteroaryl or optionally substituted heterocyclyl, or —OR$^9$; and
R$^9$ is hydrogen, alkyl or haloalkyl.

3. The method of claim 2 wherein,
n is 1 or 2;
X is a C$_{1-5}$ alkylene chain;
each R$^3$ and R$^4$ is independently hydrogen, alkyl, halo or haloalkyl;
R$^7$ is alkyl, halo, haloalkyl, or —OR$^9$;
R$^8$ is optionally substituted heteroaryl; and
R$^9$ is hydrogen, alkyl or haloalkyl.

4. The method of claim 3 wherein,
n is 1 or 2;
X is a C$_{1-3}$ alkylene chain;
R$^3$ and R$^4$ are each hydrogen;
R$^7$ is alkyl, halo, haloalkyl, or —OR$^9$;
R$^8$ is optionally substituted thiophenyl; and
R$^9$ is hydrogen, alkyl or haloalkyl.

5. The method of claim 4 wherein the compound is
{3-[4-(1,1-difluoro-ethyl)-benzenesulfonyl]-thieno[2,3-e][1,2,3]triazolo[1,5-a]pyrimidin-5-yl}-thiophen-2-ylmethyl-amine;
thiophen-2-ylmethyl-[3-(4-trifluoromethyl-benzenesulfonyl)-thieno[2,3-e][1,2,3]triazolo[1,5-a]pyrimidin-5-yl]-amine;
thiophen-2-ylmethyl-[3-(4-trifluoromethoxy-benzenesulfonyl)-thieno[2,3-e][1,2,3]triazolo[1,5-a]pyrimidin-5-yl]-amine;
{3-[4-methoxy-benzenesulfonyl]-thieno[2,3-e][1,2,3]triazolo[1,5-a]pyrimidin-5-yl}-thiophen-2-ylmethyl-amine;
{3-[4-fluoro-benzenesulfonyl]-thieno[2,3-e][1,2,3]triazolo[1,5-a]pyrimidin-5-yl}-thiophen-2-ylmethyl-amine;
{3-[4-bromo-benzenesulfonyl]-thieno[2,3-e][1,2,3]triazolo[1,5-a]pyrimidin-5-yl}-thiophen-2-ylmethyl-amine;
{3-[4-chloro-benzenesulfonyl]-thieno[2,3-e][1,2,3]triazolo[1,5-a]pyrimidin-5-yl}-thiophen-2-ylmethyl-amine;
{3-[3-chloro-benzenesulfonyl]-thieno[2,3-e][1,2,3]triazolo[1,5-a]pyrimidin-5-yl}-thiophen-2-ylmethyl-amine;
{3-[4-ethyl-benzenesulfonyl]-thieno[2,3-e][1,2,3]triazolo[1,5-a]pyrimidin-5-yl}-thiophen-2-ylmethyl-amine;
{3-[4-isopropyl-benzenesulfonyl]-thieno[2,3-e][1,2,3]triazolo[1,5-a]pyrimidin-5-yl}-thiophen-2-ylmethyl-amine; or
{3-[3,4-dimethyl-benzenesulfonyl]-thieno[2,3-e][1,2,3]triazolo[1,5-a]pyrimidin-5-yl}-thiophen-2-ylmethyl-amine.

6. The method of claim 3 wherein,
n is 1 or 2;
X is a C$_{1-3}$ alkylene chain;
R$^3$ and R$^4$ are each hydrogen;
R$^7$ is alkyl, halo, haloalkyl, or —OR$^9$;
R$^8$ is optionally substituted furanyl; and
R$^9$ is hydrogen, alkyl or haloalkyl.

7. The method of claim 6, wherein the compound is
furan-2-ylmethyl[3-(4-isopropyl-benzenesulfonyl)-thieno[2,3-e][1,2,3]triazolo[1,5-a]pyrimidin-5-yl]-amine;
furan-2-ylmethyl[3-(4-methyl-benzenesulfonyl)-thieno[2,3-e][1,2,3]triazolo[1,5-a]pyrimidin-5-yl]-amine;
furan-2-ylmethyl-[3-(3,4-dimethyl-benzenesulfonyl)-thieno[2,3-e][1,2,3]triazolo[1,5-a]pyrimidin-5-yl]-amine;
furan-2-ylmethyl[3-(4-chloro-benzenesulfonyl)-thieno[2,3-e][1,2,3]triazolo[1,5-a]pyrimidin-5-yl]-amine;
furan-2-ylmethyl[3-(4-ethyl-benzenesulfonyl)-thieno[2,3-e][1,2,3]triazolo[1,5-a]pyrimidin-5-yl]-amine; or
furan-2-ylmethyl[3-(2,5-dimethyl-benzenesulfonyl)-thieno[2,3-e][1,2,3]triazolo[1,5-a]pyrimidin-5-yl]-amine.

8. The method of claim 2 wherein,
n is 1 or 2;
X is a C$_{1-3}$ alkylene chain;
each R$^3$ and R$^4$ is independently hydrogen, alkyl, halo or haloalkyl;
R$^7$ is alkyl, halo, haloalkyl, or —OR$^9$;
R$^8$ is —OR$^9$; and
R$^9$ is hydrogen, alkyl or haloalkyl.

9. The method of claim 8 wherein the compound is
{3-benzenesulfonyl-thieno[2,3-e][1,2,3]triazolo[1,5-a]pyrimidin-5-yl}-3-methoxypropyl-amine;
{3-[4-methyl-benzenesulfonyl]-thieno[2,3-e][1,2,3]triazolo[1,5-a]pyrimidin-5-yl}-3-(1-methylethoxy)propyl-amine;
{3-[4-methyl-benzenesulfonyl]-thieno[2,3-e][1,2,3]triazolo[1,5-a]pyrimidin-5-yl}-2-methoxyethyl-amine;
{3-[3,4-dimethyl-benzenesulfonyl]-thieno[2,3-e][1,2,3]triazolo[1,5-a]pyrimidin-5-yl}-3-ethoxylpropyl-amine;
{3-[3,4-dimethyl-benzenesulfonyl]-thieno[2,3-e][1,2,3]triazolo[1,5-a]pyrimidin-5-yl}-3-(1-methylethoxyl)propyl-amine;

{3-[3,4-dimethyl-benzenesulfonyl]-thieno[2,3-e][1,2,3]
triazolo[1,5-a]pyrimidin-5-yl}-2-methoxyethyl-amine;
{3-[4-chloro-benzenesulfonyl]-thieno[2,3-e][1,2,3]tria-
zolo[1,5-a]pyrimidin-5-yl}-2-methoxyethyl-amine;
{3-[4-chloro-benzenesulfonyl]-thieno[2,3-e][1,2,3]tria-
zolo[1,5-a]pyrimidin-5-yl}-3-methoxypropyl-amine;
{3-[4-isopropyl-benzenesulfonyl]-thieno[2,3-e][1,2,3]
triazolo[1,5-a]pyrimidin-5-yl}-3-ethoxylpropyl-amine;
{3-[4-isopropyl-benzenesulfonyl]-thieno[2,3-e][1,2,3]
triazolo[1,5-a]pyrimidin-5-yl}-2-methoxyethyl-amine;
{3-[4-ethyl-benzenesulfonyl]-thieno[2,3-e][1,2,3]triazolo
[1,5-a]pyrimidin-5-yl}-2-methoxyethyl-amine;
{3-[4-ethyl-benzenesulfonyl]-thieno[2,3-e][1,2,3]triazolo
[1,5-a]pyrimidin-5-yl}-3-methoxypropyl-amine;
{3-[4-ethyl-benzenesulfonyl]-thieno[2,3-e][1,2,3]triazolo
[1,5-a]pyrimidin-5-yl}-3-(1-methylethoxyl)propyl-
amine;
{3-[2,5-dimethyl-benzenesulfonyl]-thieno[2,3-e][1,2,3]
triazolo[1,5-a]pyrimidin-5-yl}-3-ethoxypropyl-amine;
{3-[2,5-dimethyl-benzenesulfonyl]-thieno[2,3-e][1,2,3]
triazolo[1,5-a]pyrimidin-5-yl}-3-(1-methylethoxyl)
propyl-amine;
{3-[2,5-dimethyl-benzenesulfonyl]-thieno[2,3-e][1,2,3]
triazolo[1,5-a]pyrimidin-5-yl}-2-methoxyethyl-amine;
or
{3-[2,5-dimethyl-benzenesulfonyl]-thieno[2,3-e][1,2,3]
triazolo[1,5-a]pyrimidin-5-yl}-3-methoxypropyl-
amine.

10. The method of claim 2 wherein,
n is 1 or 2;
X is a $C_{1-2}$ alkylene chain;
each $R^3$ and $R^4$ is independently hydrogen, alkyl, halo or haloalkyl;
$R^7$ is alkyl, halo, haloalkyl, or —$OR^9$;
$R^8$ is optionally substituted aryl or optionally substituted heterocyclyl; and
$R^9$ is hydrogen, alkyl or haloalkyl.

11. The method of claim 10 wherein the compound is
[3-(4-isopropyl-benzenesulfonyl)-thieno[2,3-e][1,2,3]
triazolo[1,5-a]pyrimidin-5-yl]-(4-methoxy-benzyl)-
amine;
[3-(4-isopropyl-benzenesulfonyl)-thieno[2,3-e][1,2,3]
triazolo[1,5-a]pyrimidin-5-yl]-naphthalen-1-ylmethyl-
amine;
[3-(4-methyl-benzenesulfonyl)-thieno[2,3-e][1,2,3]tria-
zolo[1,5-a]pyrimidin-5-yl]-(4-methoxy-benzyl)-
amine;
[3-(4-methyl-benzenesulfonyl)-thieno[2,3-e][1,2,3]tria-
zolo[1,5-a]pyrimidin-5-yl]-(1-phenyl-1-methyl)me-
thyl-amine;
[3-(4-methyl-benz enesulfonyl)-thieno[2,3-e][1,2,3]tria-
zolo[1,5-a]pyrimidin-5-yl]-(3-methoxy-benzyl)-
amine;
[3-(4-methyl-benzenesulfonyl)-thieno[2,3-e][1,2,3]tria-
zolo[1,5-a]pyrimidin-5-yl]-(4-fluoro-benzyl)-amine;
[3-(3,4-dimethyl-benzenesulfonyl)-thieno[2,3-e][1,2,3]
triazolo[1,5-a]pyrimidin-5-yl]-benzyl-amine;
[3-(3,4-dimethyl-benzenesulfonyl)-thieno[2,3-e][1,2,3]
triazolo[1,5-a]pyrimidin-5-yl]-(2-chloro-benzyl)-
amine;
[3-(3,4-dimethyl-benzenesulfonyl)-thieno[2,3-e][1,2,3]
triazolo[1,5-a]pyrimidin-5-yl]-(2-methoxy-benzyl)-
amine;
[3-(3,4-dimethyl-benzenesulfonyl)-thieno[2,3-e][1,2,3]
triazolo[1,5-a]pyrimidin-5-yl]-(4-methoxy-benzyl)-
amine;
[3-(3,4-dimethyl-benzenesulfonyl)-thieno[2,3-e][1,2,3]
triazolo[1,5-a]pyrimidin-5-yl]-(3-methoxy-benzyl)-
amine;
[3-(3,4-dimethyl-benzenesulfonyl)-thieno[2,3-e][1,2,3]
triazolo[1,5-a]pyrimidin-5-yl]-(4-chloro-benzyl)-
amine;
[3-(3,4-dimethyl-benzenesulfonyl)-thieno[2,3-e][1,2,3]
triazolo[1,5-a]pyrimidin-5-yl]-(4-fluoro-benzyl)-
amine;
[3-(4-ethyl-benzenesulfonyl)-thieno[2,3-e][1,2,3]triazolo
[1,5-a]pyrimidin-5-yl]-benzyl-amine;
[3-(4-ethyl-benzenesulfonyl)-thieno[2,3-e][1,2,3]triazolo
[1,5-a]pyrimidin-5-yl]-(4-chloro-benzyl)-amine;
[3-(4-ethyl-benzenesulfonyl)-thieno[2,3-e][1,2,3]triazolo
[1,5-a]pyrimidin-5-yl]-(1-phenyl-1-methyl)methyl-
amine;
[3-(4-ethyl-benzenesulfonyl)-thieno[2,3-e][1,2,3]triazolo
[1,5-a]pyrimidin-5-yl]-(3-methoxy-benzyl)-amine;
[3-(4-ethyl-benzenesulfonyl)-thieno[2,3-e][1,2,3]triazolo
[1,5-a]pyrimidin-5-yl]-(4-fluoro-benzyl)-amine;
[3-(2,5-dimethyl-benzenesulfonyl)-thieno[2,3-e][1,2,3]
triazolo[1,5-a]pyrimidin-5-yl]-(1-phenyl-1-methyl)me-
thyl-amine;
[3-(2,5-dimethyl-benzenesulfonyl)-thieno[2,3-e][1,2,3]
triazolo[1,5-a]pyrimidin-5-yl]-(4-fluoro-benzyl)-
amine;
[3-(2,5-dimethyl-benzenesulfonyl)-thieno[2,3-e][1,2,3]
triazolo[1,5-a]pyrimidin-5-yl]-benzyl-amine;
tetrahydrofuran-2-ylmethyl-[3-(4-methyl-benzenesulfo-
nyl)-thieno[2,3-e][1,2,3]triazolo[1,5-a]pyrimidin-5-
yl]-amine;
tetrahydrofuran-2-ylmethyl-[3-(4-isopropyl-benzene-
sulfonyl)-thienol[2,3-e][1,2,3]triazolo[1,5-a]pyrimi-
din-5-yl]-amine; or
tetrahydrofuran-2-ylmethyl-[3-(4-ethyl-benzenesulfo-
nyl)-thieno[2,3-e][1,2,3]triazolo[1,5-a]pyrimidin-5-
yl]-amine.

12. The method of claim 1 wherein
$R^1$ is optionally substituted heteroaryl;
$R^2$ is —$N(R^5)(R^6)$;
each $R^3$ and $R^4$ is independently hydrogen, alkyl, halo or haloalkyl;
$R^5$ is hydrogen or alkyl; and
$R^6$ is optionally substituted alkyl, optionally substituted cycloalkyl, optionally substituted heterocyclylalkyl, optionally substituted aralkyl, or optionally substituted heteroarylalkyl.

13. The method of claim 12 wherein the compound is [3-(thiophene-2-sulfonyl)-thieno[2,3-e][1,2,3]triazolo[1,5-a]pyrimidin-5-yl]-thiophen-2-ylmethyl-amine.

14. The method of claim 1, wherein the disease or disorder treatable by inhibiting transport of urea is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

15. A compound of structure (III):

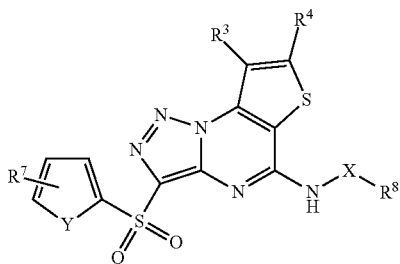

(III)

or a single stereoisomer, a mixture of stereoisomers, tautomer or pharmaceutically acceptable salt thereof, wherein, X is an alkylene chain;

Y is —CH=CH$_2$—, —CH=N—, S, or O;

each $R^3$ and $R^4$ is independently hydrogen, alkyl, halo or haloalkyl;

$R^7$ is —C($R^{10}$)($R^{11}$)—$R^{12}$, —OR$^9$ or halo;

$R^8$ is optionally substituted aryl, optionally substituted heteroaryl or optionally substituted heterocyclyl, or —OR$^9$;

$R^9$ is alkyl or haloalkyl;

$R^{10}$ and $R^{11}$ are each independently halo or alkyl; and $R^{12}$ is alkyl, halo or haloalkyl, wherein when Y is —CH=CH$_2$— and $R^7$ is isopropyl at the position para to the linking carbon, $R^8$ is not furanyl or thiophenyl, and when Y is —CH=CH$_2$— and $R^7$ is Br at the position para to the linking carbon, $R^8$ is not thiophenyl.

16. The compound of claim 15 wherein,
Y is —CH=CH$_2$— or S; and
$R^8$ is optionally substituted heteroaryl.

17. The compound of claim 16 wherein $R^8$ is optionally substituted thiophenyl.

18. The compound of claim 17, wherein the compound is
3-[4-(1,1-difluoro-ethyl)-benzenesulfonyl]-thieno[2,3-e][1,2,3]triazolo[1,5-a]pyrimidin-5-yl}-thiophen-2-ylmethyl-amine;
thiophen-2-ylmethyl-[3-(4-trifluoromethyl-benzenesulfonyl)-thieno[2,3-e][1,2,3]triazolo[1,5-a]pyrimidin-5-yl]-amine;
thiophen-2-ylmethyl-[3-(4-trifluoromethoxy-benzenesulfonyl)-thieno[2,3-e][1,2,3]triazolo[1,5-a]pyrimidin-5-yl]-amine;
3-[4-methoxy-benzenesulfonyl]-thieno[2,3-e][1,2,3]triazolo[1,5-a]pyrimidin-5-yl}-thiophen-2-ylmethyl-amine;
3-[4-fluoro-benzenesulfonyl]-thieno[2,3-e][1,2,3]triazolo[1,5-a]pyrimidin-5-yl}-thiophen-2-ylmethyl-amine; or
[3-(thiophene-2-sulfonyl)-thieno[2,3-e][1,2,3]triazolo[1,5-a]pyrimidin-5-yl]-thiophen-2-ylmethyl-amine.

19. A pharmaceutical composition comprising the compound of claim 15 and a pharmaceutically acceptable excipient.

20. A method for treating a disease or disorder treatable by inhibiting transport of urea in a subject, said method comprising administering to the subject the pharmaceutical composition according to claim 19, wherein the disease or disorder is selected from (a) refractory edema associated with cirrhosis, nephritic syndrome, acute renal failure, chronic renal insufficiency, hypertension, or congestive heart failure; (b) syndrome of inappropriate antidiuretic hormone secretion (SIADH); (c) azotemia; (e) fluid retention; and (f) abnormal uresis.

* * * * *

UNITED STATES PATENT AND TRADEMARK OFFICE
CERTIFICATE OF CORRECTION

PATENT NO. : 9,303,042 B2  
APPLICATION NO. : 14/388645  
DATED : April 5, 2016  
INVENTOR(S) : Marc Anderson et al.

Page 1 of 1

It is certified that error appears in the above-identified patent and that said Letters Patent is hereby corrected as shown below:

In the Claims

Column 89, Line 52:
"[3-(4-methyl-benz enesulfonyl)-thieno[2,3-e][1,2,3]triazolo[1,5-a]pyrimidin-5-yl]-(3-methoxy-benzyl)-amine;" should read, --[3-(4-methyl-benzenesulfonyl)-thieno[2,3-e][1,2,3]triazolo[1,5-a]pyrimidin-5-yl]-(3-methoxy-benzyl)-amine;--.

Signed and Sealed this  
Twentieth Day of December, 2016

Michelle K. Lee  
*Director of the United States Patent and Trademark Office*

UNITED STATES PATENT AND TRADEMARK OFFICE
CERTIFICATE OF CORRECTION

PATENT NO. : 9,303,042 B2  
APPLICATION NO. : 14/388645  
DATED : April 5, 2016  
INVENTOR(S) : Marc Anderson et al.

Page 1 of 1

It is certified that error appears in the above-identified patent and that said Letters Patent is hereby corrected as shown below:

In the Specification

<u>Column 1, Line 19:</u>
Delete "and EY13574"

Signed and Sealed this
Third Day of December, 2024

Katherine Kelly Vidal
*Director of the United States Patent and Trademark Office*